US006541498B2

(12) United States Patent
Chan et al.

(10) Patent No.: US 6,541,498 B2
(45) Date of Patent: Apr. 1, 2003

(54) BENZENESULFONAMIDES AND THE USE THEREOF TO MODULATE THE ACTIVITY OF ENDOTHELIN

(75) Inventors: Ming Fai Chan, Encinitas, CA (US); Bore Gowda Raju, Fremont, CA (US); Adam Kois, San Diego, CA (US); Erik Joel Verner, Foster City, CA (US); Chengde Wu, Pearland, TX (US); Rosario Silvestre Castillo, San Diego, CA (US); Venkatachalapathi Yalamoori, San Diego, CA (US); Vitukudi Narayanaiyengar Balaji, Bangalore (IN); Kalyanaraman Ramnarayan, San Diego, CA (US)

(73) Assignee: Texas Biotechnology, Houston, TX (US)

( * ) Notice: Subject to any disclaimer, the term of this patent is extended or adjusted under 35 U.S.C. 154(b) by 79 days.

(21) Appl. No.: 09/749,716

(22) Filed: Dec. 27, 2000

(65) Prior Publication Data

US 2001/0036958 A1 Nov. 1, 2001

Related U.S. Application Data

(63) Continuation of application No. 09/439,802, filed on Nov. 12, 1999, which is a continuation of application No. 08/730,633, filed on Dec. 6, 1996, now Pat. No. 6,030,991, which is a continuation of application No. 08/416,199, filed on Apr. 4, 1995, now abandoned, which is a continuation-in-part of application No. 08/247,072, filed on May 20, 1994, now Pat. No. 5,571,821, and a continuation-in-part of application No. 08/222,287, filed on Apr. 5, 1994, now Pat. No. 5,591,761, and a continuation-in-part of application No. 08/142,159, filed on Oct. 21, 1993, now Pat. No. 5,464,853, and a continuation-in-part of application No. 08/142,552, filed on Oct. 21, 1993, now Pat. No. 5,514,691, and a continuation-in-part of application No. 08/100,565, filed on Jul. 30, 1993, now abandoned, and a continuation-in-part of application No. 08/100,125, filed on Jul. 30, 1993, now abandoned, and a continuation-in-part of application No. 08/065,202, filed on May 20, 1993, now abandoned.

(51) Int. Cl.$^7$ ............................................... A61K 31/42
(52) U.S. Cl. ..................................................... 514/380
(58) Field of Search ......................................... 514/380

(56) References Cited

U.S. PATENT DOCUMENTS

| | | | |
|---|---|---|---|
| 3,300,488 A | 1/1967 | Onoue et al. | 260/239.9 |
| 3,660,383 A | 5/1972 | Sumimoto et al. | 260/239.9 |
| 4,044,126 A | 8/1977 | Cook et al. | 424/243 |
| 4,364,923 A | 12/1982 | Cook et al. | 424/46 |
| 4,414,209 A | 11/1983 | Cook et al. | 424/243 |
| 4,752,613 A | 6/1988 | Floyd et al. | 514/438 |
| 5,082,838 A | 1/1992 | Naka et al. | 514/211 |
| 5,187,195 A | 2/1993 | Oohata | 514/610 |
| 5,198,548 A | 3/1993 | Beylin et al. | 546/136 |
| 5,230,999 A | 7/1993 | Suzuki et al. | 435/71 |
| 5,240,910 A | 8/1993 | Lam et al. | 514/11 |
| 5,248,807 A | 9/1993 | Fujimoto et al. | 560/75 |
| 5,292,740 A | 3/1994 | Burri et al. | 514/256 |
| 5,334,598 A | 8/1994 | Bagley et al. | 514/303 |
| 5,352,659 A | 10/1994 | Wakimasu et al. | 514/9 |
| 5,352,800 A | 10/1994 | Bills et al. | 548/539 |
| 5,382,569 A | 1/1995 | Cody et al. | 514/17 |
| 5,464,853 A | 11/1995 | Chan et al. | 514/378 |

(List continued on next page.)

FOREIGN PATENT DOCUMENTS

| | | |
|---|---|---|
| BE | 0862630 | 2/1978 |
| EP | 0248399 | 12/1987 |
| EP | 0496452 | 7/1992 |
| EP | 0558258 A1 | 9/1993 |
| EP | 0569193 A1 | 11/1993 |
| EP | 0626174 A2 | 11/1994 |
| EP | 0682016 A1 | 11/1995 |
| EP | 0702012 A1 | 3/1996 |
| EP | 0725067 A1 | 8/1996 |
| EP | 0768305 A1 | 4/1997 |
| GB | 2259450 | 3/1993 |
| JP | 63238006 | 4/1990 |
| WO | 9115479 | 10/1991 |
| WO | 9427979 | 12/1994 |
| WO | 9524385 | 9/1995 |
| WO | 9604759 | 4/1996 |
| WO | 9631492 | 10/1996 |
| WO | 9725321 | 7/1997 |
| WO | 9739000 | 10/1997 |
| WO | 9813366 | 2/1998 |
| WO | 9849162 | 11/1998 |
| WO | 9910345 | 3/1999 |
| WO | 0001389 | 1/2000 |

OTHER PUBLICATIONS

Haefliger et al., "Nitric oxide and endothelin–1 are important regulators of human ophthalmic artery," *Invest. Ophthalmol. Vis. Sci.* 33:2340–2343 (1992).

(List continued on next page.)

*Primary Examiner*—Deborah C. Lambkin
(74) *Attorney, Agent, or Firm*—Heller Ehrman White & McAuliffe LLP; Stephanie Seidman; Dale Rieger

(57) ABSTRACT

N-(5-isoxazolyl)benzenesulfonamides and N-(3-isoxazolyl) benzenesulfonamides and methods for modulating or altering the activity of the endothelin family of peptides are provided. In particular, N-(5-isoxazolyl) biphenylsulfonamides and N-(3-isoxazolyl) biphenylsulfonamides and methods for inhibiting the binding of an endothelin peptide to an endothelin receptor or increasing the activity of endothelin peptides by contacting the receptor with a sulfonamide are provided. N-isoxzolyl-4-biphenylsulfonamides are particularly preferred. These compounds exhibit activity as endothelin receptor B antagonists. Methods for treating endothelin-mediated disorders, particularly inflammatory diseases, such as asthma, by administering effective amounts of one or more of these sulfonamides or prodrugs thereof that inhibit or increase the activity of endothelin are also provided.

43 Claims, No Drawings

U.S. PATENT DOCUMENTS

| | | | | |
|---|---|---|---|---|
| 5,514,691 | A | 5/1996 | Chan et al. | 514/312 |
| 5,514,696 | A | 5/1996 | Murugesan | 514/380 |
| 5,565,485 | A | 10/1996 | Bagley et al. | 514/452 |
| 5,571,821 | A | 11/1996 | Chan et al. | 514/312 |
| 5,585,397 | A | 12/1996 | Tung et al. | 514/473 |
| 5,589,478 | A | 12/1996 | Yamada et al. | 514/269 |
| 5,591,728 | A | 1/1997 | de Nanteuil et al. | 514/80 |
| 5,591,761 | A | 1/1997 | Chan et al. | 514/380 |
| 5,594,021 | A | 1/1997 | Chan et al. | 514/378 |
| 5,599,811 | A | 2/1997 | Berryman et al. | 514/226.5 |
| 5,612,359 | A | 3/1997 | Murugesan | 514/365 |
| 5,641,793 | A | 6/1997 | Bradbury | 514/352 |
| 5,668,137 | A | 9/1997 | Phillips et al. | 514/255 |
| 5,668,176 | A | 9/1997 | Bagley et al. | 514/569 |
| 5,726,194 | A | 3/1998 | Osswald et al. | 514/362 |
| 5,783,705 | A | 7/1998 | Blok et al. | 548/247 |
| 5,804,585 | A | 9/1998 | Verner | 514/301 |
| 5,827,869 | A | 10/1998 | Murugesan | 514/374 |
| 5,846,990 | A | 12/1998 | Murugesan et al. | 514/374 |
| 5,962,490 | A | 10/1999 | Chan et al. | 514/380 |
| 5,977,117 | A | 11/1999 | Chan et al. | 514/380 |
| 6,013,655 | A | 1/2000 | Verner | 514/301 |
| 6,017,916 | A | 1/2000 | Berryman et al. | 514/233.8 |
| 6,017,951 | A | 1/2000 | Patt et al. | 514/464 |
| 6,030,991 | A | 2/2000 | Chan et al. | 514/380 |
| 6,043,241 | A | 3/2000 | Cheng et al. | 514/233.8 |
| 6,043,265 | A | 3/2000 | Murugesan et al. | 514/374 |
| 6,060,475 | A | 5/2000 | Bradbury et al. | 514/255 |
| 6,063,911 | A | 5/2000 | Vournakis et al. | 536/20 |
| 6,080,774 | A | 6/2000 | Murugesan et al. | 514/380 |
| 6,083,951 | A | 7/2000 | Bradbury | 514/256 |
| 6,083,955 | A | 7/2000 | Harada et al. | 514/269 |
| 6,107,320 | A | 8/2000 | Murugesan et al. | 514/379 |
| 6,133,263 | A | 10/2000 | Cheng et al. | 514/233.8 |
| 6,133,442 | A | 10/2000 | Breu et al. | 544/123 |

OTHER PUBLICATIONS

Marsden and Brenner, "Nitric Oxide and Endothelins: novel autocrine/paracrine regulators of the circulation," *Seminars in Nephrology* 11:169–185 (1991).

Schultz et al., "A role for endothelin and nitric oxide in the pressor response to diaspirin cross–linked hemoglobin," *J. Lab. Clin. Med.* 3:301–308 (1993).

Tanner et al., "Endothelium–derived nitric oxide, endothelin, and platelet vessel wall interaction: alterations in hypercholesterolemia and atherosclerosis," *Seminars in Thrombosis and Hemostasis* 19:167–175 (1993).

Vane and Botting, "Secretory functions of the vascular endothelium," *J. Physiol. Pharmocol.* 43:195–207 (1992).

Warner et al., "Rat endothelin in a vasodialtor in the isolated perfused mesentery of the rat," *Eur. J. Pharmacol.* 159:325–326 (1989).

Whittle et al., "Modulation of the vasodepressor actions of acetylcholine, brandykinin, substance P and endothelin in the rat by a specific inhibitor of nitric oxide formation," *Br. J. Pharmacol.* 98:646–652 (1989).

Arai et al., "Cloning and expression of a cDNA encoding an endothelin receptor," *Nature* 348: 730–732 (1990).

Barone et al., "Selective antagonism of endothelin–A–receptors improves outcome in both head trauma and focal stroke in rat," *J. Cardiovasc. Pharmacol.* 36(5 Suppl. 1): S357–S361 (2000).

Benigni, A. "Endothelin antagonists in renal disease," *Kidney Int.* 57: 1778–1794 (2000).

Benigni et al., "A specific endothelin subtype A receptor antagonist protects against injury in renal disease progression," *Kidney International* 44: 440–444 (1993).

Bkaily et al., "Presence of functional endothelin–1 receptors in nuclear membranes of human aortic vascular smooth muscle cells," *J. Cardiovasc. Pharmacol.* 36 (5 Suppl. 1): S414–S417 (2000).

Bolger et al., "Characterization of binding of the Ca + + channel antagonist, [3H]nitrendipine, to guinea–pig ileal smooth muscle," *J. Pharmacol. Exp. Ther.* 225: 291–309 (1983).

Bolger et al., "Characterization of intestinal smooth muscle responses and binding sites for endothelin," *Can. J. Physiol. Pharmacol.* 70: 377–384 (1992).

Bolger et al., "Interactions between endothelin and atrial natruiretic factor in the rat aortic ring preparation," *Can. J. Physiol. Pharmacol.* 69: 1155–1162 (1991).

Bolger et al., "Vascular reactivity, tissue levels, and binding sites for endothelin: A comparison in the spontaneously hypertensive and Wistar–Kyoto rats," *Can. J. Physiol. Pharm.* 69: 406–413 (1990).

Borges et al., "Tissue selectivity of endothelin," *Eur. J. Pharmacol.* 165: 223–230 (1989).

Bradbury et al., "New non–peptide endothelin–A receptor antagonists: synthesis, biological properties, and structure–activity relationships of 5–(dimethylamino)–N–pyridyl–,-N–pyrimidinyl–,-N–pyridazinyl–, and –N–pyrazinyl–1–naphthalenesulfonamides," *J. Med. Chem.* 40: 996–1004 (1997).

Brooks et al., "Effect of nifedipine on cyclosporine A–induced nephrotoxicity, urinary endothelin excretion and renal endothelin receptor number," *Eur. J. Pharmacol.* 194: 115–117 (1991).

Cardell et al., "Evidence for multiple endothelin receptors in the guinea–pig pulmonary artery and trachea," *Br. J. Pharmacol.* 105: 376–380 (1992).

Cardell et al., "Pituitary adenylate cyclase activating peptide (PACAP) in guniea–pig ling: distribution and dilatory effect," *Regul. Pept.* 36: 379–390 (1991).

Cardillo et al., "Increased activity of endogenous endothelin in patients with hypercholesterolemia," *J. Am. Coll. Cardiol.* 36: 1483–1488 (2000).

Castiglione et al., "Alanine scan of endothelin," Peptides: Chemistry and Biology, Proc. Amer. Rept. Symp. (Twelfth), J.A. Smith and J.E. Rivier, Eds., ESCOM, Leiden, 1992, pp. 402–403.

Certified Translation of Japanese Patent 63238006 (item CS), "Agent protecting against rice blase disease."

Certified Translation of French Publication (item EE) "Synthesis and Structure of N1–Acylated Sulfiodizole and its homologues."

Chakrabarti et al., "Therapeutic potential of endothelin receptor antagonists in diabetes," *Expert Opin. Investig. Drugs* 9: 2873–2888 (2000).

Chan et al., "The discovery and structure–activity relationships of nonpeptide, low molecular weight antagonists selective for the endothelin ET(B) receptor," *Bioorg. Med. Chem.* 6: 2301–2306 (1998).

Chan et al., "Identification of a new class of ETA selective endothelin antagonists by pharmacophore directed screening," *Biochem. Biophys. Res. Commun.* 201: 228–234 (1994).

Chemical Abstracts vol. 65, abstract No. 14649g, citing Uno et al., *Chem. Pharm. Bull.* 14: 756–762 (1966).

Clozel, et al., "Pathophysiological role of endothelin revealed by the first orally active endothelin receptor antagonist," *Nature 365*: 759–761 (1993).

Clozel, et al., "Endothelin receptor antagonists: current status and perspectives," *J. Cardiovasc. Pharmacol. 35*: (Suppl. 2); S65–S68 (2000).

Clozel, et al., "In vivo pharmacology of Ro 46–2005, the first synthetic nonpeptide endothelin receptor antagonist: implications for endothelin physiology," *J. Cardiovasc. Pharmacol. 22* (Suppl. 8): S377–S379 (1993).

Clozel, et al., "Pathophysiological role of endothelin revealed by the first orally active endothelin receptor antagonist," *Nature 365*: 759–761 (1993).

Cody et al., "Design of a potent combined pseudopeptide endothelin–A/endothelin–B receptor antagonist, Ac–DBhg 16–Leu–Asp–Ile–(NMe Ile–Trp21 (PD 1562520: examination of its pharmacokinetic and spectral properties," *J. Med. Chem. 40*: 2228–2240 (1997).

Cody et al., "The rational design of a highly potent combined $ET_A$ and $ET_B$ receptor antagonist (PD145065) and related analogues," *Med. Chem. Res. 3*: 154–162 (1993).

Database Crossfirre Beilstein Registry No. 1021364 and 1086426, citing Saito et al., *Yakugaku Zasshi 88*: 1289, 1292 (1968).

Derwent ™002020454 WPI Acc. No. 1978–33485A/197819, citing Belgium Patent No. BE 862630A, published May 2, 1978.

Doherty, A. M., "Endothelin: a new challenge," *J. Med. Chem. 35*: 1493–1508 (1992).

Doherty et al., "Discovery of a novel series of orally active non–peptide endothline–A (ETA) receptor–selective antagonist," *J. Med. Chem. 38*: 1259–1263 (1995).

Doherty et al., Structure–activity relationships of C–terminal endothelin hexapeptide antagonists, *J. Med. Chem. 36*: 2585–2594 (1993).

Ellahham et al., Bosentan and the endothelin system in congestive heart failure, *Clin. Cardiol. 23*: 803–807 (2000).

Endothelin, Receptor Antagonist (TBC 11251), *Research and Development—Compounds Under Development*, pp. 3–5 (available at http://www.tbc.com/resrch.htm on Sep. 3, 1997).

Evans et al., "Endothelins, their receptors, and retinal vascular dysfunction in galactose–fed rats," *Diabetes Res. Clin. Pract. 48*: 75–85 (2000).

Filep et al., "Endothelin–1 induces prostacyclin release from bovine aortic endothelial cells," *Biochem. Biophys. Res. Comm. 177*: 171–176 (1991).

Fujimoto et al., "A novel non–peptide endothelin antagonist isolated from bayberry," *FEBS 305*: 41–44 (1992).

Fujimoto and Sakai, "Synthesis and Structure of N1–Acylated Sulfiodizole and its homologues," *Chem. Pharm. Bull. 14*: 280–284 (1966). Published in French.

Fukuroda et al., "Analysis of responses to endothelins in isolated porcine blood vessels by using a novel endothelin antagonist, BQ–153," *Life Sci. 50*: PL107–PL112 (1992).

Furchgott and Zawadzki, "The obligatory role of endothelial cells in the relaxation of arterial smooth muscle by acetylcholine," *Nature 288*: 373–376 (1980).

Hammad et al., "The role of endothelin in early renal cortical reperfusion in renal transplantation," *Eur. Surg. Res. 32*: 380–388 (2000).

Hele et al., "Effect of endothelin antagonists, including the novel ET(A) receptor antagonist LBL 031, on endothelin–1 and lipopolysaccharide–induced microvascular leakage in rat airways," *Br. J. Pharmacol. 131*: 1129–1134 (2000).

Ihara et al., "Biological profiles of highly potent novel endothelin antagonists selective for the ETA receptor," *Life Sci. 50*: 247–255 (1992).

Ikeda et al., "Antihypertensive effects of a mixed endothelin–A– and –B–receptor antagonist, J–104132, were augmented in the presence of an AT1–receptor antagonist, MK–954," *J. Cardiovasc. Pharmacol. 36* (5 Suppl. 1): S337–S341 (2000).

Inoue et al., "The human endothelin family: three structurally and pharmacologically distinct isopeptides predicted by three separate genes," *Proc. Natl. Acad. Sci. USA 86*: 2863–2867 (1989).

Ishikawa et al., "Cyclic pentapeptide endothelin antagonists with high $ET_A$ selectivity. Potency– and solubility–enhancing modifications," *J. Med. Chem. 35*: 2139–2142 (1992).

IUPAC–IUB Commission on Biochemical Nomenclature, *Biochem. 11*: 942–944 (1972).

Jae et al., "Pyrrolidine–3–carboxylic acids as endothelin antagonists. 2. Sulfonamide–based ETA/ETB mixed antagonists," *J. Med. Chem. 40*: 3217–3227 (1997).

Kaltenbronn et al., "Renin inhibitors containing isosteric replacements of the amide bond connecting the P3 and P2 sites," *J. Med. Chem. 33*: 838–845 (1990).

Kanda et al., "Discovery and synthesis of a potent sulfonamide ET(B) selective antagonists," *Bioorg. Med. Chem. Lett. 10*: 19875–1978 (2000).

Kanno et al., "Endothelin–1 and Vasculitis," *J. Amer. Med. Assoc. 264*: 2868 (1990).

Kloog and Sokolovsky, "Similarities in mode and sites of action of sarafotoxins and endothelins," *Trends Pharmacol. Sci. 10*: 212–214 (1989).

Kojiri et al., "Endothelin–binding inhibitors, BE–18257A and BE–18257B. I. Taxonomy, fermentation, isolation, and characterization," *J. Antibiot. (Tokyo) 44*: 1342–1347 (1991).

Kurihara et al., "Impaired development of the thyroid and thymus in endothelin–1 knockout mice," *J. Cardiovasc. Pharmacol. 26(Suppl. 3)*: S13–S16 (1995).

Kurihara et al., "The possible role of endothelin–1 in the pathogenesis of coronary vasospasm," *J. Cardiovas. Pharmacol. 13*: Suppl. 5, S132–S142 (1989).

Lerman et al., "Circulating and tissue endothelin immunoreactivity in advanced atherosclerosis," *New Engl. J. Med. 325*: 997–1001 (1991).

LexPat Record of U.S. Patent No. 5,464,853.

Maemura et al., "Gene expression of endothelin isoforms and receptors in endothelin–1 knockout mice," *J. Cardiovasc. Pharmacol. 26 (Suppl. 3)*: S17–S21 (1995).

Maggi et al., "Potent contractile effect of endothelin in isolated guinea–pig airways," *Eur. J. Pharmacol. 160*: 179–182 (1989).

Martin et al., "Differential effects of the mixed $ET_A/ET_B$–receptor antagonist bosentan on endothelin–induced bronchoconstriction, vasoconstriction and prostacylcin release," *Naunyn Schmiedebergs Arch. Pharmacol. 362*: 128–136 (2000).

Miyata et al., "WS–7338, new endothelin receptor antagonists isolated from Streptomyces sp. No. 7338. I. Taxonomy, fermentation, isolation, physico–chemical properties and biological activities," *J. Antibiot. (Tokyo) 45*: 74–82 (1992).

Miyata et al., "WS–7338, new endothelin receptor antagonists isolated from Streptomyces sp. No. 7338. II. Biological characterization and pharmacological characterization of WS–7338 B," *J. Antibiot. (Tokyo)* 45: 83–87 (1992).

Miyata et al. "WS–7338, new endothelin receptor antagonists isolated from Streptomyces sp. No. 7338,. III. Structures of WS–7338 A, B, C and D and total synthesis of WS–7338 B," *J. Antibiot. (Tokyo)* 45: 788–791 (1992).

Miyata et al., "WS009 A and B, new endothelin receptor antagonists isolated from Streptomyces sp. No. 89009. I. Taxonomy, fermentation, isolation, physico–chemical properties and biological activities," *J. Antibiot. (Tokyo)* 45: 1029–1040 (1992).

Miyata et al., "WS009 A and B, new endothelin receptor antagonists isolated from Streptomyces sp. No. 89009. II. Biological characterization and pharmacological characterization of WS009 A and B," *J. Antibiot. (Tokyo)* 45: 1041–1046 (1992).

Miyauchi et al., "Increase of the function of intra–cardiac autonomic nerves in isolated atria of swim–trained rats: study by the intra–cardiac nerve stimulation," *Jpn. J. Pharmacol.* 58: 279 (1992).

Moreau and Dao, "Endothelin receptor antagonists: novel agents for the treatment of hypertension?" *Expert Opin. Investig. Drugs* 8: 1807–1821 (1999).

Morel et al., "Increased plasma and pulmonary lymph levels of endothelin during endotoxin shock," *Eur. J. Pharmacol.* 167: 427–428 (1989).

Murugesan et al., "Biphenylsulfonamide endothelin receptor antagonists. 2. Discovery of 4+–oxazolyl biphenylsulfonamides as a new class of potent, highly selective ET(A) antagonists," *J. Med. Chem.* 43: 3111–3117 (2000).

Nakajima et al., "Endothelin–binding inhibitors, BE–18257A and BE–18257B II. Structure determination," *J. Antibiot. (Tokyo)* 44: 1348–1356 (1991).

Nirei et al., "An endothelin ETA receptor antagonist, FR139317, Amerliorates cerebral vaspasom in dogs," *Life Sci.* 52: 1869–1874 (1993).

Nishikibe et al., "Antihypertensive effect of a newly synthesized endothelin antagonist, BQ–123, in a genetic hypertensive model," *Life Sci.* 52: 717–724 (1993).

Nogrady et al., "4–pro–drugs and soft drugs," *Medicinal Chemistry A Biochemical Approach*, pp. 388–392 (1985).

Official Gazette Notice, Jul. 7, 1998, "Adverse Decisions in Interference," Interference No. 103,876.

Ohashi et al., "Asterric acid, a new endothelin binding inhibitor," *J. Antibiot. (Tokyo)* 45: 1684–1685 (1992).

Ormsbee and Ryan, "Production of hypertension with desoxycorticosterone actetate–impregnated silicone rubber implants," *J. Pharm. Sci.* 62: 255–257 (1973).

Palmer et al., "Nitric oxide release accounts for the biological activity of endothelin–derived relaxing factor," *Nature* 327: 524–526 (1987).

Panek et al., "Endothelin and structurally related analogs distinguish between endothelin receptor subtypes," *Biochem Biophys. Res. Commun.* 183: 566–571 (1992).

Panek et al., "Importance of secondary structure for endothelin binding and functional activity," *Biochem. Biophys. Res. Commun.* 183: 572–576 (1992).

Patt et al., "Butenolide endothelin antagonists with improved aqueous solubility," *J. Med. Chem.* 42: 2162–2168 (1999).

Patt et al., "Structure–activity relationships in a series of orally active gamma–hydroxy butenolide endothelin antagonists," *J. Med. Chem.* 40: 1063–1074 (1997).

Press Release, Texas Biotechnology Corporation, Antihypertensive effects of prolonged treatment with oral TBC11251NAa, a novel selective ETa endothelin receptor antagonist, in spontaneously hypertensive hamsters, Oct. 14, 1999, located at http://www.tbc.com/.

Press Release, Texas Biotechnology Corporation, Endothelin antagonism inhibits pulmonary vascular remodeling in the hypoxic piglet, Oct. 14, 1999, located at http://www.tbc.com/.

Press Release, Texas Biotechnology Corporation, Evaluation of novel, highly selective ETa receptor antagonists in hypoxia–induced pulmonary hypertension, Oct. 14, 1999, located at http://www.tbc.com/.

Press Release, Texas Biotechnology Corporation, Discovery of potent, orally available, ETa selective endothelin antagonists: TBC3214 and TBC3711, Oct. 14, 1999, located at http://www.tbc.com/.

Press Release, Texas Biotechnology Corporation, U.S. FDA Informed Texas Biotechnology of a Two Day Extension to the Official Review of NOVASTAN® NDA; New Date is Feb. 14, 2000; Delay Due to Inclement Weather Conditions in Jan., (available online at http://www.prnewswire.com/cgi–bin/stories.pl?ACCT = 105&STORY = /www/story/02–14–2000/0001140825 on Jun. 4, 2001).

Press Release, Texas Biotechnology Corporation, U.S. FDA Issues Approvable Letter to Texas Biotechnology for NOVASTAN® as Anticoagulant Drug for Prophlaxis or Treatment of Thrombosis in Patients with Heparin–Induced Thrombocytopenia (HIT), Feb. 22, 2000 (available online at http://www.prnewswire.com/cgi–bin/stories.pl?ACCT = 105&STORY = /www/story/02–22–2000/0001146181 on Jun. 4, 2001).

Press Release, Texas Biotechnology Corporation, Pivotal Phase III Clinical Trial Results for NOVASTAN® Presented at the American College of Cardiology Annual Meeting, Mar. 13, 2000 (available online at http://www.prnewswire-.com/cgi–bin/stories/pl?ACCT = 105&STORY = /www/story/03–13–2000/0001163517 on Jun. 4, 2001).

Press Release, Texas Biotechnology Corporation, ICOS and Texas Biotechnology Establish Joint Venture to Develop and Commercialize Endothelin Antagonists, Houston TX and Bothell, WA, Jun. 6, 2000 (available online at http://www.prnewswire.com/cgi–bin/stories.pl?ACCT = 105&STORY = /www.story/06–06–2000/0001236814 on Jun. 4, 2001).

Press Release, Texas Biotechnology Corporation, SmithKline Beecham and Texas Biotechnology Announces ARGATROBAN®'s Approval for the Prevention or Treatment of Thrombosis in Heparin–Induced Thrombocytopenia, Philadelphia, PA, Jun. 30, 2000 (available online at http://www.prenewswire.com/cgi–bin/stories.pl?ACCT = 105&STORY = /www/story/06–30–2000/0001256750 on Jun. 4, 2001).

Press Release, Texas Biotechnology Corporation, Schering–Plough and Texas Biotechnology From Alliance to Discover, Develop VLA–4 Antagonist Drugs to Treat Asthma, Madison, NJ and Houston, TX, Jul. 10, 2000 (available online at http://www.prnewswire.com/cgi/bin/stories.pl?ACCT = 105&STORY = /www.story/07–10–2000/0001261186 on Jun. 4, 2001).

Press Release, Texas Biotechnology Corporation, Update to Stockholders: SmithKline Beecham to Market Texas Biotechnologh's Anticoagulant Drug as ARGATROBAN®, Houston, TX, Sep. 22, 2000 (available online at http://www.prnewswire.com/cgi–bin/stories/pl?ACCT = 105&STORY = /www/story/09–22–2000/0001320235 on Jun. 4, 2001).

Press Release, Texas Biotechnology Corporation, Results of Open Label Studies with SITAXSENTAN® to be Presented at the American Heart Association Meeting, Houston, TX, Nov. 10, 2000 (available online at http://www.prnewswire.com/cgi–bin/stories.pl?ACCT = 105&STORY = /www/story/11–10–2000/0001362982 on Jun. 4, 2001).

Press Release, Texas Biotechnology Corporation,ICOS and Texas Biotechnology Initiate Human Testing with TBC3711, a Second Highly Selective Endothelin A Receptor Antagonist, Houston, TX and Bothell, WA, Dec. 20, 2000 (available online at http://www.prnewswire.com/cgi–bin/stories.pl?ACCT = 105&STORY = /www/story/10–16–2001/0001405137 in Jun. 4, 2001).

Raju et al., "Search for surrogates: a study of endothelin receptor antagonist structure activity relationships," *Bioorganic Medicinal Chem. LETT.* 7: 933–938 (1997).

Raju et al., "Amide bond surrogates: a study in thiophene-sulfonamide based endothelin receptor antagonists," *Bioorganic Medicinal Chem. LETT.* 7: 939–944 (1997).

Raju et al., "Thiophenesulfonamides as endothelin receptor antagonists," *Bioorganic Medicinal Chem. LETT.* 6: 2651–2656 (1996).

Ray et al., "Circulating endothelin in acute ischaemic syndromes," *Br. Heart J.* 67: 383–386 (1992).

Remuzzi et al., "Understanding the nature of renal disease progression," *Kidney Int.* 51: 2–15 (1997).

Roux et al., "Endothelin antagonism with bosentan: a review of potential applications," *J. Mol. Med.* 77: 364–376 (1999).

Saida et al., "A novel peptide, vasoactive intestinal contractor, of a new (endothelin) peptide family. Moleclar cloning, expression, and biological activity," *J. Biol. Chem.* 264: 14613–14616 (1989).

Saito et al., "Application of monoclonal antibodies for endothelin to hypertensive research," *Hypertension 15 (6 Pt. 2)*: 734–738 (1990).

Sakurai et al., "Cloning of a cDNA encoding a non–isopeptide–selective subtype of the endothelin receptor," *Nature* 348: 732–735 (1990).

Salamoussa et al., "The contractile effects of endothelins on the smooth muscle of the rat prostate gland," *Eur. J. Pharmacol.* 403: 139–145 (2000).

Sam and Colucci, "Role of endothelin–1 in myocardial failure," *Proc. Assoc. Am. Physicians 111*: 417–422 (1999).

Sanjay et al., "Does PTCA increase circulating endothelin level in Man?" *Circulating* 84: (Suppl. 4): 726 (1991).

Sawaki et al., "Chronic effects of an orally active selective endothelin–B–receptor antagonist in experimental congestive heart failure," *J. Cardiovasc. Pharmacol.* 36 (5 Suppl. 1): S323–S326 (2000).

Schvartz et al., "Bovine cerebellum endothelin receptor: solubilization and identification," *Endocrinology* 126: 3218–3222 (1990).

Schvartz et al., "Identification of a single binding protein for endothelin–1 and endothelin–3 in bovine cerebellum membranes," *Endocrinology* 128: 126–130 (1991).

Schvartz et al., "Identification of endothelin receptors by chemical cross–linking," *Endocrinology* 126: 1829–1833 (1990).

Shichiri et al., "Postural change and volume expansion affect plasma endothelin levels," *JAMA* 263: 661 (1990).

Shindo et al., "Upregulation of endothelin–1 and adrenomedullin gene expression in the mouse endotoxin shock model," *J. Cardiovasc. Pharmacol.* 31 (Suppl. 1): S541–S544 (1998).

Simonson and Dunn, "Endothelin–1 stimulates contraction of rat glomerular mesangial cells and potentiates β–Adrenergic–mediated cyclic adenosine monophosphate accumulation," *J. Clin. Invest.* 85: 790–797 (1990).

Spinella et al., "Design and synthesis of a specific endothelin 1 antagonists: effects on pulmonary vasoconstriction," *Proc. Natl. Acad. Sci. USA* 88: 7443–7446 (1991).

Spokes et al., "Studies with endothelin–3 and endothelin–1 on rat blood pressure and isolated tissues: evidence for multiple endothelin receptor types," *J. Cardiovasc. Pharmacol.* 12 (Suppl. 5): S191–S192 (1989).

Stein et al., "Discovery and structure–activity relationships of sulfonamide ETA–selective antagonists," *J. Med. Chem.* 38: 1344–1354 (1995).

Stein et al., "The Discovery of Sulfonamide Endothelin Antagonists and the Development of the Orally Active $ET_A$–Antagonist 5–(Dimethylamino)–N–(3, 4–dimethyl–5–isoxazolyl)–1–naphthalenesulfonamide," *J. Med. Chem.* 37: 329–331 (1994).

Stewart et al., "Increased plasma endothelin–1 in pulmonary hypertension: marker or mediator of disease?" *Ann. Int. Med.* 114: 464–469 (1991).

Suresh et al., "New developments in heart failure: role of endothelin and the use of endothelin receptor antagonists," *J. Card. Fail.* 6: 359–368 (2000).

Sutsch and Kiowski, "Endothelin and endothelin receptor antagonism in heart failure," *J. Cardiovasc. Pharmacol.* 35 (4 Suppl. 2): S69–S73 (2000).

Tahara et al., "Circulating immunoreactive endothelin in patients undergoing percutaneous transluminal coronary angioplasty," *Metab. Clin. Exp.* 40: 1235–1237 (1991).

Takayanagi et al., "Multiple subtypes of endothelin recpetors in porcine tissues: characteriation by ligand binding, affinity labeling and regional distribution," *Regul. Pept.* 32: 23–37 (1991).

Takayanagi et al., "Presence of non–selective type of endothelin receptor on vascular endothelium and its linkage to vasodilation," *FEBS Lett.* 282: 103–106 (1991).

Takayanagi et al., "Regional distribution of endothelin receptor in porcine cardiovascular tissues," *Regul. Pept.* 27: 247–255 (1990).

Texas Biotechnology Receives First Patent Issued For New Class of Cardiovascular Drugs, Houston, TX, Dec. 6, 1995, *For Immediate Release* (available at http://www.tbc.com/PR120695.HTM on Sep. 5, 1997).

Texas Biotechnology Reports Endothelin A Receptor Antagonist and VCAM/VLA–4 Inhibitor Patents, Houston, TX, May 16, 1996, *For Immediate Release* (available at http://www.tbc.com/PR051696.HTM on Sep. 5, 1997).

Texas Biotechnology Announces Initiation of Phase 1 Clinical Trial For TBC 11251 To Treat Congestive Heart Failure, Houston, TX, Nov. 13, 1996, *For Immediate Release* (available at http://www.tbc.com/PR111396.HTM on Sep. 5, 1997).

Texas Biotechnology Announces Initiation of Phase 1 Clinical Trial For TBC 1269 To Treat Asthma, Houston, TX, Jan. 21, 1997, *For Immediate Release* (available at http://www.tbc.com/PR012197.HTM on Sep. 5, 1997).

Texas Biotechnology Announces Initiation of Phase I Clinical Trial for TBC 11251 To Treat Congestive Heart Failure, Houston, TX, Nov. 13, 1996, *For Immediate Release* (available at http://www.tbc.com/press/pr111396.html on Jan. 27, 1999).

Texas Biotechnology Reports Endothelin a Receptor Antagonist and VCAM/VLA–4 Inhibitor Patens, Houston, TX, Mary 16, 1996, *For Immediate Release* (available at http://www.tbc.com/press/pr051696.html on Jan. 27, 1999).

Texas Biotechnology Receives First Patent Issued For New Class of Cardiovascular Drugs, Houston, TX, Dec. 6, 1995, *For Immediate Release* (available at http://www.tbc.com/press/pr120695.html on Jan. 27, 1999).

Texas Biotechnology Announces Initiation of Phase I Clinical Trial For TBC 1269 To Treat Asthma, Houston, TX, Jan. 21, 1997, *For Immediate Release* (available at http://www.tbc.com/press/pr012197.html on Jan. 27, 1999).

Texas Biotechnology Presents Clinical Results on its Endothelin A Receptor Antagonist, TBC11251, at HA Sessions, Houston, TX, Nov. 10, 1998, *For Immediate Release* (available at http://www.tbc.com/press/pr111098.html on Jan. 28, 1999).

Texas Biotechnology Resubmits Novastan® NDA, Houston, TX, Mar. 22, 1999, *For Immediate Release* (available at http://www.tbc.com/press/pr032299.html on May 27, 1999).

Texas Biotechnology Announces Positive Data on Initial Phase IIA Asthma Study, Houston, TX, Sep. 9, 1998, *For Immediate Release* (available at http://www.tbc.com/press/pr090998.html on Jan. 28, 1999).

Texas Biotechnology Reports Additional Positive Phase IIA Trial Results in Congestive Heart Failure, Houston, TX, Jul. 21, 1998, *For Immediate Release* (available at http://www.tbc.com/press/pr072298.html on Jan. 28, 1999).

Texas Biotechnology Updates Stockholders at 1998 Annual Meeting, Houston, TX, Jun. 9, 1998, *For Immediate Release* (available at http://www.tbc.com/press/pr060998.html on Jan. 28, 1999).

Texas Biotechnology's Submission of Additional Novastan® Data Extends NDA Review by FDA, Houston, TX, Jan. 23, 1998, *For Immediate Release* (available at http://www.tbc.com/press/pr012398.html on Jan. 27, 1999).

Texas Biotechnology Initiates Phase IIA Trial For Novel Anti–Inflammatory To Treat Asthma, Houston, TX, Oct. 22, 1997, *For Immediate Release* (available at http://www.tbc.com/press/pr102297.html on Jan. 28, 1999).

Texas Biotechnology's Novastan® NDA Granted Priority Review Status By The FDA, Houston, TX, Sep. 4, 1997, *For Immediate Release* (available at http://www.tbc.com/presspr090497.html on Jan. 28, 1999).

Texas Biotechnology and Smithkline Beecham Form Alliance to Market And Develop Novastan® (argatroban) In North American, FDA Filing for New Thrombin Inhibitor to Be Completed This Month, Houston, TX and Philadelphia, PA, Aug. 6, 1997, *For Immediate Release* (available at http://www.tbc.com/press/pr080697.html on Jan. 28, 1999).

Texas Biotechnology Initiates Filing of New Drug Appliation For Novastan®, Houston, TX, Jul. 2, 1997, *For Immediate Release* (available at http://www.tbc.com/press/pr070297.html on Jan. 28, 1999).

Texas Biotechnology Announces Promising Clinical Updates on Phase II Trials of Novastan® In Acutte MI, Houston, TX, Mar. 17, 1997, *For Immediate Release* (available at http://www.tbc.com/press/pr031797.html on Jan. 28, 1999).

Texas Biotechnology Announces Results of Phase III Novstan® Clinical Study In Patients With Hit and HITTS, Houston, TX, May 22, 1997, *For Immediate Release* (available at http://www.tbc.com/press/pr052297.html on Jan. 28, 1999).

Texas Biotechnology Announces Results of Phase III Clinical Study In PTCA Patients With HIT, Houston, TX, *For Immediate Release* (available at http://www.tbc.com/press/pr041797.html on Jan. 29, 1999).

Texas Biotechnology Received U.S. Patents For New Class of Cardiovascular Therapeutics, Endothelin A Receptor Antagonists, Houston, TX, Jan. 22, 1997, *For Immediate Release* (available at http://www.tcb.com/press/pr0122297.html on Jan. 28, 1999).

Texas Biotechnology Completes Phase I Safety Trial For Oral Endothelin Antagonist, Houston, TX, Dec. 11, 1997, *For Immediate Release* (available at http://www.tbc.com/press/pr121197.html on Jan. 28, 1999).

Texas Biotechnology And Loyola University Medical Center Sponsor International Symposium On Heparin–Induced Thrombocytopenia And New Thrombin Inhibitors, Houston, TX, Dec. 6, 1996, *For Immediate Release* (available at http://www.tbc.com/press/pr120696.html on Jan. 28, 1999).

Texas Biotechnology Announces Clinical Agreements With Synthelabo, Houston, TX, Jan. 22, 1996, *For Immediate Release* (available at http://www.tbc.com/press/pr012296.html on Jan. 28, 1999).

Texas Biotechnology Reports Phase II Clinical Trial Results, Houston, TX, Feb. 21, 1996, *For Immediate Release* (available at http://www.tbc.com/press/pr022196.html on Jan. 28, 1999).

Texas Biotechnology Initiates Phase III Trial For Novastan® in Coronary Interventional Procedures, Houston, TX, May 9, 1996, *For Immediate Release* (available at http://www.tbc.com/press/pr050996.html on Jan. 28, 1999).

Texas Biotechnology Signs Additional Clinical Development Agreement With Synthelabo For Novastan®, Houston, TX, Jun. 25, 1996, *For Immediate Release* (available at http://www.tbc.com/press/pr062596.html on Jan. 28, 1999).

Texas Biotechnology Announces Preliminary Phase II Results of Novastan In Acute Myocardial Infarction, Houston, TX, Oct. 21, 1996, *For Immediate Release* (available at http://www.tbc.com/press/pr102196.html on Jan. 28, 1999).

Texas Biotechnology Reports Partner, Mitsubishi Chemical, Receives Stroke Indication for Novastan® In Japan, Houston, TX Jun. 18, 1996, *For Immediate Release* ( available at http://www.tbc.com/press/pr061896.html on Jan. 28, 1999).

Texas Biotechnology Presents Clinical Results On Its Endothelin A Receptor Antagonist, TBC11251, at AHA Sessions, Houston, TX, Nov. 10, 1998, *For Immediate Release* (available at http://www.tbc.com/press/pr061896.html on May 27, 1999).

Texas Biotechnology Resubmits NOVASTAN® NDA, Houston, TX, Mar. 22, 1999, *For Immediate Release*, (available at http://www.prenewswire.com/cgi–bin/stories.pl?ACCT = 105&STORY = /www/story/06–28–1999/0000971784 on Jun. 4, 2001).

Texas Biotechnology Submits Corrected Amendment to the Novastan® New Drug Application, Houston, TX, August 23, 1999, *For Immediate Release* (available at http://www-.prnewswire.com/cgi–bin/stories/pl?ACCT = 105&STORY = /www/story/08–23–1999/0001008148 on Jun. 4, 2001).

Texas Biotechnology Reports Progress on Endothelin A Receptor Antagonist Program, Houston, TX, Oct. 14, 1999, *For Immediate Release* (available online at http://www.prnewswire.com/cgi–bin/stories/pl?ACCT = 105&STORY = /www/story/10–14–1999/0001043781 on Jun. 4, 2001).

Texas Biotechnology Announces Discovery of Potent, Orally Available, ETa Selective Endothelin Antagonists: TBC3214 and TBC3711,Houston, TX, *For Immediate Release* (available online at http://www.prnewswire.com/cgi–bin/stories.pl?ACCT = 105&STORY = /www/story/10–14–1999/0001043928 on Jun. 4, 2001).

Texas Biotechnology Announces First Quarter Financial Results and Updates Shareholders on Key Corporate Programs, Houston, TX, May 15, 2000 (available online at http://www.prnewswire.com/cgi–bin/stories.pl?ACCT = 105&STORY = /www/story/05–15–2000/0001218108 on Jun. 4, 2001).

Texas Biotechnology and SmithKline Beecham File Supplemental New Drug Appliction of AGRATROBAN for HIT Patients Undergoing Percutaneous Coronary Interventions, Houston, TX, Dec. 21, 2000 (available online at http://www/prnewswire.com/cgi–bin/stories.pl?ACCT = 105&STORY = /www.story/12–21–2000/0001391596 on Jun. 4, 2001).

Tomita et al., "Plasma endothelin levels in patients with acute renal failure," *N. Engl. J. Med. 321*: 1127 (1989).

Uhlmann et al., "Endothelin receptor blockade as a therapeutic strategy in ameliorating postischemic damage to the liver microcirculation," *J. Cardiovasc. Pharmacol. 36 (3 Suppl. 1)*: S351–S353 (2000).

Vanhoutte et al., "Modulation of vascular smooth muscle contraction by the endothelium," *Annual Rev. Physiol. 48*: 307–320 (1986).

Warner et al., "Endothelin receptor antagonists: actions and rationale for their development," *Biochem. Pharmacol. 48*: 625–635 (1994).

Wu et al., "Discovery of TBC11251, a potent, long acting, orally active endothelin receptor–A selective antagonist," *J. Medicinal Chem. 40*: 1690–1697 (1997).

Wu et al., "Endothelin antagonists: substituted mesitylcarboxamides with high potency and selectivity for ET(A) receptors," *J. Med. Chem. 42*: 4485–4499 (1999).

Wu et al., "Structure–activity relationships of N–2–aryl–3–(isoxazolylsulfamoyl)–2–thiophenecarboxamides as selective endothelin receptor–A antagonists," *J. Medicinal Chem. 40*: 1682–1689 (1997).

Wu–Wong et al., "Endothelin receptor antagonists: effects of serum albumin on potency and comparison of pharmacological characteristics," *J. Pharmacol. Exp. Ther.* 281: 791–798 (1997).

Yanagisiawa et al., "A novel potent vasoconstrictor peptide produced by vascular andothelial cells," *Nature 332*: 411–415 (1990).

Yasuda, et al., "Circulating immunoreactive endothelin in ischemic heart disease," *A. Heart J. 119*: 801–806 (1990).

Zamora, et al., "Serum endothelin–1 concentrations and cold provocation in primary Raynaud's phenomenon," *Lancet 336*: 1144–1147 (1990).

BENZENESULFONAMIDES AND THE USE THEREOF TO MODULATE THE ACTIVITY OF ENDOTHELIN

RELATED APPLICATIONS

This application is a continuation of U.S. application Ser. No. 09/439,802 filed Nov. 12, 1999, allowed which is a continuation of U.S. application Ser. No. 08/730,633 filed Dec. 6, 1996, now U.S. Pat. No. 6,030,991, which is a continuation of U.S. application Ser. No. 08/416,199 filed Apr. 4, 1995, ABN which is a continuation-in-part of U.S. application Ser. No. 08/247,072, filed May 20, 1994, now U.S. Pat. No. 5,571,821 and a continuation in part of U.S. application Ser. No. 08/222,287 filed Apr. 5, 1994, now U.S. Pat. No. 5,591,761 and a continuation in part of U.S. application Ser. No. 08/142,159 filed Oct. 21, 1993, now U.S. Pat. No. 5,464,853, and a continuation in part of U.S. application Ser. No. 08/142,552 filed Oct. 21, 1993, now U.S. Pat. No. 5,514,691 and a continuation in part of U.S. application Ser. No. 08/100,565 filed Jul. 30, 1993, now abandoned; and a continuation in part of U.S. application Ser. No. 08/100,125 filed Jul. 30, 1993, now abandoned; and a continuation in part of U.S. application Ser. No. 08/065,202, filed May 20, 1993, now abandoned.

The subject matter of each of U.S. application Ser. Nos. 09/439,802, 08/730,633, 08/416,199, 08/247,072, 08/222,287, 08/142,159, 08/142,552, 08/142,631, 08/100,565, 08/100,125 and 08/065,202 is incorporated herein in its entirety.

FIELD OF THE INVENTION

The present invention relates to the compounds that modulate the activity of the endothelin family of peptides. In particular, the invention relates to the use of sulfonamides and sulfonamide pro-drugs as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et aL (1988) *Nature* 332: 411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, eq., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$,$Leu^7$) endothelin-1 and endothelin-3 is ($Thr^2$,$Phe^4$,$Thr^5$,$Tyr^6$,$Lys^7$,$Tyr^{14}$) endothelin-1. These peptides are, thus, highly conserved at the C-terminal ends.

Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}$=$4\times10^{-10}$ M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2$–$6\times10^{-10}$ M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states (see, eq, International PCT Application WO 94/27979, and U.S. Pat. No. 5,382,569, which disclosures are herein incorporated in their entirety by reference). Endothelin-1 plasma levels in healthy individuals, as measured by radio-immunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels are as high as 35 pg/mi have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Elevated levels of endothelin have also been measured in patients suffering from ischemic heart disease (Yasuda et al. (1990) Amer. Heart J. 119:801–806, Ray et al. (1992) *Br. Heart J.* 67:383–386). Circulating and tissue endothelin immunoreactivity is increased more than twofold in patients with advanced atherosclerosis (Lerman et al. (1991) *New Engl. J. Med.* 325:997–1001). Increased endothelin immunoreactivity has also been associated with Buerger's disease (Kanno et al. (1990) *J. Amer. Med. Assoc.* 264:2868) and Raynaud's phenomenon (Zamora et al. (1990) *Lancet* 336 1144–1147). Increased circulating endothelin levels were observed in patients who underwent percutaneous transluminal coronary angioplasty (PTCA) (Tahara et al. (1991) *Metab. Clin. Exp.* 40:1235–1237; Sanjay et al. (1991) *Circulation* 84(*Suppl.* 4):726), and in individuals (Miyauchi et al. (1992) *Jpn. J. Pharmacol.*58:279P; Stewart et al. (1991) *Ann.Internal Medicine* 114:464–469) with pulmonary hypertension. Thus, there is clinical human data supporting the states.

Because endothelin is associated with certain disease states and is implicated in numerous physiological effects, compounds that can interfere with or potentiate endothelin-associated activities, such as endothelin-receptor interaction and vasoconstrictor activity, are of interest. Compounds that exhibit endothelin antagonistic activity have been identified. For example, a fermentation product of *Streptomyces misakiensis*, designated BE-18257B, has been identified as an $ET_A$ receptor antagonist. BE-18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner ($IC_{50}$ 1.4 µM in aortic smooth muscle, 0.8 µM in ventricle membranes and 0.5 µM in cultured aortic smooth muscle cells), but fails to inhibit binding to receptors in tissues in which $ET_B$ receptors predominate at concentrations up to 100 µM. Cyclic pentapeptides related to BE-18257B, such as cyclo(D-Asp-Pro-D-Val-Leu-D-Trp) (BQ-123), have been synthesized and shown to exhibit activity as $ET_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors. Other peptide and non-peptidic $ET_A$ antagonists have been identified (see, e.g., U.S. Pat. Nos. 5,352,800, 5,334,598, 5,352,659, 5,248,807, 5,240,910, 5,198,548, 5,187,195, 5,082,838). These include other cyclic peptides, acyltripeptides, hexapeptide analogs, certain anthraquinone derivatives, indanecarboxylic acids, certain N-pyrimidinylbenzenesulfonamides, certain benzenesulfonamides, and certain naphthalenesulfonamides (Nakajima et al. (1991)*J. Antibiot.* 44:1348–1356; Miyata et al. (1992)*J. Antibiot.* 45:74–8; Ishikawa et al. (1992)*J.Med. Chem.* 35:2139–2142; U.S. Pat. No. 5,114,918 to Ishikawa et al.; EP A1 0 569 193; EP A1 0 558 258; EP A1 0 436 189 to BANYU PHARMACEUTICAL CO., LTD (Oct. 7, 1991); Canadian Patent Application 2,067,288; Canadian Patent Application 2,071,193; U.S. Pat. No. 5,208,243; U.S. Pat. No. 5,270,313; Cody et al. (1993) *Med. Chem. Res.* 3:154–162; Miyata et al. (1992) *J. Antibiot* 45:1041–1046; Miyata et al. (1992) *J. Antibiot* 45:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO 93/08799; Nishikibe et al. (1993) *Life Sci.* 52:717–724; and Benigni et al. (1993) *Kidney Int.* 44:440–444). In general, the identified compounds have activities in in vitro assays as $ET_A$ antagonists at concentrations on the order of about 50–100 µM or less. A number of such compounds have also been shown to possess activity in in vivo animal models. Very few, if any, selective $ET_B$ antagonists have been identified.

Endothelin Antagonists and Agonists as Therapeutic Agents

It has been recognized that compounds that exhibit activity at $IC_{50}$ or $EC_{50}$ concentrations on the order of $10^{-4}$ or lower in standard in vitro assays that assess endothelin antagonist or agonist activity have pharmacological utility (see, eg., U.S. Pat. Nos. 5,352,800, 5,334,598, 5,352,659, 5,248,807, 5,240,910, 5,198,548, 5,187,195, 5,082,838). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated.

Thus, in view of the numerous physiological effects of endothelin and its association with certain diseases, endothelin is believed to play a critical role in these pathophysiological conditions (see, em, Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(*Suppl.* 5): S13–S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions.

To aid in gaining further understanding of and to develop treatments for endothelin-mediated or related disorders, there is a need to identify compounds that modulate or alter endothelin activity. Identification of compounds that modulate endothelin activity, such as compounds that act as specific antagonists or agonists, may not only aid in elucidating the function of endothelin, but may yield in therapeutically useful compounds. In particular, compounds that specifically interfere with the interaction of endothelin peptides with $ET_A$, $ET_B$ or other receptors should be useful in identifying essential characteristics of endothelin peptides, should aid in the design of therapeutic agents, and may be useful as disease specific therapeutic agents.

Therefore, it is an object herein to provide compounds that have the ability to modulate the biological activity of one or more of the endothelin isopeptides. It is another object to provide compounds that have use as specific endothelin antagonists. It is of particular interest herein to provide compounds that selectively interact with $ET_B$ receptors. It is also an object to use compounds that specifically interact with or inhibit the interaction of endothelin peptides with $ET_A$ or $ET_B$ receptors. Such compounds should be useful as therapeutic agents for the treatment of endothelin-mediated diseases and disorders and also for the identification of endothelin receptor subtypes.

SUMMARY OF THE INVENTION

Sulfonamides and methods for modulating the interaction of an endothelin peptide with $ET_A$ and/or $ET_B$ receptors are provided. In particular, sulfonamides and methods for inhibiting the binding of an endothelin peptide to $ET_A$ or $ET_B$ receptors are provided. Sulfonamides that act as endothelin peptide agonists with respect to $ET_A$ or $ET_B$ receptors are also provided. Among the compounds provided herein are those that are particularly active as $ET_B$ antagonists.

The methods are effected by contacting endothelin receptors with one or more sulfonamides prior to, simultaneously with, or subsequent to contacting the receptors with an endothelin peptide. The sulfonamides are substituted or unsubstituted monocyclic or polycyclic aromatic or heteroaromatic sulfonamides, such as benzene sulfonamides, particularly biphenyl sulfonamides, naphthalene sulfonamides, and fused tricyclic ring sulfonamides.

The sulfonamides have formula I:

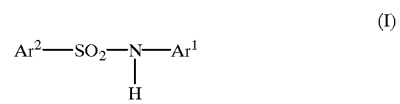

in which $Ar^1$ is a substituted or unsubstituted aryl group with one or more substituents, including an alkyl group, an aryl group, a substituted aryl group, a nitro group, an amino group or a halide or is an alkyl group. In particular, $Ar^1$ is alkyl or is a five or six membered substituted or unsubstituted aromatic or heteroaromatic rings, including, 3- or 5-isoxazolyl, thiazolyl such as 2-thiazolyl, pyrimidinyl such as 2-pyrimidinyl, pyridazinyl, and unsubstituted or substituted benzene groups, including aryloxy substituted benzene groups or is a bicyclic or tricyclic ring.

$Ar^2$ is any group such that the resulting sulfonamide inhibits binding by 50%, compared to binding in the absence of the sulfonamide, of an endothelin peptide to an endothelin receptor at a concentration of the sulfonamide of less than about 100 μM, except that $Ar^2$ is not phenyl, 2-biphenyl or naphthyl unless $R^1$ is a halide or higher alkyl or unless it is a biphenyl, other than a 2-biphenyl, and the substituent at the 2 (and/or 6 position)s on the phenyl linked to the sulfonamide is hydrogen.

$Ar^1$ is, in certain embodiments, selected from groups such as:

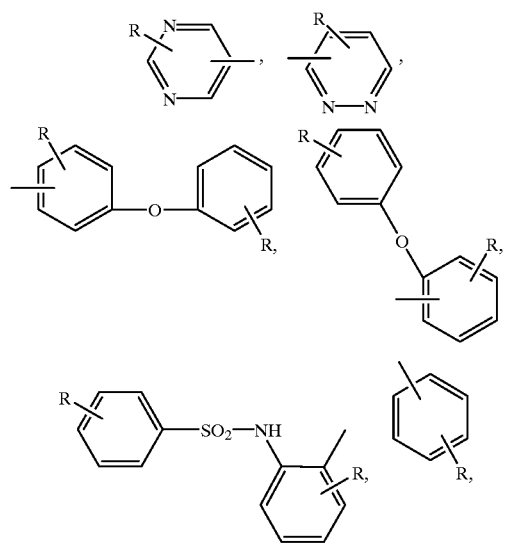

-continued

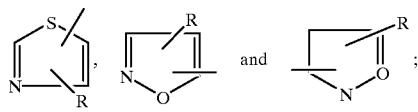

and R is selected from H, NH$_2$, halide, pseudohalide, alkyl alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and unsubstituted or substituted with any of the preceding groups, and straight or branched chains of from about 1 up to about 10–12 carbons, preferably, 1 to about 5 or 6 carbons. R is preferably H, NH$_2$, halide, CH$_3$, CH$_3$O or another aromatic group.

In the embodiments described in detail herein, Ar$^1$ is generally an isoxazole and the compounds are represented by the formulae II:

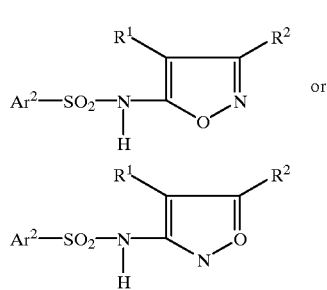

in which R$^1$ and R$^2$ are either (i), (ii) or (iii) as follows:
(i) R$^1$ and R$^2$ are each independently selected from H, NH$_2$, NO$_2$, halide, pseudohalide, alkyl, alkenyl, alkynyl, aryl, arylalkyl, heteroaryl, alkoxy, alkylamino, alkylthio, alkyloxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that R$^2$ is not halide or pseudohalide; or,
(ii) R$^1$ and R$^2$ together form —(CH$_2$)$_n$—, where n is 3 to 6; or,
(iii) R$^1$ and R$^2$ together form 1,3-butadienyl, and with the proviso that Ar$^2$ is not 2-biphenyl, naphthyl or phenyl, other than certain 3-biphenyls or 4-biphenyls, unless R$^1$ is a halide or higher (C$_8$–C$_{15}$, preferably C$_9$–C$_{13}$) alkyl. R$^1$ is more preferably bromide or chloride, methyl or ethyl or (C$_9$–C$_{13}$)alkyl. In the most active compounds provided herein, as evidenced by in vitro binding assays, R$^1$ is bromide or chloride or, in instances in which ET$_B$ selectivity is desired, C$_9$–C$_{13}$ alkyl.

In other embodiments herein, Ar$^1$ is pyridinyl, particularly N-3-pyridazinyl sulfonamides, in which the pyridazinyl group is unsubstituted or substituted with one or more substituents selected from R.

In the embodiments described in detail herein, Ar$^2$ is naphthyl, phenyl, including biphenyl or a group that is a derivative of or analog, as described below, of a biphenyl group, and Ar$^1$ is preferably N-(5-isoxazolyl) or N-(3-isoxazolyl) or N-pyridinyl, preferably N-3-pyridazinyl.

In the preferred compounds herein, R$^2$ is preferably, selected from among alkyl, lower alkenyl, lower alkynyl, lower haloalkyl, halide or H; and R$^1$ is halide, lower alkyl, or higher (C$_8$–C$_{15}$, preferably C$_9$–C$_{13}$) alkyl, except: (a) when Ar$^2$ is phenyl and R$^4$, R$^5$, R$^6$ and R$^7$ are hydrogen, R$^3$ is not, NO$_2$, NH$_2$ or lower alkyl, unless R$^1$ is higher alkyl; and (b) if Ar$^2$ is naphthyl or if Ar$^2$ is phenyl, or if Ar$^2$ is 2-biphenyl or if Ar$^2$ is 3-biphenyl in which R$^4$ and R$^5$ are other than hydrogen, then R$^1$ is halide or higher alkyl (C$_8$H$_{17}$—C$_{15}$H$_{29}$), preferably C$_9$H$_{17}$—C$_{13}$H$_{27}$).

In particular embodiments disclosed herein, Ar$^2$ is a group of formulae III:

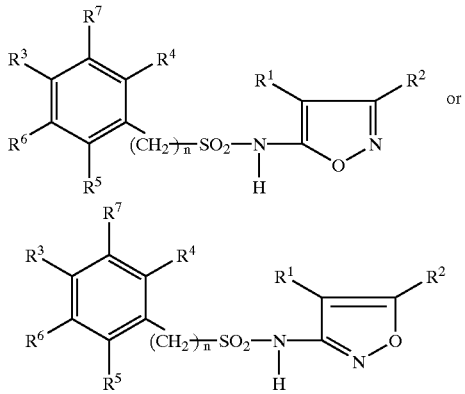

in which:
n is 0 to 10, preferably 0 to 3, more preferably 0 or 1, most preferably 0;
R$^3$, R$^4$, R$^5$, R$^6$, and R$^7$ are selected from (i), (ii), (iii), (iv) or (v) with the proviso that: (a) when Ar$^2$ is phenyl and R$^4$, R$^5$, R$^6$ and R$^7$ are hydrogen, R$^3$ is not NO$_2$, NH$_2$ or lower alkyl, unless R$^1$ is higher alkyl; (b) if Ar$^2$ is naphthyl or if Ar$^2$ is phenyl, or if Ar$^2$ is 2-biphenyl or if Ar$^2$ is 3-biphenyl in which R$^4$ and R$^5$ are other than hydrogen, then R$^1$ is halide or higher (C$_8$–C$_{15}$, preferably C$_9$–C$_{13}$) alkyl:
(i) R$^3$, R$^4$, R$^5$, R$^6$, and R$^7$ are each selected independently from among H, NHOH, NH$_2$, NO$_2$, N$_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; or, alternatively,
(ii) R$^4$ and R$^7$ together are substituted or unsubstituted 1,3-butadienyl, 4-dimethylamino-1,3-butadienyl, 1-chloro-1,3-butadienyl, 1-aza-1,3-butadienyl or 2-aza-1,3-butadienyl groups; and R$^3$, R$^5$ and R$^6$ are as defined in (i) above; or alternatively,
(iii) R$^7$ and R$^3$ together are substituted or unsubstituted 1,3-butadienyl, 4-dimethylamino-1,3-butadienyl, 1-chloro-1,3-butadienyl, 1-aza-1,3-butadienyl or 2-aza-1,3-butadienyl groups; and n, X, R$^4$, R$^5$ and R$^6$ are as defined in (i) above; or
(iv) R$^3$, R$^5$, and R$^7$ are H or as defined in (i); and R$^4$ and R$^6$ are each independently selected from alkyl, alkoxy, halide aminoalkyl, dialkylaminoalkyl, in which the alkyl and alkoxy groups contain from 1 to 10, preferably 1 to 6 carbons, and are straight or branched chains; or (v) any two of $R^3$, $R^4$, $R^5$, $R^6$, and $R^7$, which are each selected as in (i) form fused carbocyclic or heterocyclic rings.

Thus, in the compounds provided herein $Ar^2$ is selected from among phenyl, biphenyl, naphthyl, and bicyclic and tricyclic fused carbocyclic and heterocyclic rings, and other such groups.

Selected isoxazolyl-benzenesulfonamides and isoxazolyl-naphthalenesulfonamides in which the isoxazole is other than a 4-haloisoxazole are also provided. Such selected compounds, including N-isoxazolylbenzenesulfonamides and N-isoxazolyinaphthalenesulfonamides in which the substituent at the 4 position on the isoxazolyl group is higher alkyl, such as $C_9H_{19}$ to $C_{13}H_{27}$ are also provided. These compounds have enhanced $ET_B$ affinity compared to corresponding compounds in which the substituent at the 4 position is lower alkyl or other groups, such as pseudohalide, halide, alkylaryl, aryl, lower alkyl, carboxamide, alkoxy, and others.

In embodiments in which $Ar^2$ is biphenyl, one of $R^3$, $R^4$, $R^5$, $R^6$ and $R^7$ is phenyl, which is substituted or is unsubstituted with substituents such as $Z^1$–$Z^5$ in which each Z is independently selected from hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; and $R^{12}$ and $R^{16}$ are each independently selected from hydrogen, alkyl, alkenyl, alkynyl, aryl, alkylaryl, heterocycle, aralkyl, aralkoxy, cycloalkyl, cycloalkenyl or cycloalkynyl; and the others of $R^3$, $R^4$, $R^5$, $R^6$ and $R^7$ are each independently selected from among H, NHOH, $NH_2$, $NO_2$, $N_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; or, alternatively, with the proviso that: if $Ar^2$ is 2-biphenyl or if $Ar^2$ is 3-biphenyl in which $R^4$ and $R^5$ are other than hydrogen, then $R^1$ is halide or higher ($C_8$–$C_{15}$, preferably $C_9$–$C_{13}$) alkyl. In other embodiments, if $Ar^2$ is 4-biphenyl and $R^4$ and/or $R^5$ are other hydrogen, then $R^1$ is halide or higher ($C_8$–$C_{15}$, preferably $C_9$–$C_{13}$) alkyl.

Z is preferably selected from:

(i) hydrogen, OH, $NH_2$, $NO_2$, alkyl, haloalkyl, halide, pseudohalide, alkoxy, alkoxyalkyl, $NR^{11}$, in which $R^{11}$ is selected from among H, a straight or branched carbon chain, preferably containing 1 to 6, more preferably 1 to 3, carbons, halide, alkoxyalkyl, haloalkyl, S or O, or the like; or (ii) any two of $Z^1$–$Z^5$ together with the atoms to which each is attached form a carbon ring or heterocycle fused to the phenyl group. It is preferable that at least three or four of $Z^1$–$Z^5$ is hydrogen, and preferably the hydrogens are in the meta positions and ortho positions. Preferred positions for $Z^1$–$Z^5$, when not hydrogen, are the para position and/or ortho position.

In particular, $R^{11}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with any of hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH and CN.

In preferred embodiments herein, $R^3$ or $R^6$ or $R^7$ is phenyl. In more preferred embodiments, $R^3$ is phenyl, and $Z^2$–$Z^5$ are hydrogen or lower alkyl, preferably $C_{1-3}$ alkyl, and $Z^1$ is in the ortho, or para position, and is preferably lower alkyl, lower alkoxy, halo-lower alkyl or halide.

Compounds in which $Ar^2$ is a tricyclic carbocycle or heterocycle are also provided. In particular, preferred among these compounds are compounds of formula:

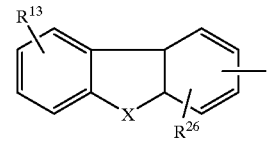

in which X is S, O, $NR^{14}$ in which $R^{14}$ like $R^{11}$, but selected independently from $R^{11}$, is aryl, hydrogen, or lower alkyl, preferably, a substituted or unsubstituted aryl, particularly phenyl, preferably unsubstituted or substituted with lower alkyl or halogen hydrogen or lower alkyl, in which the alkyl groups contain from 1–6 carbons, preferably 1–3 carbons, and are straight, branched or cyclic chains.

In the above compounds, the alkyl, alkynyl and alkenyl portions of each listed substituent are straight or branched chains or are cyclic, and preferably have from about 1 up to about 10 carbons; in more preferred embodiments they have from 1–6 carbons, and they can have fewer than 6 carbons. The aryl, carbocyclic, aromatic rings and heterocyclic groups can have from 3 to 16, generally, 3–7, more often 5–7 members in the rings, and may be single or fused rings. The ring size and carbon chain length are selected up to a size such that the resulting molecule binds to retains activity as an endothelin antagonist or agonist, such that the resulting compound inhibits binding by 50%, compared to binding in the absence of the sulfonamide, of an endothelin peptide to an endothelin receptor at a concentration of less than about 100 μM.

Of particular interest herein are compounds that inhibit binding of endothelin to $ET_B$ receptors at lower concentrations, preferably at least 2-fold, more preferably 3-fold, and most preferably at least 5- to 10-fold lower than they inhibit binding to $ET_A$ receptors.

Preferred compounds are $ET_B$ receptor selective or bind to $ET_B$ receptors with an $IC_{50}$ of less than about 1 μM.

Preferred compounds also include compounds that are $ET_B$ receptor selective or that competitively inhibit binding of endothelin-1 to $ET_B$ receptors at $IC_{50}$ concentrations of 1 μM (if measured at 4° C.; or 5–10 μM, if measured at 24° C.). In preferred compounds, generally $R^2$ is selected from among alkyl, lower alkenyl, lower alkynyl, lower haloalkyl, halide or H; and $R^1$ is halide or lower alkyl, and in preferred embodiments, $R^1$ is bromide or chloride.

Of the compounds described herein, those that inhibit or increase an endothelin-mediated activity by about 50% at concentrations of less than about 10 μM are preferred. More preferred are those that inhibit or increase an endothelin-mediated activity by about 50% at concentrations of less than about 1 μM, more preferably less than about 0.1 μM, even more preferably less than about 0.01 μM, and most preferably less than about 0.005 μM. The preferred $IC_{50}$ concentrations are set forth with reference to the in vitro assays exemplified herein. It is understood that these $IC_{50}$ concentrations vary from assay to assay. For example, it is noted that, as described below, the $IC_{50}$ concentration determined in the in vitro assays is a non-linear function of incubation temperature. The preferred values recited herein refer to the assays that are performed at 4° C. When the assays are performed at 24° C., somewhat higher (see, Table 1) $IC_{50}$ concentrations are observed. Accordingly, when the assay is performed at 24° C., the preferred $IC_{50}$ concentrations are about 10-fold higher.

Pharmaceutical compositions formulated for administration by an appropriate route and means containing effective concentrations of one or more of the compounds provided herein or pharmaceutically acceptable salts or acids thereof that deliver amounts effective for the treatment of bronchoconstrictive disorders, and other conditions that are in some manner mediated by an endothelin peptide or that involve bronchoconstriction or whose symptoms can be ameliorated by administration of an $ET_B$-specific endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for inhibiting binding of an endothelin peptide to an endothelin receptor are provided. These methods are practiced by contacting the receptor with one or more of the compounds provided herein simultaneously, prior to, or subsequent to contacting the receptor with an endothelin peptide.

Methods for treatment of endothelin-mediated disorders, including but not limited to, asthma, conditions that are in some manner mediated by an endothelin peptide that binds to $ET_B$ receptors, or for treatment of disorder that involves bronchoconstriction or that are ameliorated by administration of an $ET_B$ receptor endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including respiratory diseases and inflammatory diseases, including asthma, bronchio-constriction, and other diseases in which $ET_B$ receptor endothelin mediated physiological responses are implicated, by administering effective amounts of one or more of the compounds provided herein in pharmaceutically acceptable carriers are provided. Preferred methods of treatment are methods for treatment of hypertension and renal failure.

More preferred methods of treatment are those in which the compositions contain at least one compound that inhibits the interaction of an endothelin with $ET_B$ receptors at an $IC_{50}$ of less than about 10 μM, and preferably less than about 5 μM, more preferably less than about 1 μM, even more preferably less than 0.1 μM, and most preferably less than 0.05 μM Other preferred methods are those in which the compositions contain one or more compounds that is (are) $ET_B$ selective. Methods in which the compounds are $ET_B$ selective are for treatment of disorders, such as asthma, that require bronchodilation.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes, particularly $ET_B$ subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an $ET_B$ receptor with an $IC_{50}$ of less than about 10 μM, within the packaging material, and a label that indicates that the compound or salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Exemplary assays are set forth in the EXAMPLES. As noted above, the preferred $IC_{50}$ concentration ranges are set forth with reference to assays in which the test compound is incubated with the ET receptor-bearing cells at 4° C. Data presented for assays in which the incubation step is performed at the less preferred 24° C. are identified. It is understood that for purposes of comparison, these concentrations are somewhat higher than the concentrations determined at 4° C.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by In vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, e.g., Spokes et al. (1989) *J. Cardiovasc. Pharmacol.* 13(Suppl. 5):S191–S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein a sulfonamide that is $ET_A$ selective refers to sulfonamides that exhibit an $IC_{50}$ that is at least about 10-fold lower with respect to $ET_A$ receptors than $ET_B$ receptors.

As used herein, a sulfonamide that is $ET_B$ selective refers to sulfonamides that exhibit an $IC_{50}$ that is at least about 10-fold lower with respect to $ET_B$ receptors than $ET_A$ receptors.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392). For example, succinylsulfathiazole is a prodrug of 4-amino-N-(2-thiazolyl)benzenesulfonamide (sulfathiazole) that exhibits altered transport characteristics.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate and azide.

As used herein, lower alkyl, lower alkenyl, and lower alkynyl refer to carbon chains having less than about 6 carbons. In preferred embodiments of the compounds provided herein that include alkyl, alkenyl, or alkynyl portions include lower alkyl, lower alkenyl, and lower alkynyl portions.

As used herein aryl refers to cyclic groups containing from 3 to 15 or 16 carbon atoms, preferably from 5 to 10. Aryl groups include, but are not limited to groups, such as phenyl, substituted phenyl, naphthyl, substituted naphthyl, in which the substituent is lower alkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is hydrogen, alkyl, preferably lower alkyl or aryl, preferably lower aryl.

As used herein "dialkylaminocarbonyl" as used herein refers to —C(O)NR'R in which R' and R are independently selected from alkyl or aryl, preferably lower alkyl or lower aryl; "carboxamide" refers to groups of formula NR'COR.

As used herein, "alkoxycarbonyl" as used herein refers to —C(O)OR in which R is alkyl, preferably lower alkyl or aryl, preferably lower aryl.

As used herein, "alkoxy" and "thioalkoxy" refer to RO— and RS—, in which R is alkyl, preferably lower alkyl or aryl, preferably lower aryl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is alkyl, preferably lower alkyl or aryl, preferably lower aryl.

As used herein, "alkoxycarbonyl" refers to —C(O)OR in which R is alkyl, preferably lower alkyl.

As used herein, cycloalkyl refers to saturated cyclic carbon chains; cycloalkyenyl and cycloalkynyl refer to cyclic carbon chains that include at least one unsaturated triple bond. The cyclic portions of the carbon chains may include one ring or two or more fused rings.

As used herein, heterocycle or heteroaryl refers to ring structures that include at least one carbon atom and one or more atoms, such as N, S and O. The rings may be single rings or two or more fused rings. Heteroaryl is used interchangeably with heterocycle.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942).

A. Compounds for Use in Treating Endothelin-Mediated Diseases Isoxazolylsulfonamides in which $Ar^2$ is Phenyl, Biphenyl and Fused Carbocyclic and Heterocyclic Rings Compounds and methods for treating endothelin-mediated diseases using the compounds of formula I are provided. Compounds in which $Ar^2$ is selected from phenyl, biphenyl, and aromatic fused rings, including naphthyl, anthracenyl, phenanthryl, indenyl, azulenyl, fluorenyl, and phenazinyl and in which $Ar^1$ is oxazolyl or other heterocycle, such as pyridazinyl, are provided.

In particular, the compounds provided herein have formulae II. When $Ar^2$ is phenyl, biphenyl or naphthyl, the compounds are preferably (4-halo-isoxazolyl)sulfonamides or are (4-higher alkyl-isoxazolyl)sulfonmides, in which the alkyl group contains more than about 8, preferably 9 to 15, more preferably 9 to 13, carbon atoms.

Among the compounds provided herein are those of formulae (III):

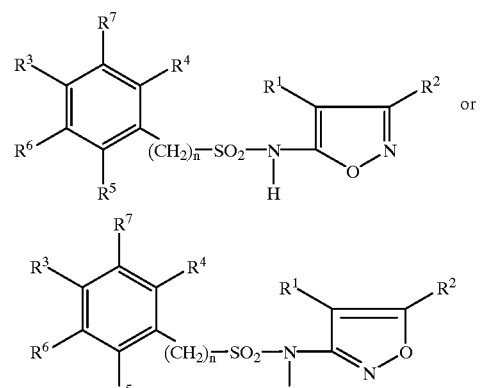

in which n is 0 to 10, preferably 0 to 6, more preferably 0 to 3; $R^3$, $R^4$, $R^5$, $R^6$, and $R^7$ are selected from (i), (ii), (iii), (iv) or (v) with the proviso that: (a) when $Ar^2$ is phenyl, and $R^4$, $R^5$, $R^6$ and $R^7$ are hydrogen, $R^3$ is not $NO_2$, $NH_2$ or lower alkyl, particularly $CH_3$, unless $R^1$ is higher alkyl; and (b) when $Ar^2$ is naphthyl, 2-biphenyl or phenyl, other than 3- or 4-biphenyl in which $R^4$ and $R^5$ are hydrogen or fused rings (except for naphthyl), $R^1$ is halide or higher alkyl ($C_8$–$C_{15}$ preferably $C_9$–$C_{13}$):

(i) $R^3$, $R^4$, $R^5$, $R^6$, and $R^7$ are each selected independently from among H, NHOH, $NH_2$, $NO_2$, $N_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; or, alternatively, (ii) $R^4$ and $R^7$ together are substituted or unsubstituted 1,3-butadienyl, 4-dimethylamino-1,3-butadienyl, 1-chloro-1,3-butadienyl, 1-aza-1,3-butadienyl or 2-aza-1,3-butadienyl groups; and $R^3$, $R^5$ and $R^6$ are as defined in (i) above; or alternatively, (iii) $R^7$ and $R^3$ together are substituted or unsubstituted 1,3-butadienyl, 4-dimethylamino-1,3-butadienyl, 1-chloro-1,3-butadienyl, 1-aza-1,3-butadienyl or 2-aza-1,3-butadienyl groups; and n, X, $R^4$, $R^5$ and $R^6$ are as defined in (i) above; or (iv) $R^3$, $R^5$, and $R^7$ are H or as defined in (i); and $R^4$ and $R^6$ are each independently selected from alkyl, alkoxy, halide, aminoalkyl, dialkylaminoalkyl, in which the alkyl and alkoxy groups contain from 1 to 10, preferably 1 to 6 carbons, and are straight or branched chains;

(v) any two of $R^3$, $R^4$, $R^5$, $R^6$, and $R^7$, which are selected as in (i), form fused carbocyclic or heterocyclic rings.

In more preferred embodiments the above compounds in which, $R^2$ is H, $CH_3$, $C_2H_5$, or $CF_3$; $R^1$ is Cl, Br or $CH_3$; n is 0 or 1; and $R^3$, $R^4$, $R^5$, $R^6$, $R^7$, are selected from either (i), (ii), (iii) or (iv) as follows:

(i) $R^5$ and $R^6$ are H; $R^4$ and $R^7$ are each independently selected from H, halide, $NH_2$, $CF_3$, Ph, $CH_3$; and $R^3$ is selected from H, NHOH, $NH_2$, EtNH, $(CH_3)_2N$, Ph—$CH_2$NH, $NO_2$, F, Cl, Br, I, CN, $CH_3$, $(CH_3)_3C$, $C_5H_{11}$, $CH_3O$, n-$C_4H_9O$, $CH_2$=CH, Ph—CH=CH, CH≡C, Ph—C≡C, Ph, 3-(ethyoxycarbonylmethyl) ureido, and 3-cyclohexylureido; or (ii) $R^4$ and $R^7$ together form 1,3-butadienyl, 4-chloro-1,3-butadienyl, 4-dimethylamino-1,3-butadienyl or 1-aza-1,3-butadienyl; and $R^3$, $R^5$ and $R^6$ are defined as in (i) of this embodiment; or (iii) $R^7$ and $R^3$ together form 1,3-butadienyl, 3-chloro-1,3-butadienyl, 4-dimethylamino-1,3-butadienyl or 1-aza-1,3-butadienyl; and $R^4$, $R^5$ and $R^6$ are as defined in (i) of this embodiment; or (iv) $R^3$, $R^5$, and $R^7$ are H or as defined in (i); and $R^4$ and $R^6$ are each independently selected from alkyl, alkoxy, halide, amino alkyl, alkylaminoalkyl or dialkylaminoalkyl, in which the alkyl and alkoxy groups contain from 1 to 10, preferably 1 to 6 carbons, and are straight or branched chains are provided.

More preferred among the above compounds are those in which $Ar^2$ is a substituted or unsubstituted phenyl, particularly biphenyl, or naphthyl; $R^1$ is Br, Cl or I; $R^2$ is H, $CH_3$, $C_2H_5$, $CF_3$, $C_2F_5$, n-$C_3H_7$, cyclo$C_3H_5$, and $C_4H_9$; and $R^3$, $R^4$, $R^5$, $R^6$ and $R^7$ are either (i), (ii), (iii), (iv) or (v):

(i) $R^5$, $R^6$ and $R^7$ are H; n is 0 and $R^3$ is H, $NH_2$, $CH_3$ $CF_3$, halide, $C_2H_5$NH or Ph, $R^4$ is H, $CF_3$, $NH_2$, $R^7$ is H or $CF_3$, and $R^5$ and $R^6$ are H; or (ii) $R^3$, $R^5$ and $R^6$ are H; n is 0 and $R^4$ and $R^7$ together form 1,3-butadienyl, 4-dimethylamino-1,3-butadienyl, 1-chloro-1,3-butadienyl, or 4-chloro-1,3-butadienyl; or (iii) $R^4$, $R^5$ and $R^6$ are H; n is 0; and $R^7$ and $R^3$ together form 1,3-butadienyl, 4-dimethylamino-1,3-butadienyl, 1-chloro-1,3-butadienyl, 1-aza-1,3-butadienyl; or (iv) $R^4$ is H or $NH_2$, $R^5$ and $R^6$ are H; n is 1 and $R^3$ is H, $NH_2$ and halide; $CH_3$, Br, Cl, F, $CF_3$, $NH_2$, $R^7$ is H, $CH_3$, Br, Cl, F, $NH_2$ or $CF_3$, and $R^5$ and $R^6$ are H; or (v) $R^3$, $R^5$, and $R^7$ are H are as defined in (i); and $R^4$ and $R^6$ are each independently selected from alkyl groups that contain from 1 to 6 carbons, and are straight or branched chains, lower alkoxy, and halide.

In more preferred embodiments, the benzenesulfonamides and naphthalenesulfonamdies are N-(4-halo)-substituted N-isoxazolylsulfonamides or are 4-higher alkyl-substituted N-isoxazolylsulfonamides, in which $R^2$ is H, $CH_3$, $C_2H_5$, $C_2F_5$ or $CF_3$; and $R^3$, $R^4$, $R^5$, $R^6$ and $R^7$ are either (i) or (ii) as follows:

(i) $R^4$, $R^5$, $R^6$ and $R^7$ are each independently selected from H, halide, $NH_2$, $CF_3$, Ph and $CH_3$; $R^3$ is selected from H, NHOH, $NH_2$, $C_2H_5$NH, $(CH_3)_2N$, Ph—$CH_2$NH, $NO_2$, F, Cl, Br, I, CN, $CH_3$, $(CH_3)_3C$, $C_5H_{11}$, $CH_3O$, n-$C_4H_9O$, $CH_2$=CH, Ph—CH=CH, CH≡C, Ph—C≡C, Ph, 3-(ethyoxycarbonylmethyl)ureido, and 3-cyclohexylureido; or (ii) $R^3$, $R^5$ and $R^7$ are H; and $R^4$ and $R^6$ are each an alkyl group that contains from 1 to 3 carbons, which are straight or branched chains.

In yet more preferred embodiments, $R^1$ is most preferably Br or Cl or higher alkyl ($C_9$–$C_{13}$); $R^2$ is $CH_3$, $C_2H_5$ or $CF_3$; and $R^3$, $R^4$, $R^6$ and $R^7$ are (i) or (ii) as follows:

(i) $R^3$ is H, $NH_2$, $CH_3$ $CF_3$, halide or $C_2H_5$NH; $R^4$, $R^5$ and $R^6$ are independently selected from H, $CF_3$, halide, particularly Br and Cl, $NH_2$; and $R^7$ is H, $CH_3$, $CH_2CH_3$, $(CH_3)_2CH$, F or $CF_3$; or (ii) $R^3$, $R^5$ and $R^7$ and $R^4$ and $R^6$ are each an methyl or ethyl.

In all embodiments, $R^1$ is most preferably Br, except in instances in which enhanced $ET_B$ affinity, compared to the corresponding compound in which $R_1$ is $CH_3$, is desired, than $R^1$ is most preferably a higher alkyl (8 to 15 carbons, preferably 9 to 13 carbons).

1. Compounds in Which $Ar^2$ is Phenyl and Biphenyl and n is 0

Compounds in which $Ar^2$ is phenyl or biphenyl have the following formulae (IV):

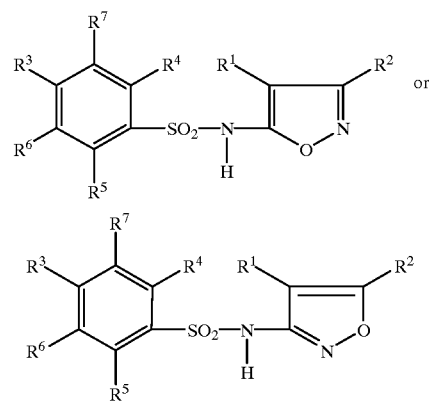

in which $R^3$, $R^4$, $R^5$, $R^6$, and $R^7$ are selected from (i) or (ii) with the proviso that, (a) when $Ar^2$ is phenyl, $R^3$ is not $NO_2$, $NH_2$, or lower alkyl, unless $R^1$ is higher alkyl ($C_8$–$C_{15}$, preferably $C_9$–$C_{13}$), and (b) when $Ar^2$ is naphthyl, 2-biphenyl, or phenyl, other than 3- or 4- biphenyl in which $R^4$ and $R^5$ is H, dibenzofuryl, dibenzothiophenyl or dibenzopyrrolyl, $R^1$ is halide or higher alkyl:
  (i) $R^3$, $R^4$, $R^5$, $R^6$, and $R^7$ are each selected independently from among H, NHOH, $NH_2$, $NO_2$, $N_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; are each independently selected as described above; or, alternatively,
  (ii) $R^3$, $R^5$, and $R^7$ are H; and $R^4$ and $R^6$ are each independently selected from alkyl, alkoxy, halide aminoalkyl, dialkylaminoalkyl, which are unsubstituted or substituted with alkyl groups, wherein the alkyl and alkoxy groups contain from 1 to 10, preferably 1 to 6 carbons, and are straight or branched chains.

Among the above phenyl and biphenyl compounds, are compounds with the following formulae (V):

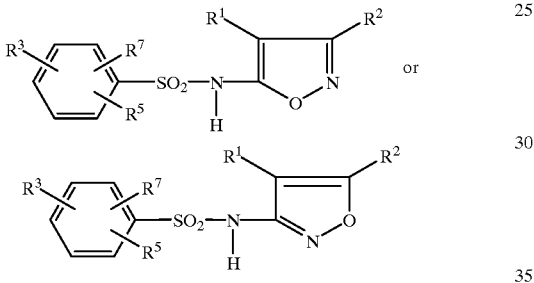

in which $R^3$, $R^5$ and $R^7$ are each independently
  (a) hydrogen, except that at least one of $R^3$, $R^5$ and $R^7$ is other than hydrogen and any substituent at the 4-position on the phenyl ring is not $NH_2$, $NO_2$ or lower alkyl, when the other substituents are hydrogen;
  (b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with $W^1$, $W^2$ and $W^3$, except that if one of $R^3$, $R^5$ are $R^7$ is alkyl at the 4 position, at least one of the other two of $R^3$, $R^5$ are $R^7$ is not hydrogen;
  (c) halo;
  (d) hydroxyl;
  (e) cyano;
  (f) nitro, except that if one of $R^3$, $R^5$ and $R^7$ is 4-$NO_2$, then at least one of the other two of $R^3$, $R^5$ and $R^7$ is not hydrogen;
  (g) —C(O)H or —C(O)$R^{27}$;
  (h) —$CO_2$H or —$CO_2R^{27}$;
  (i) —SH, —S(O)$_n R^{27}$, —S(O)$_m$—OH, —S(O)$_m$—O$R^{27}$, —O—S(O)$_m$OH, or —O—S(O)$_m$O$R^{27}$;
  (j) —$W^4 NR^{28} R^{29}$, except that, if one of $R^3$, $R^5$ and $R^7$ is 4-$W^4 NR^{28} R^{29}$ then at least one of the other two of $R^3$, $R^5$ and $R^7$ is not hydrogen; or
  (k) —$W^4 N(R^{32})$—$W^5 NR^{30} R^{31}$;

$R^1$ is halide or is higher alkyl (about 8 carbons up to about 15 carbons in the chain, preferably $C_9$-$C_{13}$), except when the compounds are 3- or 4-biphenyls in which the 2-substituent is hydrogen, then $R^1$ is selected, independently from $R^2$ from the substituents set forth for $R^2$;

$R^2$ is selected from:
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with $W^1$, $W^2$ and $W^3$;
  (c) hydroxyl;
  (d) cyano;
  (e) nitro;
  (f) —C(O)H or —C(O)$R^{27}$;
  (g) —$CO_2$H or —$CO_2R^{27}$;
  (h) —SH, —S(O)$_n R^{27}$, —S(O)$_m$OH, —S(O)$_m$O$R^{27}$, —O—S(O)$_m$—$R^{27}$, —O—S(O)$_m$OH, or O—S(O)$_m$—O$R^{27}$;
  (i) —$W^4$—$NR^{28} R^{29}$; or
  (j) —$W^4 N(R^{32})$—$W^5$—$NR^{30} R^{31}$;

$R^{27}$ is alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{28}$ is
  (a) hydrogen;
  (b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;
  (c) cyano;
  (d) hydroxyl;
  (e) —C(O)H or —C(O)$R^{27}$;
  (f) —$CO_2R^{27}$;
  (g) —SH, —S(O)$_m R^{27}$, —S(O)$_m$—OH, —S(O)$_m$—O$R^{27}$, —O—S(O)$_m$—$R^{27}$, —O—O—S(O)$_m$OH, or —O—S(O)$_m$—O$R^{27}$, except when $W^4$ is —S(O)$_n$—;

$R^{29}$ is
  (a) hydrogen;
  (b) —C(O)H or —C(O)$R^{27}$, except when $W^4$ is —C(O)— and $R^{28}$ is —C(O)H, —C(O)$R^{27}$, or —$CO_2R^{27}$;
  (c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$; or $R^{28}$ and $R^{29}$ together are alkylene or alkenylene (either of which may be substituted with $W^1$, $W^2$ and $W^3$), completing a 3- to 8-membered saturated, unsaturated or aromatic ring together with the nitrogen atom to which they are attached;

$R^{30}$ is
  (a) hydrogen;
  (b) hydroxyl;
  (c) —C(O)H or —C(O)$R^{27}$;
  (d) —$CO_2R^{27}$;
  (e) —SH, —S(O)$_n R^{27}$, —S(O)$_m$—OH, —S(O)$_m$—O$R^{27}$, —O—S(O)$_m$—$R^{27}$, —O—S(O)$_m$OH, or —O—S(O)$_m$—O$R^{27}$;
  (f) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{31}$ is
  (a) hydrogen;
  (b) —C(O)H or —C(O)$R^{27}$, except when $W^5$ is —C(O)— and $R^{30}$ is —C(O)H, —C(O)$R^{27}$, or —$CO_2R^{27}$; or
  (c) alkyl, alkenyl, alkynyl, alkoxy, cycloalkyl, cycloalkylalkyl, cycloalkenyl, cycloalkenylalkyl, aryl, or aralkyl, any of which may be substituted with W¹, W² and W³;

R³² is
(a) hydrogen;
(b) hydroxyl
(c) —C(O)H, —C(O)R²⁷ or CO₂R²⁷; or
(d) alkyl, alkenyl, alkynyl, alkoxy, cycloalkyl, cycloalkylalkyl, cycloalkenyl, cycloalkenylalkyl, aryl, or aralkyl, any of which may be substituted with W¹, W² and W³;

or any two of R³⁰, R³¹ and R³² together are alkylene or alkenylene (either of which may be substituted with W¹, W² and W³), completing a 3- to 8-membered saturated, unsaturated or aromatic ring together with the atoms to which they are attached;

W¹, W² and W³ are each independently
(a) hydrogen;
(b) halo;
(c) hydroxy;
(d) alkyl;
(e) alkenyl;
(f) aralkyl;
(g) alkoxy;
(h) aryloxy;
(i) aralkoxy;
(j) —SH, —S(O)ₙW⁶, —S(O)ₘ—OH, —S(O)ₘ—OW⁶, —O—S(O)ₘ—W⁶, —O—S(O)ₘOH, or —O—S(O)ₘ—OW⁶;
(k) oxo;
(l) nitro;
(m) cyano;
(n) —C(O)H or —C(O)W⁶;
(o) —CO₂H or —CO₂W⁶;
(p) —W⁴—NW⁷W⁸;
(q) W⁴—N(W¹¹)—W⁵—W⁶; or
(r) —W⁴—N(W¹¹)—W⁵—NW⁷W⁸;

W⁴ and W⁵ are each independently
(a) a single bond;
(b) —W⁹—S(O)ₙ—W¹⁰—;
(c) —W⁹—C(O)—W¹⁰;
(d) —W⁹—C(S)—W¹⁰—;
(e) —W⁹—O—W¹⁰—;
(f) —W⁹—S—W¹⁰—; or
(g) —W⁹—O—C(O)—W¹⁰—;

W⁶, W⁷ and W⁸ are each independently hydrogen, alkyl, alkenyl, alkynyl, cycloalkyl, cycloalkylalkyl, cycloalkenyl, cycloalkenylalkyl, aryl, or aralkyl, or W⁷ and W⁸ together are alkylene or alkenylene, completing a 3- to 8-membered saturated, unsaturated or aromatic ring together with the nitrogen atom to which they are attached;

W⁹ and W¹⁰ are each independently a single bond, alkylene, alkenylene, or alkynylene;

W¹¹ is
(a) hydrogen;
(b) hydroxyl;
(c) —C(O)H, —C(O)W⁶ or —CO₂W⁶;
(d) alkyl, alkenyl, alkynyl, alkoxy, cycloalkyl, cycloalkylalkyl, cycloalkenyl, cycloalkenylalkyl, aryl, or aralkyl; or any two of W⁷ and W⁸ and W¹¹ together are alkylene or alkenylene, completing a 3- to 8-membered saturated, unsaturated, or aromatic ring together with the atoms to which they are attached;

m is 1 or 2; and
n is 0, 1, or 2.

Preferred compounds include those in which one of R³, R⁵ or R⁷ is phenyl or phenoxy or compounds in which one of R³, R⁵ or R⁷ is hydrogen, one of the other two of R³, R⁵ and R⁷ is at the 2 position and is not hydrogen, and the other of R³, R⁵ and R⁷ is at the 5 position. Thus, preferred compounds are 2-substituted benzenesulfonamides, and 2,5-substituted benzenesulfonamides. In addition, in preferred compounds R¹ is preferably halide or higher alkyl. Preferred substituents are lower alkyl, particular methyl, ethyl, and propyl, halide, amino, dimethylamino, and methoxy.

(a) Benzenesulfonamides (Other Than Biphenylsulfonamides)

Benzene sulfonamides are provided. In these compounds Ar² has the formula (VI):

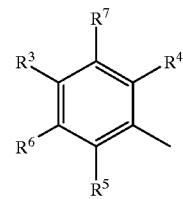

in which:
R¹ is halide or higher alkyl (greater than 8 carbons); R² selected from H, NH₂, NO₂, halide, pseudohalide, alkyl, alkenyl, alkynyl, aryl, arylalkyl, heteroaryl, alkoxy, alkylamino, alkylthio, haloalkoxy, haloalkyl, alkylsulfinyl, alkylsulfonyl, aryloxy, arylamino, arylthio, arylsulfinyl, arylsulfonyl, aminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons; and R³, R⁴, R⁵, R⁶, and R⁷ are either (i) or (ii) as follows:
(i) R³, R⁴, R⁵, R⁶, and R⁷ are selected independently from among H, NHOH, NH₂, NO₂, pseudohalide, including N₃, halide, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons, are unsubstituted or substituted with groups set forth for Z, above, and the aryl portions contain from 3 up to about 10 carbons, preferably 3 to 6 carbons, and, also are unsubstituted or substituted with groups, independently selected from Z, with the proviso that, if R⁴, R⁵, R⁶, and R⁷ are all hydrogen, then R³ is not NO₂, NH₂ or lower alkyl; or (ii) R³, R⁵, and R⁷ are H; and R⁴ and R⁶ are each independently selected from alkyl, alkoxy, halide, aminoalkyl, dialkylamino, dialkylaminoalkyl, which are unsubstituted or substituted with alkyl groups, and in which the alkyl and alkoxy groups contain from 1 to 10, preferably 1 to 6 carbons, and are straight or branched chains.

Compounds in which at least one of R³–R⁷ is phenyl are discussed below with the biphenyl compounds.

In certain preferred embodiments: $R^1$ is halide or a higher alkyl selected from $C_9H_{19}$ to $C_{13}H_{27}$; $R^2$ is selected independently from alkyl, lower alkenyl, lower alkynyl, lower haloalkyl and H; and $R^3$, $R^4$, $R^5$, $R^6$, and $R^7$ are either (i) or (ii) as follows:

(i) $R^4$, $R^5$, $R^6$ and $R^7$ are each independently selected from H, lower alkyl, $NH_2$, $NO_2$, halide, pseudohalide; $R^3$ is selected from H, NHOH, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from 1 up to 5 or 6 carbons and the aryl portions contain from 4 to 14 carbons; or (ii) $R^3$, $R^5$, and $R^7$ are H; and $R^4$ and $R^6$ are each independently selected from alkyl, alkoxy, halide, aminoalkyl, and dialkylaminoalkyl, which are unsubstituted or substituted with alkyl groups, and in which the alkyl and alkoxy groups contain 1 to 6 carbons, and are straight or branched chains.

In more preferred embodiments, $R^1$ is Cl or Br, or if greater $ET_B$ activity is preferred a higher alkyl ($C_9H_{19}$ to $C_{13}H_{27}$; $R^2$ is selected from H, $CH_3$, $C_2H_5$, $CF_3$, $C_2F_5$, n-$C_3H_7$, cyclo-$C_3H_7$, $nC_{13}H_{27}$ and $nC_9H_{19}$; and $R^3$, $R^4$, $R^5$, $R^6$, and $R^7$ are either (i) or (ii) as follows:

(i) $R^4$, $R^5$, $R^6$ and $R^7$ are each independently selected from H, halide, $NH_2$, $CF_3$, Ph and $CH_3$; $R^3$ is selected from H, NHOH, $NH_2$, $C_2H_5NH$, $(CH_3)_2N$, Ph—$CH_2NH$, $NO_2$, F, Cl, Br, I, CN, $CH_3$, $(CH_3)_3C$, $C_5H_{11}$, $CH_3O$, n-$C_4H_9O$, $CH_2$=CH, Ph—CH=CH, CH≡C, Ph—C≡C, Ph, 3-(ethyoxycarbonylmethyl)ureido, and 3-cyclohexylureido; or (ii) $R^3$, $R^5$, and $R^7$ are H; and $R^4$ and $R^6$ are each independently selected from alkyl and aminoalkyl in which the alkyl groups have from 1 to 6 carbons that may from straight or branched chains.

In yet more preferred embodiments, $R^1$ is Br, Cl or $C_9H_{19}$ to $C_{13}H_{27}$; $R^2$ is H, $CH_3$, $C_2H_5$, or $CF_3$; and $R^3$, $R^4$, $R^5$, $R^6$, and $R^7$ are either (i) or (ii) as follows:

(i) $R^3$ is H, $NH_2$, $CH_3$ $CF_3$, halide or $C_2H_5NH$; $R^4$, $R^5$ and $R^6$ are independently selected from H, $CH_3$, $C_2H_5$, $(CH_3)_2CH$, $CF_3$, halide, particularly Br and Cl, $NH_2$; and $R^7$ is H, $CH_3$, $CH_2CH_3$, $(CH_3)_2CH$, F or $CF_3$; or (ii) $R^3$, $R^5$, and $R^7$ are H; and $R^4$ and $R^6$ are each independently selected from alkyl groups in which the alkyl groups have from 1 to 3 carbons and may form straight or branched chains.

Of the above compounds those with ortho and/or meta substituents or those that are substituted at positions 2 and 5 on the benzene ring are generally more preferred, except when the resulting compound is a biphenyl and $ET_B$ affinity is desired, then the corresponding para-substituted compounds are preferred. Compounds with ortho substituents are more generally more preferred than the corresponding meta-substituted compounds. This observation is particularly important when activity with respect to $ET_A$ receptors is considered. In addition, in preferred compounds $R^1$ is preferably halide. Preferred substituents are lower alkyl, particular methyl, ethyl, and propyl, halide, amino, dimethylamino, and methoxy. Other preferred substituents may be deduced from the following Table.

Benzenesulfonamides were synthesized and tested using the exemplified assays (see, EXAMPLES) and selected results are set forth in Table 1 (the N-(3,4-dimethyl-5-isoxazolyl)benzenesulfonamides, which are not included in the above formulae, are included for comparison with the corresponding N-(4-halo-3-methyl-5-isoxazolyl)benzenesulfonamide.

TABLE 1

| COMPOUND | $ET_A$ ($\mu M$)* | $ET_B$ ($\mu M$)* |
|---|---|---|
| N-(4-bromo-5-methyl-3-isoxazolyl)benzenesulfonamide | 0.097 ± 0.04 | 31 ± 5.3 |
| 2-chloro-4-fluoro-N-(5-methyl-3-isoxazoly)benzenesulfonamide | — | — |
| N-(4-bromo-5-tert-butyl-3-isoxazolyl)benzenesulfonamide | — | — |
| N-(4-chloro-5-methyl-3-isoxazolyl)benzenesulfonamide | — | — |
| N-(4-iodo-5-methyl-3-isoxazolyl)benzenesulfonamide | — | — |
| 4-nitro-N-(4-bromo-5-methyl-3-isoxazolyl)benzenesulfonamide | — | — |
| 5-nitro-N-(4-bromo-5-methyl-3-isoxazolyl)benzenesulfonamide | — | — |
| N-(4-bromo-3-methyl-5-isoxazolyl)benzenesulfonamide | 0.055 ± 0.005 | 19.5 ± 4 |
| N-(4-bromo-3-phenyl-5-isoxazolyl)benzenesulfonamide | — | — |
| N-(4-chloro-3-methyl-5-isoxazolyl)benzenesulfonamide | ~0.11 | 25.6 |
| N-(4-bromo-3-tert-butyl-5-isoxazolyl)benzenesulfonamide | — | — |
| 4-iso-propyl-N-(4-bromo-3-methyl-5-isoxazolyl)benzenesulfonamide | 17.3 | 0.78 |
| 4-bromo-N-(3,4-dimethyl-5-isoxazolyl)benzenesulfonamide | 8.9 | 14.4 |
| 4-bromo-N-(4-bromo-3-methyl-5-isoxazolyl)benzenesulfonamide | 3.0 | 3.8 |
| 4-fluoro-N-(3,4-dimethyl-5-isoxazolyl)benzenesulfonamide | 7 ± 3 | 57 ± 13 |

TABLE 1-continued

| COMPOUND | ET$_A$ (μM)* | ET$_B$ (μM)* |
|---|---|---|
| 4-fluoro-N-(4-bromo-3-methyl-5-isoxazolyl)benzenesulfonamide | 1.2 | 15.3 |
| 3-nitro-N-(3,4-dimethyl-5-isoxazolyl)benzenesulfonamide | 13.7 | — |
| 3-nitro-N-(4-bromo-3-methyl-5-isoxazolyl)benzenesulfonamide | 2.8 | 40 |
| 4-iodo-N-(4-bromo-3-methyl-5-isoxazolyl)benzenesulfonamide | 6.3 ± 2.5 | 1.05 ± 0.08 |
| 4-chloro-N-(4-bromo-3-methyl-5-isoxazolyl)benzenesulfonamide | 1.96 ± 1 | 7.02 ± 2 |
| N-(4-bromo-3-ethyl-5-isoxazolyl)benzenesulfonamide | 0.47 ± 0.3 | 67.1 ± 6 |
| 4-methyl-N-(4-bromo-3-methyl-5-isoxazolyl)-4-benzenesulfonamide | 1.44 ± 0.8 | 4.0 ± 0.9 |
| 2,5-dimethyl-N-(4-bromo-3-methyl-5-isoxazolyl)benzenesulfonamide | 0.044 ± 0.03 | 15.5 ± 3 |
| 2-fluoro-N-(4-bromo-3-methyl-5-isoxazolyl)benzenesulfonamide | 0.20 | 40.8 |
| 3-fluoro-N-(4-bromo-3-methyl-5-isoxazolyl)benzenesulfonamide | 0.21 | 38.3 |
| 2,5-dimethyl-N-(3,4-di-methyl-5-isoxazolyl)benzenesulfonamide | 9.4 | 66.3 |
| 2,5-dimethyl-N-(4-chloro-3-methyl-5-isoxazolyl)benzenesulfonamide | 0.19 | 30.7 |
| 4-acetamido-N-(3,4-dimethyl-5-isoxazolyl)benzenesulfonamide | 18.1 | — |
| 4-acetamido-N-(4-bromo-3-methyl-5-isoxazolyl)benzenesulfonamide | 6.4 ± 3.5 | ~26 |
| 4-nitro-N-(3,4-dimethyl-5-isoxazolyl)benzenesulfonamide | 100 | 10 |
| 4-nitro-N-(4-bromo-5-methyl-3-isoxazolyl)benzenesulfonamide | 53 ± 1.0 | 9.4 ± 2 |
| 2,4,6-trimethyl-N-(3,4-dimethyl-5-isoxazolyl)benzenesulfonamide | 52 ± 4 | — |
| 2,4,6-trimethyl-N-(4-bromo-3-methyl-5-isoxazolyl)benzenesulfonamide | 5.9 ± 0.9 | 45.5 ± 4.4 |
| 4-iodo-N-(3,4-dimethyl-5-isoxazolyl)benzenesulfonamide | 36 ± 3 | 6 |
| 4-iodo-N-(4-bromo-3-methyl-5-isoxazolyl)benzenesulfonamide | 6.3 ± 2.5 | 1.05 ± 0.08 |
| 4-chloro-N-(3,4-dimethyl-5-isoxazolyl)benzenesulfonamide | 10.2 ± 1.5 | 29.2 ± 0.07 |
| 4-chloro-N-(4-bromo-3-methyl-5-isoxazolyl)benzenesulfonamide | 1.96 ± 1 | 7.02 ± 2 |
| 2-chloro-N-(4-bromo-3-methyl-5-isoxazolyl)benzenesulfonamide | .071 ± .06 | 37 ± 2 |
| 3,4-dichloro-N-(3,4-dimethyl-5-isoxazolyl)benzenesulfonamide | 3.8 ± 1.5 | 25 ± 6 |
| 3,4-dichloro-N-(4-bromo-3-methyl-5-isoxazolyl)benzenesulfonamide | **0.90 ± 0.2<br>0.48 ± 0.07 | 6.9 ± 1.8<br>6.5 ± 0.9 |
| 2,4-dichloro-N-(3,4-dimethyl-5-isoxazolyl)benzenesulfonamide | 14 ± 7 | 104 ± 12 |
| 2,4-dichloro-N-(4-bromo-3-methyl-5-isoxazolyl)benzenesulfonamide | 2.6 ± 0.3 | 24 ± 7 |
| 2-fluoro-N-(4-bromo-3-methyl-5-isoxazolyl)benzenesulfonamide | 0.16 ± 0.04 | 35 ± 6 |
| 3-fluoro-N-(4-bromo-3-methyl-5-isoxazolyl)benzenesulfonamide | 0.14 ± 0.06 | 24.8 |
| 2,5-dimethyl-N-(4-chloro-3-methyl-5-isoxazolyl)benzenesulfonamide | 12.7 ± 6.7 | 12 |
| 4-nitro-N-(4-bromo-3-methyl-5-isoxazolyl)benzenesulfonamide | 19 ± 5 | 6.8 ± 3 |
| 4-butoxy-N-(3,4-dimethyl-5-isoxazolyl)benzenesulfonamide | 9.2 | 7.4 |
| 4-butoxy-N-(4-bromo-3-methyl-5-isoxazolyl)benzenesulfonamide | 3.0 ± 0.7 | 2.0 ± 0.8 |
| 3-chloro-2-methyl-N-(4-bromo-3-methyl-5-isoxazolyl)benzenesulfonamide | 0.165 ± 0.13 | 22 ± 15 |
| 2-methyl-N-(4-bromo-3-methyl-5-isoxazolyl)benzenesulfonamide | 0.12 ± 0.01 | 13 ± 1 |
| 3-chloro-2,5-dimethyl-N-(4-bromo-3-methyl-5-isoxazolyl)benzenesulfonamide | 0.31 ± 0.03 | 11.2 ± 0.3 |
| 2,6-difluoro-N-(4-bromo-3-methyl-5-isoxazolyl)benzenesulfonamide | 0.16 ± 0.1 | 63 ± 10 |
| 2,5-difluoro-N-(4-bromo-3-methyl-5-isoxazolyl)benzenesulfonamide | 2.4 ± 0.2 | 26.8 ± 3.7 |

TABLE 1-continued

| COMPOUND | ET$_A$ ($\mu$M)* | ET$_B$ ($\mu$M)* |
|---|---|---|
| 2,3,4-trichloro-N-(4-bromo-3-methyl-5-isoxazolyl)benzenesulfonamide | 2.1 ± 0.01 | 10.2 ± 2.0 |
| 2,3-dichloro-N-(4-bromo-3-methyl-5-isoxazolyl)benzenesulfonamide | 0.19 ± 0.04 | 20.4 ± 2.3 |
| 2,5-dichloro-N-(4-bromo-3-methyl-5-isoxazolyl)benzenesulfonamide | 0.113 ± 0.02 | 25 ± 3 |
| 5-bromo-2-methoxy-N-(4-bromo-3-methyl-5-isoxazolyl)benzenesulfonamide | 0.072 ± 0.03 | 5.3 ± 0.4 |
| 2-bromo-5-ethyl-N-(4-chloro-3-methyl-5-isoxazolyl)benzenesulfonamide | 0.057 | 3.5 ± 0.4 |
| 2-bromo-5-methyl-N-(4-bromo-3-methyl-5-isoxazolyl)benzenesulfonamide | 0.046 ± 0.002 | 11.5 ± 4 |
| 2-bromo-5-ethyl-N-(4-bromo-3-methyl-5-isoxazolyl)benzenesulfonamide | 0.029 ± 0.010 | 5.2 ± 1.1 |
| 5-bromo-2-ethyl-N-(4-bromo-3-methyl-5-isoxazolyl)benzenesulfonamide | 0.0028 ± 0.002 | 5.2 ± 1.1 |
| 2,5-diethyl-N-(4-bromo-3-methyl-5-isoxazolyl)benzenesulfonamide | 0.0062 ± 0.003 | 5.2 ± 0.8 |
| 2,5-diethyl-N-(3,4-dimethyl-5-isoxazolyl)benzenesulfonamide | 0.027 ± 0.01 | 17 ± 7 |
| 2-bromo-N-(4-bromo-3-methyl-5-isoxazolyl)benzenesulfonamide | 0.040 ± 0.02 | 39 ± 4 |
| 2-cyano-N-(4-bromo-3-methyl-5-isoxazolyl)benzenesulfonamide | 0.18 ± 0.02 | ~80 |
| 2,4,5-trichloro-N-(4-bromo-3-methyl-5-isoxazolyl)benzenesulfonamide | 1.2 ± 0.1 | 23 ± 3 |
| 3,4-dimethoxy-N-(4-bromo-3-methyl-5-isoxazolyl)benzenesulfonamide | 0.49 ± 0.18 | 24 ± 5 |
| 4-trifluoromethyl-N-(3,4-dimethyl-5-isoxazolyl)benzenesulfonamide | 129 | 12.1 |
| 4-trifluormethyl-N-(4-bromo-3-methyl-5-isoxazolyl)benzenesulfonamide | 22 ± 3.0 | 3.0 ± 0.2 |
| 3-trifluoromethyl-N-(4-bromo-3-methyl-5-isoxazolyl)benzenesulfonamide | 1.5 ± 0.2 | 21 ± 0.4 |
| 2,5-dimethoxy-N-(4-bromo-3-methyl-5-isoxazolyl)benzenesulfonamide | 0.19 ± 0.03 | 14 ± 0.7 |
| 5-chloro-2-methoxy-N-(4-bromo-3-methyl-5-isoxazolyl)benzenesulfonamide | 0.94 ± 0.14 | 10.2 ± 1 |
| 3-chloro-2-methyl-N-(3,4-dimethyl-5-isoxazolyl)benzenesulfonamide | 10.2 ± 1.5 | 29.2 ± 0.7 |
| 3-chloro-N-(4-bromo-3-methyl-5-isoxazolyl)benzenesulfonamide | 0.23 ± 0.06 | 34.7 ± 1.4 |
| N-(4-bromo-3-trifluoromethyl-5-isoxazolyl)benzenesulfonamide | 0.33 ± 0.08 | 34.7 ± 1.4 |
| N-(4-isothiocyanato-3-methyl-5-isoxazolyl)benzenesulfonamide | 0.62 ± 0.3 | — |
| 3-carboxyl-N-(4-bromo-3-methyl-5-isoxazolyl)benzenesulfonamide | 0.18 ± 0.05 | 7.6 ± 2.7 |
| 3,5-dichloro-N-(4-bromo-3-methyl-5-isoxazolyl)benzenesulfonamide | 0.062 ± 0.02 | 14.2 ± 1.0 |
| 3-chloro-5-fluoro-N-(4-bromo-3-methyl-5-isoxazolyl)benzenesulfonamide | 0.54 ± 0.1 | 17.0 ± 0.7 |
| 3,5-di(trifluoromethyl)-N-(4-bromo-3-methyl-5-isoxazolyl)benzenesulfonamide | 0.57 ± 0.07 | 17.1 ± 0.6 |
| 2,5-difluoro-N-(4-chloro-3-methyl-5-isoxazolyl)benzenesulfonamide | 0.19 ± 0.05 | 58 ± 10 |
| 2-chloro-5-methyl-N-(4-chloro-3-methyl-5-isoxazolyl)benzenesulfonamide | 0.22 ± 0.04 | 49 ± 2 |
| 2,5-dichloro-N-(4-bromo-3-methyl-5-isoxazolyl)benzenesulfonamide | 0.58 ± 0.25 | 17.4 ± 0.8 |
| 2-chloro-4-fluoro-N-(4-bromo-3-methyl-5-isoxazolyl)benzenesulfonamide | ~2.0 | 31 ± 0.3 |
| 2,5-difluoro-N-(4-bromo-3-methyl-5-isoxazolyl)benzenesulfonamide | 0.16 ± 0.1 | 63 ± 10 |
| 2-chloro-5-methyl-N-(4-bromo-3-methyl-5-isoxazolyl)benzenesulfonamide | 1.26 ± 0.19 | 37 ± 1 |
| 2-methyl-5-amino-N-(4-bromo-3-methyl-5-isoxazolyl)benzenesulfonamide | 0.34 ± 0.01 | ~100 |
| 2-methyl-5-dimethylamino-N-(4-bromo-3-methyl-5-isoxazolyl)benzenesulfonamide | 0.21 ± 0.03 | 44 ± 8 |
| 3-acetamido-N-(4-bromo-3-methyl-5-isoxazolyl)benzenesulfonamide | 0.35 ± 0.05 | 4.0 ± 1 |
| 3-bromo-N-(4-bromo-3-methyl-5-isoxazolyl)benzenesulfonamide | 0.23 ± 0.06 | 9.4 ± 1.4 |
| 2-phenoxy-5-nitro-N-(4-bromo-3-methyl-5-isoxazolyl)benzenesulfonamide | 0.79 ± 0.14 | 19.5 ± 0.1 |

TABLE 1-continued

| COMPOUND | $ET_A$ ($\mu$M)* | $ET_B$ ($\mu$M)* |
|---|---|---|
| 4-ethyl-N-(4-bromo-3-methyl-5-isoxazolyl)benzenesulfonamide | 0.34 ± 0.05 | 083 ± 0.05 |
| 2,5-dibromo-3,6-difluoro-N-(4-bromo-3-methyl-5-isoxazolyl)benzenesulfonamide | 0.035 | 13.3 ± 1 |
| 2-trifluoromethoxy-N-(4-bromo-3-methyl-5-isoxazolyl)benzenesulfonamide | 0.017 | 55 ± 7 |
| 2-methyl-5-fluoro-N-(4-bromo-3-methyl-5-isoxazolyl)benzenesulfonamide | 0.099 | 78 ± 8 |
| 2-butyl-5-bromo-N-(4-bromo-3-methyl-5-isoxazolyl)benzenesulfonamide | 0.038 | 3.6 ± 0.3 |
| 2-bromo-5-butyl-N-(4-bromo-3-methyl-5-isoxazolyl)benzenesulfonamide | 0.85 ± 0.11 | 5.4 ± 0.3 |
| 2-methyl-5-bromo-N-(4-bromo-3-methyl-5-isoxazolyl)benzenesulfonamide | 0.24 | 13 ± 2 |
| 2,5-dipropyl-N-(4-bromo-3-methyl-5-isoxazolyl)benzenesulfonamide | 0.19 ± 0.3 | 14.4 ± 1.8 |
| 2-dimethylamino-5-methyl-N-(4-bromo-3-methyl-5-isoxazolyl)benzenesulfonamide | 8.1 ± 0.2 | 0.93 ± 0.25 |
| 2-methylamino-5-methyl-N-(4-bromo-3-methyl-5-isoxazolyl)benzenesulfonamide | 0.0081 ± 0.0002 | 0.93 ± 0.25 |
| 2-methylamino-5-methyl-N-(4-chloro-3-methyl-5-isoxazolyl)benzenesulfonamide | 0.0032 ± 0.0001 | 5.6 ± 0.6 |
| 2-methyl-5-dimethylamino-N-(4-bromo-3-methyl-5-isoxazolyl)benzenesulfonamide | 0.25 ± 0.01 | 31 ± 4 |
| 2-ethyl-5-dimethylamino-N-(4-bromo-3-methyl-5-isoxazolyl)benzenesulfonamide | 0.16 | 23 |
| 2-methyl-5-azido-N-(4-bromo-3-methyl-5-isoxazolyl)benzenesulfonamide | 0.28 ± 0.04 | 4.2 ± 0.1 |
| 2,4-diethyl-N-(4-chloro-3-methyl-5-isoxazolyl)benzenesulfonamide | 0.62 ± 0.13 | 11.5 ± 3.4 |
| 2,4-diethyl-N-(4-bromo-3-methyl-5-isoxazolyl)benzenesulfonamide | 0.56 ± 0.08 | 9.3 ± 3 |
| 2-butyl-5-bromo-N-(4-chloro-3-methyl-5-isoxazolyl)benzenesulfonamide | 0.051 | 4.4 ± 0.1 |
| 2-bromo-N-(4-chloro-3-methyl-5-isoxazolyl)benzenesulfonamide | 0.086 | — |
| 2-bromo-5-butyl-N-(4-chloro-3-methyl-5-isoxazolyl)benzenesulfonamide | 1.1 | 4.6 ± 0.6 |
| 2-propyl-5-bromo-N-(3,4-dimethyl-5-isoxazoly)-benzenesulfonamide | ~.020 | 26 ± 4 |
| 2-propyl-5-bromo-N-(4-bromo-3-methyl-5-isoxazolyl)benzenesulfonamide | ~0.006 | 6.55 ± 0.2 |
| 2-propyl-5-bromo-N-(4-chloro-3-methyl-5-isoxazolyl)benzenesulfonamide | — | 14 ± 4 |
| 4-(N'-Cyclohexylureido-N-(3,4-dimethyl-5-isoxazolyl)benzenesulfonamide | 3.8 ± 0.3 | 100 ± 5 |
| N-(4-nonyl-3-trifluoromethyl-5-isoxazolyl)benzenesulfonamide | 8.7 ± 0.5 | 9.2 ± 0.7 |
| N-(4-tridecyl-3-trifluoromethyl-5-isoxazolyl)benzenesulfonamide | 13.2 ± 2 | 1.8 ± 0.5 |
| N-(4-ethyl-3-trifluoromethyl-5-isoxazolyl)benzenesulfonamide | 0.12 ± 0.02 | 27 ± 3 |
| N-(4-hexyl-3-trifluoromethyl-5-isoxazolyl)benzenesulfonamide | 11 ± 2.0 | 63 ± 9 |

*results generally from 1, 2 or 3 experiments with the same preparation
**Two preparations (b) $Ar^2$ is biphenyl Compounds of formulae I and 11 in which $Ar^1$ is N-(5-isoxazolyl) or N-(3-isoxazolyl) in which $Ar^2$ is selected from biphenyl or styryl derivatives. These compounds can be represented by the following formulae (III):

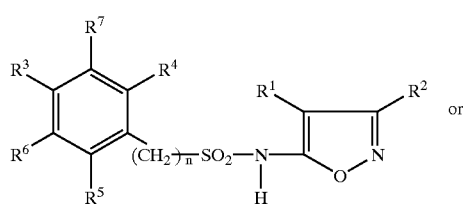

or

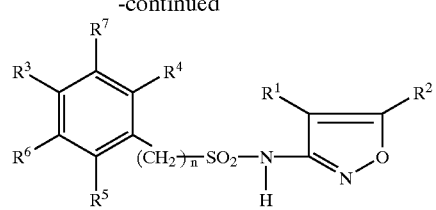

in which n is 0 to 10, preferably 0 to 6, more preferably 0 to 3;

$R^1$ and $R^2$ are either (i), (ii) or (iii) as follows:
(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that $R^2$ is not halide or pseudohalide; or, (ii) $R^1$ and $R^2$ together form —$(CH_2)_n$—, where n is 3 to 6; or, (iii) $R^1$ and $R^2$ together form 1,3-butadienyl, and with the proviso that $Ar^2$ is not 2-biphenyl or biphenyl in which $R^4$ and/or $R^5$ is other than hydrogen unless $R^1$ is a halide or higher ($C_8$–$C_{15}$, preferably $C_9$–$C_{13}$) alkyl;

at least one of $R^3$, $R^4$, $R^5$, $R^6$, and $R^7$ is phenyl, and the remaining of $R^3$, $R^4$, $R^5$, $R^6$ and $R^7$ are selected with the proviso that: (a) when one of $R^3$, $R^6$, and $R^7$ is phenyl, then $R^4$ and $R^5$ are hydrogen, unless $R^1$ is halide or higher alkyl ($C_8$–$C_{15}$, preferably $C_9$–$C_{13}$), and (b) when one of $R^4$ or $R^5$ is phenyl, then the other is hydrogen, unless $R^1$ is halide or higher alkyl ($C_8$–$C_{15}$, preferably $C_9$–$C_{13}$):

the others of $R^3$, $R^4$, $R^5$, $R^6$, and $R^7$ are selected independently from among H, NHOH, $NH_2$, $NO_2$, pseudohalide, including $N_3$, halide, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons, are unsubstituted or substituted with Z, above, and the aryl portions contain from 3 up to about 10 carbons, preferably 3 to 6 carbons, and, also are unsubstituted or substituted with groups.

In more preferred embodiments, $R^1$ is Cl or Br, or if greater $ET_B$ activity is preferred a higher alkyl ($C_9H_{19}$ to $C_{13}H_{27}$; $R^2$ is selected from H, $CH_3$, $C_2H_5$, $CF_3$, $C_2F_5$, n-$C_3H_7$, cyclo-$C_3H_7$, n$C_{13}H_{27}$ and n$C_9H_{19}$; and $R^3$, $R^4$, $R^5$, $R^6$, and $R^7$ are either (i) or (ii) as follows:

(i) $R^4$, $R^5$, $R^6$ and $R^7$ are each independently selected from H, halide, $NH_2$, $CF_3$, Ph and $CH_3$; $R^3$ is selected from H, NHOH, $NH_2$, $C_2H_5NH$, $(CH_3)_2N$, Ph—$CH_2NH$, $NO_2$, F, Cl, Br, I, CN, $CH_3$, $(CH_3)_3C$, $C_5H_{11}$, $CH_3O$, n-$C_4H_9O$, $CH_2$=CH, Ph—CH=CH, CH≡C, Ph—C≡C, Ph, 3-(ethyoxycarbonylmethyl)ureido, and 3-cyclohexylureido; or (ii) $R^3$, $R^5$, and $R^7$ are H; and one of $R^4$ and $R^6$ is phenyl and the other is selected from alkyl and aminoalkyl in which the alkyl groups have from 1 to 6 carbons that may form straight or branched chains.

In yet more preferred embodiments, $R^1$ is Br, Cl or $C_9H_{19}$ to $C_{13}H_{27}$; $R^2$ is H, $CH_3$, $C_2H_5$, or $CF_3$; and $R^3$, $R^4$, $R^5$, $R^6$, and $R^7$ are either (i) or (ii), with the proviso that at least one of them is substituted or unsubstituted phenyl, as follows:

(i) $R^3$ is H, $NH_2$, $CH_3$ $CF_3$, Ph, halide or $C_2H_5NH$; $R^4$, $R^5$ and $R^6$ are independently selected from H, $CH_3$, $C_2H_5$, $(CH_3)_2CH$, $CF_3$, halide, particularly Br and Cl, Ph and $NH_2$; and $R^7$ is H, $CH_3$, $CH_2CH_3$, $(CH_3)_2CH$, F or $CF_3$; or (ii) $R^3$, $R^5$, and $R^7$ are H or phenyl; and $R^4$ and $R^6$ are each independently selected from alkyl groups in which the alkyl groups have from 1 to 3 carbons and may form straight or branched chains.

In yet more preferred embodiments, $R^1$ is Br, Cl or $C_9H_{19}$ to $C_{13}H_{27}$; $R^2$ is H, $CH_3$, $C_2H_5$, or $CF_3$; and $R^3$, $R^4$, $R^5$, $R^6$, and $R^7$ are, with the proviso that at one of $R^3$, $R^4$, $R^5$, $R^6$, and $R^7$ is unsubstituted or substituted phenyl, selected as follows:

$R^3$ is Ph, H, $NH_2$, $CH_3$ $CF_3$, halide or $C_2H_5NH$; $R^4$, $R^5$ and $R^6$ are independently selected from Ph, H, $CH_3$, $C_2H_5$, $(CH_3)_2CH$, $CF_3$, halide, particularly Br and Cl, $NH_2$; and $R^7$ is Ph, H, $CH_3$, $CH_2CH_3$, $(CH_3)_2CH$, F or $CF_3$.

For the 3-or 4-biphenyl compounds, in which $R^4$ and/or $R^5$ is other than hydrogen, and for the 2-biphenyl compounds, $R^1$ is preferably bromide or chloride, methyl or ethyl or ($C_9$–$C_{13}$)alkyl, and $R^2$ is preferably alkyl. In the most active compounds provided herein, as evidenced by in vitro binding assays, $R^1$ is bromide or chloride or, in instances in which $ET_B$ selectivity is desired, $C_9$–$C_{13}$ alkyl. $R^1$ is preferably halide, lower alkyl, particularly $CH_3$, or $C_9H_{19}$—$C_{13}H_{27}$.

In preferred embodiments, in which the sulfonamides are biphenylsulfonamides in which $R^1$ is halide; $R^2$ is selected from alkyl, lower alkenyl, lower alkynyl, lower haloalkyl and H; and the others of $R^3$–$R^7$ that are not phenyl are selected from H, lower alkyl, haloalkyl and halide. In preferred of these embodiments, $R^1$ is Cl or Br, and for the 3-biphenylsulfonamides and, particularly, the 4-biphenylsulfonamides, $R^1$ is also $CH_3$; $R^2$ is selected from H, $CH_3$, $C_2H_5$, $CF_3$, $C_2F_5$, n-$C_3H_7$ and cyclo-$C_3H_7$; and $R^{26}$ and $R^{13}$ are each independently selected from H, halide, $NH_2$, $CF_3$ $CH_3$, CN, $CH_3$, $(CH_3)_3C$, $C_5H_{11}$, $CH_3O$, n-$C_4H_9O$ and $CH_2$=CH.

In yet more preferred embodiments, $R^2$ is H, $CH_3$, $C_2H_5$, or $CF_3$; $R^3$–$R^7$ are independently selected from H, $CH_3$, $C_2H_5$, $CF_3$, and halide; and X is O.

In another preferred embodiment, the biphenylsulfonamides are 3- or 4-biphenylsulfonamides, in which $R^4$ and $R^5$ are other than hydrogen. In such instances $R^1$ is preferably, halide or methyl or higher ($C_9$–$C_{13}$) alkyl. Such compounds have a higher $ET_B$ affinity than the 2-biphenylsulfonamides. It is also preferred that the substituent at the 2-position is hydrogen. $R^1$ is selected from halide, $CH_3$, $C_2H_5$, $CF_3$, $C_2F_5$, n-$C_3H_7$ and cyclo-$C_3H_7$, preferably halide or $CH_3$, and $R^2$ is selected from H, $CH_3$, $C_2H_5$, $CF_3$, $C_2F_5$, n-$C_3H_7$ and cyclo-$C_3H_7$; and $R^3$–$R^7$ are each independently selected from H, halide, $NH_2$, $CF_3$ $CH_3$, CN, $CH_3$, $(CH_3)_3C$, $C_5H_{11}$, $CH_3O$, n-$C_4H_9O$ and $CH_2$=CH. In more preferred of these embodiments, $R^1$ is halide or $CH_3$, and $R^2$ are selected from H, $CH_3$, $C_2H_5$, or $CF_3$; $R^3$–$R^7$ are independently selected from H, $CH_3$, $C_2H_5$, $CF_3$, and halide.

When $Ar^2$ is a biphenyl (n=0) in which $R^4$ and $R^5$ are other than hydrogen, the compounds are (4-halo-isoxazolyl)sulfonamides or are (4-higher alkyl-isoxazolyl)sulfonamides, in which the alkyl group contains more than about 8, preferably 9 to 15, more preferably 9 to 13, carbon atoms.

In embodiments described in detail herein, preferred compounds include compounds that are $ET_B$ receptor selective or that bind to $ET_B$ receptors with an $IC_{50}$ of less than about 1 $\mu$M (when measured in the assays herein at 4° C.). In these compounds, $Ar^2$ is 3-biphenyl, 4-biphenyl and $R^1$ is halide or preferably higher alkyl ($C_9H_{19}$ to $C_{13}H_{27}$). $R^2$ is selected from among alkyl, lower haloalkyl, H; and $R^1$ is halide, lower alkyl or lower haloalkyl, or, when $Ar^2$ is phenyl or naphthyl, $R^1$ is higher alkyl (nine or more carbon atoms, preferably 9 to 13 carbon atoms). When $R^4$ or $R^5$ are other than hydrogen, then $Ar^1$ is 4-haloisoxazolyl or 4-higher ($C_8$ to $C_{15}$, preferably $C_9H_{19}$ to $C_{13}H_{27}$) alkyl-isoxzaolyl are preferred.

Among the above phenyl and biphenyl compounds, are compounds with the following formulae (V):

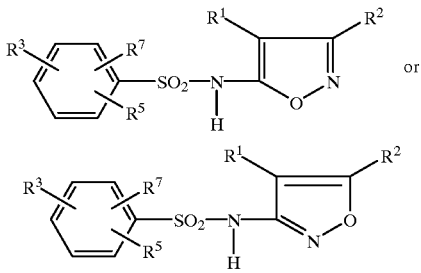

in which $R^3$, $R^5$ and $R^7$ are each independently selected as follows, with the proviso that at least one of $R^3$, $R^5$ and $R^7$ is phenyl or phenoxy:
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with $W^1$, $W^2$ and $W^3$;
(c) halo;
(d) hydroxyl;
(e) cyano;
(f) nitro;
(g) —C(O)H or —C(O)$R^{27}$;
(h) —CO$_2$H or —CO$_2R^{27}$;
(i) —SH, —S(O)$_n R^{27}$, —S(O)$_m$—OH, —S(O)$_m$—OR$^{27}$, —S(O)$_m$OH, or —O—S(O)$_m$OR$^{27}$;
(j) —W$^4$NR$^{28}$R$^{29}$, except that, if one of $R^3$, $R^5$ and $R^7$ is 4-W$^4$NR$^{28}$R$^{29}$ then at least one of the other two of $R^3$, $R^5$ and $R^7$ is not hydrogen; or
(k) —W$^4$N(R$^{32}$)—W$^5$N R$^{30}$R$^{31}$;

$R^1$ and $R^2$ are each independently selected from:
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with $W^1$, $W^2$ and $W^3$;
(c) hydroxyl;
(d) cyano;
(e) nitro;
(f) —C(O)H or —C(O)$R^{27}$;
(g) —CO$_2$H or —CO$_2R^{27}$;
(h) —SH, —S(O)$_n R^{27}$, —S(O)$_m$—OH, —S(O)$_m$OR$^{27}$, —O—S(O)$_m$—R$^{27}$, —O—S(O)$_m$OH, or —O—S(O)$_m$—OR$^{27}$;
(i) W$^4$ NR$^{28}$R$^{29}$; or
(j) —W$^4$N(R$^{32}$)—W$^5$—NR$^{30}$R$^{31}$;

$R^1$ is selected with the proviso that when $Ar^2$ is a 3- or 4-biphenyl in which the substituent at the 2-position is other than hydrogen or when the compounds are 2-biphenyls, then $R^1$ is halide or higher allyl ($C_8H_{17}$ to $C_{15}H_{31}$, preferably $C_9H_{19}$ to $C_{13}H_{27}$);

$R^{27}$ is alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{28}$ is
(a) hydrogen;
(b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;
(c) cyano;
(d) hydroxyl;
(e) —C(O)H or —C(O)$R^{27}$;
(f) —CO$_2R^{27}$;
(g) —SH, —S(O)$_n R^{27}$, —S(O)$_m$—OH, —S(O)$_m$—OR$^{27}$, —O—S(O)$_m$—R$^{27}$, —O—S(O)$_m$OH, or —O—S(O)$_m$—OR$^{27}$ except when W4 is —S(O)$_n$—;

$R^{29}$ is
(a) hydrogen;
(b) —C(O)H or —C(O)$R^{27}$, except when $W^4$ is —C(O)— and $R^{28}$ is —C(O)H, —C(O)$R^{27}$, or —CO$_2R^{27}$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$; or $R^{28}$ and $R^{29}$ together are alkylene or alkenylene (either of which may be substituted with $W^1$, $W^2$ and $W^3$), completing a 3- to 8-membered saturated, unsaturated or aromatic ring together with the nitrogen atom to which they are attached;

$R^{30}$ is
(a) hydrogen;
(b) hydroxyl;
(c) —C(O)H or —C(O)$R^{27}$;
(d) —CO$_2R^{27}$;
(e) —SH, —S(O)$_n R^{27}$, —S(O)$_m$—OH, —S(O)$_m$—OR$^{27}$, —O—S(O)$_m$—R$^{27}$, —O—S(O)$_m$OH, or —O—S(O)$_m$—OR$^{27}$;
(f) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{31}$ is
(a) hydrogen;
(b) —C(O)H or —C(O)$R^{27}$, except when $W^5$ is —C(O)— and $R^{30}$ is —C(O)H, —C(O)$R^{27}$, or —CO$_2R^{27}$; or
(c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{32}$ is
(a) hydrogen;
(b) hydroxyl
(c) —C(O)H, —C(O)$R^{27}$ or CO$_2R^{27}$; or
(d) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

or any two of $R^{30}$, $R^{31}$ and $R^{32}$ together are alkylene or alkenylene (either of which may be substituted with $W^1$, $W^2$ and $W^3$), completing a 3- to 8-membered saturated, unsaturated or aromatic ring together with the atoms to which they are attached; $W^1$, $W^2$ and $W^3$ are each independently
(a) hydrogen;
(b) halo;
(c) hydroxy;
(d) alkyl;
(e) alkenyl;
(f) aralkyl;

(g) alkoxy;
(h) aryloxy;
(i) aralkoxy;
(j) —SH, —S(O)$_n$W$^6$, —S(O)$_m$—OH, —S(O)$_m$—OW$^6$, —O—S(O)$_m$—W$^6$, —O—S(O)$_m$OH, or —O—S(O)$_m$—OW$^6$;
(k) oxo;
(l) nitro;
(m) cyano;
(n) —C(O)H or —C(O)W$^6$;
(o) —CO$_2$H or —CO$_2$W$^6$;
(p) —W$^4$-NW$^7$W$^8$;
(q) W$^4$—N(W$^{11}$)—W$^5$—W$^6$; or
(r) —W$^4$—N(W$^{11}$)—W$^5$—NW$^7$W$^8$;

W$^4$ and W$^5$ are each independently
(a) a single bond;
(b) —W$^9$—S(O)$_n$—W$^{10}$;
(c) —W$^9$—C(O)—W$^{10}$;
(d) —W$^9$—C(S)—W$^{10}$;
(e) —W$^9$—O—W$^{10}$;
(f) —W$^9$—S—W$^{10}$—; or
(g) —W$^9$—O—C(O)—W$^{10}$—;

W$^6$, W$^7$ and W$^8$ are each independently hydrogen, alkyl, alkenyl, alkynyl, cycloalkyl, cycloalkylalkyl, cycloalkenyl, cycloalkenylalkyl, aryl, or aralkyl, or W$^7$ and W$^8$ together are alkylene or alkenylene, completing a 3- to 8-membered saturated, unsaturated or aromatic ring together with the nitrogen atom to which they are attached;

W$^9$ and W$^{10}$ are each independently a single bond, alkylene, alkenylene, or alkynylene;

W$^{11}$ is
(a) hydrogen;
(b) hydroxyl;
(c) —C(O)H, —C(O)W$^6$ or —CO$_2$W$^6$;
(d) alkyl, alkenyl, alkynyl, alkoxy, cycloalkyl, cycloalkylalkyl, cycloalkenyl, cycloalkenylalkyl, aryl, or aralkyl;

or any two of W$^7$ and W$^8$ and W$^{11}$ together are alkylene or alkenylene, completing a 3- to 8-membered saturated, unsaturated, or aromatic ring together with the atoms to which they are attached;

m is 1 or 2; and
n is 0, 1, or 2,
with the proviso that (i) R$^2$ is not halide; and (ii) unless R$^5$ is hydrogen, R$^1$ is halide or is higher alkyl (greater than about 8 carbons up to 15 carbons in the chain, preferably nine to thirteen carbons).

If R$^5$ is hydrogen, then R$^1$ is also preferably selected from lower alkyl, preferably methyl or ethyl, halide or higher alkyl.

Preferred compounds among these include those in which one of R$^3$, R$^5$ or R$^7$ is phenyl. Preferred substituents on the rings are lower alkyl, particular methyl, ethyl, and propyl, halide, amino, dimethylamino, and methoxy. In addition, in preferred compounds R$^1$ is preferably halide or higher alkyl.

In more preferred compounds, R$^1$ is Cl or Br, or if greater ET$_B$ activity is preferred a higher alkyl (C$_9$H$_{19}$ to C$_{13}$H$_{27}$; R$^2$ is selected from H, CH$_3$, C$_2$H$_5$, CF$_3$, C$_2$F$_5$, n-C$_3$H$_7$, cyclo-C$_3$H$_7$, nC$_{13}$H$_{27}$ and nC$_9$H$_{19}$; and R$^3$, R$^5$, and R$^7$ are each independently selected from H, halide, NH$_2$, CF$_3$, Ph and CH$_3$; R$^3$ is selected from H, NHOH, NH$_2$, C$_2$H$_5$NH, (CH$_3$)$_2$N, Ph—CH$_2$NH, NO$_2$, F, Cl, Br, I, CN, CH$_3$, (CH$_3$)$_3$C, C$_5$H$_{11}$, CH$_3$O, n-C$_4$H$_9$O, CH$_2$=CH, Ph—CH=CH, CH≡C, Ph—C≡C, Ph, 3-(ethyoxycarbonylmethyl)ureido, and 3-cyclohexylureido, with the proviso that at least one of R$^3$, R$^5$, and R$^7$ is a substituted or unsubstituted phenyl. Preferred substituents are lower alkyl, alkoxy(lower)alkyl, halide, and the like. Preferred positions for the substituents are ortho and/or para.

In yet more preferred embodiments, R$^1$ is Br, Cl or C$_9$H$_{19}$ to C$_{13}$H$_{27}$; R$^2$ is H, CH$_3$, C$_2$H$_5$, or CF$_3$; and R$^3$, R$^5$ and R$^7$, with the proviso that at least one of R$^3$, R$^5$ and R$^7$ is phenyl, are selected as follows:

R$^3$ is H, Ph, NH$_2$, CH$_3$, CF$_3$, halide or C$_2$H$_5$NH; R$^5$ is selected from H, CH$_3$, C$_2$H$_5$, (CH$_3$)$_2$CH, CF$_3$, halide, particularly Br and Cl, NH$_2$ or Ph; and R$^7$ is H, Ph, CH$_3$, CH$_2$CH$_3$, (CH$_3$)$_2$CH, F or CF$_3$.

Of any of these compounds described above, those with formulae VI:

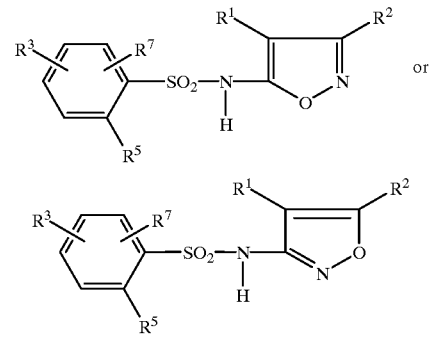

in which R$^5$ is hydrogen are more preferred. In these compounds R$^3$ and R$^7$ are each independently selected as follows, with the proviso that one of R$^3$ and R$^7$ is phenyl or phenoxy, preferably phenyl and the other is:
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with W$^1$, W$^2$ and W$^3$;
(c) halo;
(d) hydroxyl;
(e) cyano;
(f) nitro;
(g) —C(O)H or —C(O)R$^{27}$;
(h) —CO$_2$H or —CO$_2$R$^{27}$;
(i) —SH, —S(O)$_n$R$^{27}$, —S(O)$_m$—OH, —S(O)$_m$—OR$^{27}$, —O—S(O)$_m$OH, or —O—S(O)$_m$OR$^{27}$;
(j) —W$^4$NR$^{28}$R$^{29}$, except that, if one of R$^3$, R$^5$ and R$^7$ is 4-W$^4$NR$^{28}$R$^{29}$ then at least one of the other two of R$^3$, R$^5$ and R$^7$ is not hydrogen; or
(k) —W$^4$N(R$^{32}$)—W$^5$NR$^{30}$R$^{31}$;

R$^1$ and R$^2$ are each independently selected from:
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with W$^1$, W$^2$ and W$^3$;
(c) hydroxyl;
(d) cyano;
(e) nitro;
(f) —C(O)H or —C(O)R$^{27}$;
(g) —CO$_2$H or —CO$_2$R$^{27}$;
(h) —SH, —S(O)$_n$R$^{27}$, —S(O)$_m$—OH, —S(O)$_m$OR$^{27}$, —O—S(O)$_m$—R$^{27}$, —O—S(O)$_m$OH, or —O—S(O)$_m$—OR$^{27}$;
(i) —W$^4$—NR$^{28}$R$^{29}$; or
(j) —W$^4$N(R$^{32}$)—W$^5$—NR$^{30}$R$^{31}$;

R$^{27}$ is alkyl, alkenyl, alkynyl, alkoxy, cycloalkyl, cycloalkylalkyl, cycloalkenyl, cycloalkenylalkyl, aryl, or aralkyl, any of which may be substituted with W$^1$, W$^2$ and W$^3$;

$R^{28}$ is
(a) hydrogen;
(b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;
(c) cyano;
(d) hydroxyl;
(e) —C(O)H or —C(O)$R^{27}$;
(f) —CO$_2R^{27}$;
(g) —SH, —S(O)$_nR^{27}$, —S(O)$_m$—OH, —S(O)$_m$—O$R^{27}$, —S(O)$_m$—$R^{27}$, —O—S(O)$_m$OH, or —O—S(O)$_m$—O$R^{27}$, except when W4 is —S(O)$_n$—;

$R^{29}$ is
(a) hydrogen;
(b) —C(O)H or —C(O)$R^{27}$, except when $W^4$ is —C(O)— and $R^{28}$ is —C(O)H, —C(O)$R^{27}$, or —CO$_2R^{27}$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$; or $R^{28}$ and $R^{29}$ together are alkylene or alkenylene (either of which may be substituted with $W^1$, $W^2$ and $W^3$), completing a 3- to 8-membered saturated, unsaturated or aromatic ring together with the nitrogen atom to which they are attached;

$R^{30}$ is
(a) hydrogen;
(b) hydroxyl;
(c) —C(O)H or —C(O)$R^{27}$;
(d) —CO$_2R^{27}$;
(e) —SH, —S(O)$_nR^{27}$, —S(O)$_m$—OH, —S(O)$_m$—O$R^{27}$, —O—S(O)$_m$-$R^{27}$, —O—S(O)$_m$OH, or —O—S(O)$_m$—O$R^{27}$;
(f) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{31}$ is
(a) hydrogen;
(b) —C(O)H or —C(O)$R^{27}$, except when $W^5$ is —C(O)— and $R^{30}$ is —C(O)H, —C(O)$R^{27}$, or —CO$_2R^{27}$; or
(c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{32}$ is
(a) hydrogen;
(b) hydroxyl
(c) —C(O)H, —C(O)$R^{27}$ or CO$_2R^{27}$; or
(d) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

or any two of $R^{30}$, $R^{31}$ and $R^{32}$ together are alkylene or alkenylene (either of which may be substituted with $W^1$, $W^2$ and $W^3$), completing a 3- to 8-membered saturated, unsaturated or aromatic ring together with the atoms to which they are attached; $W^1$, $W^2$ and $W^3$ are each independently
(a) hydrogen;
(b) halo;
(c) hydroxy;
(d) alkyl;
(e) alkenyl;
(f) aralkyl;
(g) alkoxy;
(h) aryloxy;
(i) aralkoxy;
(j) —SH, —S(O)$_nW^6$, —S(O)$_m$—OH, —S(O)$_m$—O$W^6$, —O—S(O)$_m$—$W^6$, —O—S(O)$_m$OH, or —O—S(O)$_m$—O$W^6$;
(k) oxo;
(l) nitro;
(m) cyano;
(n) —C(O)H or —C(O)$W^6$;
(o) —CO$_2$H or —CO$_2W^6$;
(p) —$W^4$—N$W^7W^8$;
(q) $W^4$—N($W^{11}$)—$W^5$—$W^6$; or
(r) —$W^4$—N($W^{11}$)—$W^5$—N$W^7W^8$;

$W^4$ and $W^5$ are each independently
(a) a single bond;
(b) —$W^9$—S(O)$_n$—$W^{10}$—;
(c) —$W^9$—C(O)—$W^{10}$—;
(d) —$W^9$—C(S)—$W^{10}$—;
(e) —$W^9$—O—$W^{10}$—;
(f) —$W^9$—S—$W^{10}$—; or
(g) —$W^9$—O—C(O)—$W^{10}$;

$W^6$, $W^7$ and $W^8$ are each independently hydrogen, alkyl, alkenyl, alkynyl, cycloalkyl, cycloalkylalkyl, cycloalkenyl, cycloalkenylalkyl, aryl, or aralkyl, or $W^7$ and $W^8$ together are alkylene or alkenylene, completing a 3- to 8-membered saturated, unsaturated or aromatic ring together with the nitrogen atom to which they are attached;

$W^9$ and $W^{10}$ are each independently a single bond, alkylene, alkenylene, or alkynylene;

$W^{11}$ is
(a) hydrogen;
(b) hydroxyl;
(c) —C(O)H, —C(O)$W^6$ or —CO$_2W^6$;
(d) alkyl, alkenyl, alkynyl, alkoxy, cycloalkyl, cycloalkylalkyl, cycloalkenyl, cycloalkenylalkyl, aryl, or aralkyl;

or any two of $W^7$ and $W^8$ and $W^{11}$ together are alkylene or alkenylene, completing a 3- to 8-membered saturated, unsaturated, or aromatic ring together with the atoms to which they are attached;

m is 1 or 2; and
n is 0, 1, or 2.

In the more preferred of these compounds, $R^1$, $R^2$, $R^3$ and $R^7$ are selected as in the more preferred compounds of formulae (V). Most preferred are compounds in which Ar$^2$ is 4-biphenyl.

The biphenyl compounds provided herein are generally ET$_B$ active or ET$_B$ selective (see, e.g., Table 2); i.e. the compounds provided herein inhibit binding of endothelin to ET$_B$ receptors at concentrations about 10- to about 30-fold less than they inhibit binding of endothelin to ET$_A$ receptors. In particular the 4-biphenylsulfonamides are ET$_B$ selective.

In general in all embodiments herein, 4-haloisoxazolyl sulfonamides exhibit substantially enhanced activity with respect to at least one of the ET receptors (about two-fold to twenty-fold greater activity), as assessed by assays, such as those provided herein, that measure binding to ET$_A$ and/or ET$_B$ receptors, compared to corresponding sulfonamides in which the substituent at the 4 position in the isoxazolyl is other than halo, such as alkyl. For example: the IC$_{50}$ of N-(3,4-dimethyl-5-isoxazolyl)-2-biphenylsulfonamide for ET$_A$ receptors is about 0.008 μM, whereas, the IC$_{50}$ of N-(4-bromo-3-methyl-5-isoxazolyl)-2-biphenylsulfonamide is about 0.0016 µM (see, Table below); and (3) the $IC_{50}$ of N-(3,4-dimethyl-5-isoxazolyl)-3-biphenylsulfonamide for $ET_B$ receptors is about 3.48 µM; whereas, the $IC_{50}$ of N-(4-bromo-3-methyl-5-isoxazolyl)-3-biphenylsulfonamide for $ET_B$ receptors is about 0.76 µM and the $IC_{50}$ of N-(4-chloro-3-methyl-5-isoxazolyl)-3-biphenylsulfonamide for $ET_B$ receptors is about 0.793 µM (see, Table below).

Exemplary biphenyl sulfonamides are the following and those set forth in Table 2, and include, but are not limited to: N-(4-bromo-3-methyl-5-isoxazolyl)-4-biphenylsulfonamide, N-(4-chloro-3-methyl-5-isoxazolyl)-4-biphenylsulfonamide, N-(4-bromo-5-methyl-3-isoxazolyl)-4-biphenylsulfonamide, N-(4-chloro-5-methyl-3-isoxazolyl)-4-biphenylsulfonamide, N-(3-methyl-5-isoxazolyl)-4'-methylphenyl-4-biphenylsulfonamide, N-(4-bromo-3-methyl-5-isoxazolyl)-4'-methylphenyl-4-biphenylsulfonamide, N-(4-chloro-3-methyl-5-isoxazolyl)-4'-methylphenyl-4-biphenylsulfonamide, (3-methyl-5-isoxazolyl)-4'-trifluorophenyl-4-biphenylsulfonamide, (4-bromo-3-methyl-5-isoxazolyl)-4'-trifluorophenyl-4-biphenylsulfonamide, (3-methyl-5-isoxazolyl)-4'-methyoxyphenyl-4-biphenylsulfonamide, (4-bromo-3-methyl-5-isoxazoly-)-4'-methoxyphenyl-4-biphenylsulfonamide, (4-bromo-3-methyl-5-isoxazolyl)-3'-methoxyphenyl-4-biphenylsulfonamide, (4-bromo-3-methyl-5-isoxazolyl)-2'-methoxyphenyl-4-biphenylsulfonamide, N-(4-bromo-3-methyl-5-isoxazolyl)-3',4'-methylenedioxyphenyl-4-biphenylsulfonamide and (4-bromo-3-methyl-5-isoxazolyl)-3'-methylphenyl-4-biphenylsulfonamide. Corresponding 4-chloro and 4-fluoro isoxazolyl compounds are also encompassed herein.

Exemplary biphenyl compounds were tested using the exemplified assays (see, EXAMPLES) and the results, which are intended to be exemplary and not limiting, are as set forth in the following table (Table 2):

TABLE 2

| COMPOUND | $ET_A$ (µM)* | $ET_B$ (µM)* |
| --- | --- | --- |
| N-(4-bromo-3-methyl-5-isoxazolyl)-4-biphenylsulfonamide | 3.3<br>49† | ~0.17<br>1.23† |
| N-(4-bromo-5-methyl-3-isoxazolyl)-4-biphenylsulfonamide | 6.4 ± 2<br>49† | 0.29 ± 0.02<br>1.78† |
| N-(4-chloro-3-methyl-5-isoxazolyl)-4-biphenylsulfonamide | 4.93 ± 3 | 0.29 ± 0.1 |
| N-(3,4-dimethyl-5-isoxazolyl)-4-biphenylsufonamide | 9.9 ± 1.4<br>6.3† | 0.77 ± 0.32<br>0.15† |
| N-(4-chloro-5-methyl-3-isoxazolyl)-4-biphenylsulfonamide | 3.7<br>18.6† | 0.23 ± 0.01<br>1.29† |
| N-(4-Methyl-3-trifluoromethyl-5-isoxazolyl)-4-biphenylsulfonamide | 19.0<br>— | 1.7<br>5.62† |
| N-(4-Tridecyl-3-trifluoromethyl-5-isoxazolyl)-4-biphenylsulfonamide | 34.0 ± 9??<br>33.0† | 0.99 ± 0.2??<br>0.95† |
| N-(3,4-dimethyl-5-isoxazolyl)-2-biphenylsulfonamide | 0.0083 ± 0.0014 | 12.8 |
| N-(4-chloro-3-methyl-5-isoxazolyl)-2-biphenylsulfonamide | 0.00123** | ~14** |
| N-(4-chloro-3-methyl-5-isoxazolyl)-2-biphenylsulfonamide | 0.00123** | ~14** |
| N-(3,4-dimethyl-5-isoxazolyl)-3-biphenylsulfonamide | >0.03** | 3.48** |
| N-(4-bromo-3-methyl-5-isoxazolyl)-3-biphenylsulfonamide | ~0.03** | 0.76** |
| N-(4-chloro-3-methyl-5-isoxazolyl)-3-biphenylsulfonamide | >0.03** | 0.793** |
| N-(3-methyl-5-isoxazolyl)-4'-methylphenyl-4-biphenylsulfonamide | >100 | 3.2 ± 0.36 |
| N-(4-bromo-3-methyl-5-isoxazolyl)-4'-methylphenyl-4-biphenylsulfonamide | 14.53 ± 9.6<br>22.17 ± 3.77† | 0.046 ± 0.044<br>0.168 ± 0.0032† |
| N-(4-chloro-3-methyl-5-isoxazolyl)-4'-methylphenyl-4-biphenylsulfonamide | — | — |
| (3-methyl-5-isoxazolyl)-4'-trifluorophenyl-4-biphenylsulfonamide | 72 | 5.6 ± 1.0 |
| (4-bromo-3-methyl-5-isoxazolyl)-4'-trifluorophenyl-4-biphenylsulfonamide | 5.4 ± 0.3<br>25.9 ± 13.7† | 0.083 ± 0.02<br>0.71 ± 0.43† |
| (3-methyl-5-isoxazolyl)-4'-methyoxyphenyl-4-biphenylsulfonamide | — | 78 |
| (4-bromo-3-methyl-5-isoxazolyl)-4'-methoxyphenyl-4-biphenylsulfonamide | 14.7 ± 5.6<br>121.5 ± 2.12† | 1.15 ± 0.44<br>3.94 ± 0.89† |
| (4-bromo-3-methyl-5-isoxazolyl)-3'-methoxyphenyl-4-biphenylsulfonamide | 4.97 ± 3.4<br>162.6 ± 7.14† | 0.66 ± 0.25<br>2.08 ± 0.23† |
| (4-bromo-3-methyl-5-isoxazolyl)-2'-methoxyphenyl-4-biphenylsulfonamide | 3.3 ± 3.5 | 0.41 ± 0.14 |
| N-(4-bromo-3-methyl-5-isoxazolyl)-3',4'-methylenedioxyphenyl-4-biphenylsulfonamide | 38.2 ± 4.95† | 3.0 ± 0.78† |
| (4-bromo-3-methyl-5-isoxazolyl)-3'-methylphenyl-4-biphenylsulfonamide | — | — |

*results generally from 1, 2 or 3 experiments with the same preparation
**preliminary results The preparation of the above and other compounds that possess the requisite activities are set forth in the Examples.

2. $Ar^2$ is Fused Ring Carbocycle or Heterocycle, Including Dibenzofuryl, Dibenzothiophenyl, Dibenzopyrrolyl and Phenanthrene Compounds in $Ar^2$ is a carbocycle containing two or more fused rings or a heterocycle with one heteroatom and two or more fused rings are provided. The heteroatom is O, S or N ($NR^{14}$) and $Ar^2$ is selected from among, but not limited to, quinolyl, isoquinolyl, dibenzofuryl, dibenzothiophenyl, and dibenzopyrrolyl compounds and other such groups. The fused rings may be substituted with one or more substituents selected from among substituents set forth for $R^3$–$R^7$ or Z above, at any position. The sulfonamide portion of the compounds may be linked at any position on the rings.

In certain embodiments $Ar^2$ is dibenzofuryl, dibenzothiophenyl, dibenzopyrrolyl or phenanthrene or other tricyclic fused ring, and has the following formula (V):

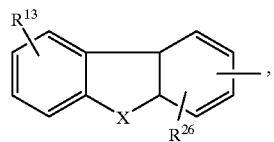

in which: $R^1$ and $R^2$ are selected as described above for the thiophenyl, furyl and pyrrolyl compounds; X is —CH=CH—, O, S, $NR^{14}$, in which $R^{14}$ is selected independently from the groups set forth above for $R^{11}$ (compounds in which X is —CH=CH— are phenanthrenesulfonamides); and $Ar^2$ is unsubstituted or substituted with one or more substituents selected from $R^{13}$ and $R^{26}$, which are each independently (i) or (ii):

(i) $R^{26}$ and $R^{13}$ are independently selected from H, OH, OHNH, $NH_2$, $NO_2$, halide, pseudohalide, alkyl, alkenyl, alkynyl, aryl, arylalkyl, heteroaryl, alkoxy, alkylamino, dialkylamino, alkylthio, haloalkoxy, haloalkyl, alkylsulfinyl, alkylsulfonyl, aryloxy, arylamino, arylthio, arylsulfinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, preferably from 1 to 6 atoms, and are either straight or branched chains or cyclic, and the aryl portions contain from about 4 to about 16 carbons, preferably 4 to 10 carbons; or (ii) $R^{26}$ and $R^{13}$ together are —$CH_2$—, —CH=$CH_2$—, O, S, $NR^{11}$ in which $R^{11}$ is as defined above, and is preferably, H or alkyl, particularly lower alkyl. It is understood that in either (i) or (ii) each ring of $Ar^2$ may be unsubstituted or substituted with more than one substituent, each of which is selected independently from the selections set forth in (i) for $R^{26}$ and $R^{13}$.

These compounds, thus, include fused tricyclic-substituted sulfonamides, dibenzothiophenesulfonamides, dibenzofuransulfonamides, dibenzopyrrolesulfonamides (carbazolesulfonamides) and phenanthrenesulfonamides.

In more preferred embodiments, $R^1$ is halide or methyl; $R^2$ is selected from lower alkyl, lower alkenyl, lower alkynyl and lower haloalkyl; $R^{26}$ and $R^{13}$ are independently selected from H, lower alkyl, haloalkyl and halide. In more preferred embodiments $R^1$ is Cl, Br or $CH_3$; $R^2$ is selected from H, $CH_3$, $C_2H_5$, $CF_3$, n-$C_3H_7$, cyclo-$C_3H_7$ and $C_4H_9$; and $R^{26}$ and $R^{13}$ are each independently selected from H, halide, $NH_2$, $CF_3$, $CH_3$, CN, $CH_3$, $(CH_3)_3C$, $C_5H_{11}$, $CH_3O$, n-$C_4H_9O$ and $CH_2$=CH. In yet more preferred embodiments, $R^2$ is H, $CH_3$, $C_2H_5$, or $CF_3$; $R^{26}$ and $R^{13}$ are independently selected from H, $CH_3$, $C_2H_5$, $CF_3$, and halide; and X is O.

Exemplary compounds include those set forth in Table 3:

TABLE 3

| COMPOUND | $ET_A$ ($\mu$M)* | $ET_B$ ($\mu$M)* |
|---|---|---|
| N-(4-bromo-3-methyl-5-isoxazolyl)dibenzofuran-4-sulfonamide | **0.39 | **10 |
| N-(3,4-dimethyl-5-isoxazolyl)-2-dibenzofuransulfonamide | — | — |
| N-(3,4-Dimethyl-5-isoxazolyl)-3-dibenzofuransulfonamide | 6.1 ± 1.2 | 0.81 ± 0.13 |
| N-(4-bromo-3-methyl-5-isoxazolyl)-3-dibenzofuransulfonamide | 1.05 ± 0.05 | 0.23 ± 0.05 |
| N-(3,4-dimethyl-5-isoxazolyl)dibenzothiophene-4-sulfonamide | 0.37 ± 0.06 | 1.8 ± 0.4 |
| N-(4-bromo-3-methyl-5-isoxazolyl)dibenzothiophene-4-sulfonamide | 0.115 ± 0.02 | 0.47 ± 0.13 |

*results based on 1 to 4 experiments

B. Preparation of the Compounds

The preparation of the above compounds is described in detail in the examples. Any such compound or similar compound may be synthesized according to a method discussed in general below and by only minor modification of the methods set forth in the Examples by selecting appropriate starting materials as exemplified.

In general, most of the syntheses involve the condensation of a sulfonyl chloride with an aminoisoxazole in dry pyridine or in tetrahydrofuran (THF) and sodium hydride. The sulfonylchlorides and aminoisoxazoles either can be obtained commercially or synthesized according to methods described in the Examples or using other methods available to those of skill in this art (see, e.g., U.S. Pat. Nos. 4,659,369, 4,861,366 and 4,753,672).

The compounds may be prepared by reacting an appropriate sulfonyl chloride with 5-aminoisoxazoles substituted at the 3 and 4 positions (or 4 and 5 positions in the case of 3-isoxazolyl derivatives), such as 5-amino-4-bromo-3-methylisoxazole, in tetrahydrofuran (THF) solution containing a base, such as sodium hydride. Following the reaction, the THF is removed under reduced pressure, the residue dissolved in water, acidified and extracted with methylene chloride. The organic layer is washed and then dried over anhydrous magnesium sulfate, the solvents are evaporated and the residue is purified by recrystallization using hexanes/ethyl acetate to yield pure product. The N-(4-haloisoxazolyl)sulfonamides can be prepared by condensation of amino-4-haloisoxazole with a sulfonyl chloride in THF with sodium hydride as a base.

In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

Alternatively, the sulfonamides can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

The N-(alkylisoxazolyl)sulfonamides can be prepared by condensing an aminoisoxazole with a sulfonyl chloride in dry pyridine with or without the catalyst 4-(dimethylamino)pyridine. The N-(3,4-dimethyl-5-isoxazolyl)sulfonamides and N-(4,5-dimethyl-5-isoxazolyl)sulfonamides can be prepared from the corresponding aminodimethylisoxazole, such as 5-amino-3,4-dimethylisoxazole. The N-(3,4-dimethyl-5-isoxazolylsulfonamides and the N-(4,5-dimethyl-3-isoxazolylsulfonamdies can be prepared from the corresponding aminodimethylisoxaole, such as 5-amino-3,4-dimethylisoxazole.

Exemplary preparations of numerous compounds herein are set forth in the Examples. For example compounds, such as N-(3,4-dimethyl-5-isoxazolyl)biphenylsulfonamide (EXAMPLE 1), can be prepared from 4-biphenylsulfonyl chloride and an amino-substituted isoxazole, such as 5-amino-3,4-dimethylisoxazole, in dry pyridine (2.0 ml). Following the reaction, the pyridine is removed under reduced pressure and the residue is partitioned between water and ethyl acetate. The organic layer is washed and then dried over anhydrous magnesium sulfate, the solvents are evaporated and the residue is purified by column chromatography over silica gel (e.g., 1% methanol in chloroform as eluent) to yielded a solid. Further purification is achieved by recrystallization from ethyl acetate/hexanes, to yield the pure product. Alternatively, the sulfonamides can be prepared from the corresponding aminoisoxazole in tetrahydrofuran solution containing sodium hydride.

The compounds, such as N-(3,4-dimethyl-5-isoxazolyl)-2-dibenzofuransulfonamide (see, em, EXAMPLE 3) can be prepared by reacting 5-amino-3,4-dimethylisoxazole and 2-dibenzofuransulfonyl chloride in dry pyridine. Following the reaction, the pyridine is removed under reduced pressure and the residue is partitioned between water and ethyl acetate. The organic layer is washed and then dried over anhydrous magnesium sulfate, the solvents are evaporated and the residue is purified by column chromatography over silica gel (e.g., 1% methanol in chloroform as eluent) to yield a solid. Further purification is achieved by recrystallization from ethyl acetate/hexanes or column chromatography, to yield the pure product.

Prodrugs and other derivatives of the compounds suitable for administration to humans may also be designed and prepared by methods known to those of skill in the art (see, e.g., Nogrady (1985) *Medicinal Chemistry A Biochemical Approach*, Oxford University Press, New York, pages 388–392.

Compounds listed and described have been synthesized and tested for activity in in vitro assays and, in some cases, in vivo animal models. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All of the compounds exemplified or described herein exhibited activity as endothelin antagonists.

C. Evaluation of the Bioactivity of the Compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those of specifically identified herein, that are endothelin antagonists or agonists may be identified using such screening assays.

1. Identifying Compounds that Modulate the Activity of an Endothelin Peptide

The compounds are tested for the ability to modulate the activity of endothelin-1. Numerous assays are known to those of skill in the art for evaluating the ability of compounds to modulate the activity of endothelin (see, e.g.., U.S. Pat. No. 5,114,918 to Ishikawa et al.; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., U.S. Pat. No. 5,114,918 to Ishikawa et al.; EP A1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., Tissue selectivity of endothelin, *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al; and EP A1 0 436 189 to BANYU PHARMACEUTICAL CO., LTD (Oct. 7, 1991); see, also Bolger et al. (1983) *J. Pharmacol. Exp. Ther.* 225 291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin"

*Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. No. 5,248,807; U.S. Pat. No. 5,240,910; U.S. Pat. No. 5,198,548; U.S. Pat. No. 5,187,195; U.S. Pat. No. 5,082,838; U.S. Pat. No. 5,230,999; published Canadian Application Nos. 2,067,288 and 2071193; published Great Britain Application No. 2,259, 450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of Endothelin Receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptors subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and Administration of the Compositions

Effective concentrations of one or more of the sulfonamide compounds of formula I or II or pharmaceutically acceptable salts, esters or other derivatives thereof are mixed with a suitable pharmaceutical carrier or vehicle.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelin-mediated disease. Typically, the compositions are formulated for single dosage administration.

Upon mixing or addition of the sulfonamide compound (s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 ng/ml to about 50–100 $\mu$g/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 μM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1
N-(3,4-Dimethyl-5-isoxazolyl)-4-biphenylsulfonamide (a) 4-Biphenylsulfonyl Chloride 4-Biphenylsulfonic acid (3.0 g, 12.8 mmol) was heated at 70° C. with phosphorus oxychloride (1.30 ml, 14.0 mol) for 2 h. Excess phosphorus oxychloride was removed under reduced pressure. The residue was decomposed with ice water and extracted with ethyl acetate. The extract was washed with 5% sodium bicarbonate solution, dried over anhydrous magnesium sulfate and concentrated to yield 2.9 g of crude 4-biphenylsulfonyl chloride.

(b) N-(3,4-Dimethyl-5-isoxazolyl)-4-biphenylsulfonamide

The 4-biphenylsulfonyl chloride from step (a) was added to a solution of 5-amino-3,4-dimethylisoxazole (250 mg, 2.2 mmol) and 4-(dimethyl)aminopyridine (5 mg) in dry pyridine (2.0 ml). The reaction mixture was stirred at room temperature for 4 h. Pyridine was removed under reduced pressure and the residue was partitioned between water and ethyl acetate. The organic layer was washed with 1N HCl (2×25 ml), brine (25 ml) and dried over anhydrous magnesium sulfate. Evaporation of the solvents left an oily residue that, after purification by column chromatography over silica gel (1% methanol in chloroform as eluent), yielded 337 mg (45%) of a white solid. Recrystallization from ethyl acetate/hexanes gave white crystals, m.p. 154–155° C.

EXAMPLE 2
N-(4-Bromo-3-methyl-5-isoxazolyl)-4-biphenylsulfonamide (a) 5-Amino-4-bromo-3-methylisoxazole 5-Amino-3-methylisoxazole (0.98 g, 10 mmol) was dissolved in chloroform (15 ml) and cooled to 0° C. N-Bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product, which was purified by column chromatography using 9:1, hexanes/ethyl acetate as the eluent, to give 5-amino-4-bromo-3-methylisoxazole (1.55 g, 87% yield).

(b) N-(4-Biphenylsulfonyl)-N-(4-bromo-3-methyl-5-isoxazolyl)-4-biphenylsulfonamide 5-Amino-4-bromo-3-methylisoxazole (0.179 g, 1.0 mmol) was dissolved in dry pyridine (2 ml). 4-Biphenylsulfonyl chloride (0.509 g, 2.2 mmol) was added with stirring at ambient temperature. N,N-dimethylaminopyridine (5 mg) was added, and stirring was continued at 50° C. for 16 h. The reaction mixture was diluted with dichloromethane (75 ml), washed with 1N HCl (2×50 ml) and the organic phase was dried over magnesium sulfate. The solvent was removed under reduced pressure to yield a crude product, which was purified by column chromatography using 8:2, hexanes/ethyl acetate, to give 0.390 g (60% yield) of N-(4-b phenylsulfonyl)-N-(4-bromo-3-methyl-5-isoxazolyl)-4-biphenylsulfonamide.

(c) N-(4-Bromo-3-methyl-5-isoxazolyl)-4-biphenylsulfonamide

N-(4-biphenylsulfonyl)-N-(4-bromo-3-methyl-5-isoxazolyl)-4-biphenylsulfonamide (0.150 g, 0.233 mmol) was dissolved in tetrahydrofuran (THF). Sodium hydroxide (0.120 g, 3.0 mmol) was added and the solution was warmed to 45° C. to dissolve the sodium hydroxide. Stirring was continued for 20 min. Tetrahydrofuran was removed under reduced pressure. The residue was dissolved in water, cooled to 0° C. and acidified to pH 3–4 with concentrated HCl. The solid precipitate was filtered off and dried in vacuo to give N-(4-bromo-3-methyl-5-isoxazolyl)-4-biphenylsulfonamide (94% yield), which was further purified by recrystallization from chloroform/hexanes, m.p. 133–1350 C.

EXAMPLE 3
N-(3,4-Dimethyl-5-isoxazolyl)-2-dibenzofuransulfonamide

N-(3,4-Dimethyl-5-isoxazolyl)-2-dibenzofuransulfonamide was prepared, using the method described in Example 1b, from 5-amino-3,4-dimethylisoxazole and 2-benzofuransulfonyl chloride in 32% yield. Purification was achieved by recrystallization from chloroform/hexanes to give a white "cotton-like" solid, m.p. 173–175° C. (dec.).

EXAMPLE 4
N-(4-Methyl-3-trifluoromethyl-5-isoxazolyl)-4-biphenylsulfonamide

N-(4-Methyl-3-trifluoromethyl-5-isoxazolyl)-4-biphenylsulfonamide was prepared in the same manner as described in Example 2b from 5-amino-4-methyl-3-trifluoromethyl-isoxazole and 4-biphenylsulfonyl chloride in 78% yield. Purification was achieved by recrystallization from methanol/water to give a white solid, m.p. 139–140° C.

EXAMPLE 5
N-(4-Tridecyl-3-trifluoromethyl-5-isoxazolyl)-4-biphenylsulfonamide N-(4-Tridecyl-3-trifluoromethyl-5-isoxazolyl)-4-biphenylsulfonamide was prepared, in the same manner as described in Example 2b, from 5-amino-4-tridecyl-3-trifluoromethyl-isoxazole and 4-biphenylsulfonyl chloride in 81% yield. Purification was achieved by recrystallization from methanol/water to give an off white solid, m.p. 115–116° C.

EXAMPLE 6
N-(4-Methyl-3-trifluoromethyl-5-isoxazolyl)-4-biphenylsulfonamide

N-(4-Methyl-3-trifluoromethyl-5-isoxazolyl)-4-biphenylsulfonamide was prepared, as described in Example 2, from 5-amino-4-methyl-3-trifluoromethylisoxazole and 4-biphenylsulfonyl chloride in 78% yield. Purification was achieved by recrystallization from ethyl acetate/hexanes to give a white solid, m.p. 139–140° C.

EXAMPLE 7
N-(4-Bromo-5-methyl-3-isoxazolyl)-4-biphenylsulfonamide (a) 3-Amino-4-bromo-5-methylisoxazole 3-Amino-5-methylisoxazole (1.96 g, 20 mmol) was dissolved in chloroform (10 ml) and cooled to 0° C. N-Bromosuccinimide (3.56 g, 20 mmol) was added in small portions over a period of 10 min. The stirring was continued for another 15 minutes at 0° C. The reaction mixture was diluted with chloroform (100 ml), washed with water (2×50 ml) and the organic layer was dried over magnesium sulfate. Removal of the solvent under reduced pressure gave the crude product, which was purified by column chromatography, using 9:1 hexanes/ethyl acetate as the eluent, to give 3-amino-4-bromo-5-methylisoxazole (1.40 g, 40% yield).

(b) N-(4-bromo-5-methyl-3-isoxazolyl)-4-biphenylsulfonamide

N-(4-bromo-5-methyl-3-isoxazolyl)-4-biphenylsulfonamide was prepared, using the method in Example 1b, from 3-amino-4-bromo-5-methylisoxazole and 4-biphenylsulfonyl chloride in 5% yield. The crude product was purified by column chromatography. After recrystallization from ethyl acetate/hexanes, N-(4-bromo-5-methyl-3-isoxazolyl)-4-biphenylsulfonamide (m.p. 154–156° C.) was obtained in 51% yield.

EXAMPLE 8

N-(4-Chloro-3-methyl-5-isoxazolyl)-4-biphenylsulfonamide (a) 5-Amino-4-chloro-3-methylisoxazole Using the method in Example 2a, 5-amino-4-chloro-3-methylisoxazole was prepared from 5-amino-3-methylisoxazole and N-chlorosuccinimide in 90% yield.

(b) N-(4-Chloro-3-methyl-5-isoxazolyl)-4-biphenylsulfonamide

Sodium hydride (188 mg, 4.4 mmol) was suspended in dry THF (1 ml) and cooled to 0° C. A solution of 5-amino-4-chloro-3-methylisoxazole (mg, mmol) in dry THF (1 ml) was added with stirring. Once the addition was complete, the reaction mixture was warmed to room temperature for 10 min. The solution was recooled to 0° C., and 4-biphenylsulfonyl chloride (0.283 ml, 2.2 mmol) was added. Stirring was continued at 25° C. for 2 h. Excess sodium hydride was decomposed by the addition of methanol (0.4 ml) followed by water (0.5 ml). The THF was removed under reduced pressure and the residue was dissolved in water (20 ml) and basified by addition of sodium hydroxide (pH 9–10). Neutral impurities were removed by extraction with ethyl acetate (2×10 ml). The aqueous layer was acidified to pH 2–3 using concentrated HCl and extracted with ethyl acetate (3×10 ml). The combined organic layer was dried over magnesium sulfate. Removal of the solvent gave N-(4-chloro-3-methyl-5-isoxazolyl)-4-biphenylsulfonamide in 83% yield. This product was purified by recrystallization from ethyl acetate/hexanes as a white solid, m.p. 129–132° C.

EXAMPLE 9

2,5-Dimethoxy-N-(4-bromo-3-methyl-5-isoxazolyl)benzenesulfonamide 2,5-Dimethoxy-N-(4-bromo-3-methyl-5-isoxazolyl)benzenesulfonamide was prepared from 5-amino-4-bromo-3-methylisoxazole and 2,5-dimethoxybenzenesulfonyl chloride according to the procedures described in Example 8 (see, also Example 30), below. The crude product was purified by recrystallization from ethyl acetate/hexanes to give a crystalline solid, m.p. 118–120°, yield 58%.

EXAMPLE 10

N-(4-bromo-3-methyl-5-isoxazolyl)-2-biphenylsulfonamide

A. 2-Biphenylsulfonyl Chloride

2-Bromobiphenyl (2.33 g, 10 mmol) was dissolved in ether (10 ml) and cooled to −78° C. n-Butyllithium (2.5 M solution in hexane, 4.8 ml, 12 mmol) was added dropwise under constant stirring and an argon atmosphere. The resultant reaction mixture was stirred at −70° C. to −60° C. for 1 h. The reaction mixture was cooled to −78° C. and sulfuryl chloride (0.88 ml, 11 mmol) was added dropwise. After addition, the reaction mixture was allowed to attain ambient temperature slowly and stirred for 1 h. The reaction mixture was diluted with ethyl acetate (50 ml), washed with water and the organic layer dried over anhydrous MgSO$_4$. Removal of the solvent under reduced pressure gave a crude product, which was purified by column chromatography, using hexane followed by 5% ethyl acetate in hexane as eluent, to give 2-biphenylsulfonyl chloride as a solid (1.3 g, 51% yield).

B. N-(4-bromo-3-methyl-5-isoxazolyl)-2-biphenylsulfonamide

N-(4-bromo-3-methyl-5-isoxazolyl)-2-biphenylsulfonamide was prepared in the same manner as described in Example 8b from 5-amino-4-bromo-3-methylisoxazole and 2-biphenylsulfonyl chloride in 71% yield. Purification was achieved by recrystallization from ethyl acetate/hexanes to give a crystalline solid, m.p. 145–147° C.

EXAMPLE 11

N-(4-Chloro-3-methyl-5-isoxazolyl)-2-biphenylsulfonamide

N-(4-Chloro-3-methyl-5-isoxazolyl)-2-biphenylsulfonamide was prepared in the same manner as described in Example 10 from 5-amino-4-chloro-3-methylisoxazole and 2-biphenylsulfonyl chloride in 74% yield. Purification was achieved by recrystallization from ethyl acetate/hexanes to give a crystalline solid, m.p. 132–134° C.

EXAMPLE 12

N-(4-Bromo-3-methyl-5-isoxazolyl)-3-biphenylsulfonamide

A. 3-Biphenylsulfonyl Chloride

3-Bromobiphenyl (1.5 g, 6.4 mmol) was dissolved in ether (15 ml) and cooled to −78° C. t-Butyllithium (1.7 M solution in hexane, 3.8 ml, 6.4 mmol) was added dropwise under constant stirring and an argon atmosphere. The resultant reaction mixture was stirred at −10° C. to −5° C. for 6 h. The reaction mixture was cooled to −78° C. and sulfuryl chloride (0.64 ml, 6.4 mmol) was added dropwise. After completion of the addition, the reaction mixture was allowed to attain ambient temperature slowly and stirred for 1 h. The reaction mixture was diluted with ethyl acetate (50 ml), washed with water and the organic layer dried over anhydrous MgSO$_4$. Removal of the solvent under reduced pressure gave crude product, which was purified by column chromatography, using hexane followed by 5% ethyl acetate in hexane as eluent, to give 3-biphenylsulfonyl chloride as an oil (0.8 g, 49% yield).

B. N-(4-bromo-3-methyl-5-isoxazolyi)-3-biphenysulfonamide

N-(4-bromo-3-methyl-5-isoxazolyl)-3-biphenylsulfonamide was prepared in the same manner as described in Example 8b from 5-amino-4-bromo-3-methylisoxazole and 3-biphenylsulfonyl chloride in 22% yield. This was purified by HPLC (5% CH$_3$CN to 100% CH$_3$CN over 30 min.) to give a solid., m.p. 78–82° C.

EXAMPLE 13

N-(4-chloro-3-methyl-5-isoxazolyl)-3-biphenylsulfonamide

N-(4-chloro-3-methyl-5-isoxazolyl)-3-biphenylsulfonamide was prepared in the same manner as described in Example 12 from 5-amino-4-chloro-3-methylisoxazole and 3-biphenylsulfonyl chloride in 63% yield. This was purified by HPLC (5% CH$_3$CN to 100% CH$_3$CN over 30 min.) to give a solid, m.p. 84–86° C.

EXAMPLE 14

N-(3-methyl-5-isoxazolyi)-4-(4-methylphenyl)benzenesulfonamide (a) N-(3-methyl-5-isoxazolyi)-4-bromobenzenesulfonamide 4-brombenzenesulfonyl chloride (solid) was added, in five portions, to a solution of 3-methyl-5-aminoisoxazole (3.82 g, 40 mmol) in dry pyridine (30 ml). This was stirred at room temperature for 3 h and the pyridine was removed under reduced pressure. The residue was dissolved in THF (300 ml) and a 5% NaOH solution (100 ml) was added. Stirring continued for 1 h at room temperature. The THF was removed under reduced pressure and the resultant residue was neutralized to pH 2 using concentrated hydrochloric acid. This was extracted with ethyl acetate (3×200 ml) and the combined organic layer was dried over MgSO$_4$ and concentrated. The crude product was recrystallized using hexane/ethyl acetate giving N-(3-methyl-5-isoxazolyl)-4-bromobenzenesulfonamide (9.2 g, 72% yield).

(b) N-(3-methyl-5-isoxazolyi)-4-(4-methylphenyl)benzenesulfonamide

Nitrogen was bubbled through a biphasic mixture of ethanol (15 ml), toluene (15 ml) and 2M sodium carbonate solution (15 ml). N-(3-methyl-5-isoxazolyl)-4-bromobenzene sulfonamide (0.951 g, 3 mmol), 4-methylbenzeneboronic acid (0.56 g, 4 mmol) and tetrakistriphenylphosphine palladium (O) (300 mg) were added. The reaction mixture was kept at 80° C., under a N$_2$ atmosphere for 24 h, with stirring, and was then diluted with water (50 ml) and extracted with ether (50 ml) to remove neutral impurities and excess 4-methylbenzeneboronic acid. The aqueous phase was neutralized to pH 2 using concentrated hydrochloric acid and the resultant solid was filtered. This was dried under vacuum and recrystallized using hexanelethyl acetate giving N-(3-methyl-5-isoxazolyl)-4-(4-methylphenyl)benzenesulfonamide (1.0 g, 100% yield, 30 m.p. 194–198° C.).

EXAMPLE 15

N-(4-bromo-3-methyl-5-isoxazolyl)-4-(4-methylphenyl)benzenesulfonamide

N-bromosuccinimide (NBS) (0.178 g, 1 mmol), in one lot, was added to a stirred suspension of N-(3-methyl-5-isoxazolyl)-4-(4-methylphenyl)benzenesulfonamide (0.327g, 1 mmol, Example 14b) in chloroform (12 ml). The reaction mixture was stirred for 10 min then diluted with dichloromethane (50 ml). This was washed with water (2×50 ml). The organic layer was dried over MgSO$_4$ and concentrated. The crude product was recrystallized using hexane/ethyl acetate giving N-(4-bromo-3-methyl-5-isoxazolyl)-4-(4-methylphenyl)benzenesulfonamide (350 mg, 86% yield, m.p. 153–156° C.).

EXAMPLE 16

N-(4-chloro-3-methyl-5-isoxazolyi)-4-(4-methylphenyl)benzenesulfonamide

N-chlorosuccinimide (0.266 g, 2 mmol) was added, in one lot, to a stirred suspension of N-(3-methyl-5-isoxazolyl)-4-(4-methylphenyl)benzenesulfonamide (0.327g, 1 mmol, Example 14b) in chloroform (10 ml) and stirred at room temperature for 2 h The reaction mixture was diluted with dichloromethane (50 ml) and washed with water (2×50 ml). The organic layer was dried over MgSO$_4$ and concentrated. The crude product was purified by column chromatography using ethyl acetate as eluent to give N-(4-chloro-3-methyl-5-isoxazolyl)-4-(4-methylphenyl)benzenesulfonamide [210 mg, 58% yield, m.p. 260° C. (de coup)].

EXAMPLE 17

N-(3-methyl-5-isoxazolyi)-4-[(4-trifluoromethyl)phenyl]benzenesulfonamide

N-(3-methyl-5-isoxazolyl)-4-(4-trifluoromethylphenyl)benzenesulfonamide was prepared in the same manner as described in Example 14b, using N-(3-methyl-5-isoxazolyl)-4-bromobenzenesulfonamide and 4-trifluoromethylbenzeneboronic acid resulting in the final product in a 78% yield, m.p. 150–153° C. The product was recrystallized using an acetonirile and water mixture.

EXAMPLE 18

N-(4-bromo-3-methyl-5-isoxazolyl)-4-[(4-trifluoromethyl)phenyl]benzenesulfonamide N-(4-bromo-3-methyl-5-isoxazolyl)-4-[(4-trifluoromethyl)phenyl]benzenesulfonamide was prepared in the same manner as described in Example 15, using N-(3-methyl-5-isoxazolyl)-4-(4-trifluoromethylphenyl)benzenesulfonamide (Example 17) and NBS (reaction time 30 min at room temperature). The crude product was purified by column chromatography on silica gel using ethyl acetate as eluent resulting in the final product in 56% yield, m.p. 113–117° C.

EXAMPLE 19

N-(3-methyl-5-isoxazolyl)-4-(4-methoxyphenyl)benzenesulfonamide

N-(3-methyl-5-isoxazolyl)-4-(4-methoxyphenyl)benzenesulfonamide was prepared in the same manner as described in Example 14b, using N-(3-methyl-5-isoxazolyl)-4-bromobenzenesulfonamide (Example 14a) and 4-methoxybenzeneboronic acid resulting in an 82% yield of the final product, m.p. 194–196° C. The product was recrystallized using hexane/ethyl acetate.

EXAMPLE 20

N-(4-bromo-3-methyl-5-isoxazolyl)-4-(4-methoxyphenyl)benzenesulfonamide

N-(4-bromo-3-methyl-5-isoxazolyl)-4-(4-methoxyphenyl) benzenesulfonamide was prepared in the same manner as described in Example 15 using N-(3-methyl-5-isoxazolyl)-4-(4-methoxyphenyl)benzenesulfonamide (Example 19) and NBS (reaction time 30 min at room temperature). The crude product was purified by column chromatography on silica gel using ethyl acetate as eluent giving the final product in 78% yield, m.p. 208° C. (dec). The product was recrystallized using hexane/ethyl acetate.

EXAMPLE 21

N-(4-bromo-3-methyl-5-isoxazolyl)-4-(3-methoxyphenyl)benzenesulfonamide (a) N-(3-methyl-5-isoxazolyl)-4-(3-methoxyphenyl)benzenesulfonamide N-(3-methyl-5-isoxazolyl)-4-(3-methoxyphenyl) benzenesulfonamide was prepared in the same manner as described in Example 14b, using N-(3-methyl-5-isoxazolyl)-4-bromobenzenesulfonamide (Example 14a) and 3-methoxybenzeneboronic acid resulting in a 77% yield.

(b) N-(4-bromo-3-methyl-5-isoxazolyl)-4-(3-methoxyphenyl)benzenesulfonamide

N-(4-bromo-3-methyl-5-isoxazolyl)-4-(3-methoxyphenyl)benzenesulfonamide was prepared in the same manner as described in Example 15 using N-(3-methyl-5-isoxazolyl)-4-(3-methoxyphenyl)benzenesulfonamide and NBS (reaction time 30 min at room temperature). The crude product was purified by column chromatography on silica gel using ethyl acetate as eluent giving the final product, after recrystallization using hexane/ethyl acetate, in 75% yield, m.p. 140–144° C.

EXAMPLE 22

N-(4-bromo-3-methyl-5-isoxazolyl)-4-(2-methoxyphenyl)benzenesulfonamide (a) N-(3-methyl-5-isoxazolyl)-4-(2-methoxyphenyl)benzenesulfonamide N-(3-methyl-5-isoxazolyl)-4-(2-methoxyphenyl)benzenesulfonamide was prepared in the same manner as described in Example 14 using N-(3-methyl-5-isoxazolyl)-4-bromobenzenesulfonamide and 2-methoxybenzeneboronic acid resulting in an 81% yield of the final product.

(b) N-(4-bromo-3-methyl-5-isoxozolyl)-4-(2-methoxyphenyl)benzenesulfonamide

N-(4-bromo-3-methyl-5-isoxozolyl)-4-(2-methoxyphenyl) benzenesulfonamide was prepared in the same manner as described in Example 15, using N-(3-methyl-5-isoxazolyl)-4-(2-methoxyphenyl)benzenesulfonamide and NBS (reaction time 30 min at room temp.) The crude product was purified by column chromatography on silica gel using ethyl acetate as eluent to give the final product in 68% yield, m.p. 205–209° C.

EXAMPLE 23

N-(4-bromo-3-methyl-5-isoxazolyl)-4-(3,4-methylenedioxyphenyl)benzenesulfonamide (a) N-(3-methyl-5-isoxazolyl)-4-(3,4-methylenedioxyphenyl)benzenesulfonamide N-(3-methyl-5-isoxazolyl)-4-(3,4-methylenedioxyphenyl)benzenesulfonamide was prepared in the same manner as described in Example 14b, using N-(3-methyl-5-isoxazolyl)-4-bromobenzenesulfonamide and 3,4-methylenedioxyphenylboronic acid resulting in a 67% yield of final product.

(b) N-(4-bromo-3-methyl-5-isoxazolyl)-4-(3,4-methylenedioxyphenyl)benzenesulfonamide N-(4-bromo-3-methyl-5-isoxazolyl)-4-(3,4-methylenedioxyphenyl)benzenesulfonamide was prepared in the same manner as described in Example 15, using N-(3-methyl-5-isoxazolyl)-4-(3,4-methylenedioxyphenyl)benzenesulfonamide and NBS in THF as solvent resulting in a 35% yield. The crude product was purified by HPLC, m.p. 172–174° C.

EXAMPLE 24

N-(4-bromo-3-methyl-5-isoxazolyl)-4-(3-methylphenyl)benzenesulfonamide (a) N-(3-methyl-5-isoxazolyl)-4-(3-methylphenyl)benzenesulfonamide N-(3-methyl-5-isoxazolyl)-4-(3-methylphenyl)benzenesulfonamide was prepared in the same manner as described in Example 14b, using N-(3-methyl-5-isoxazolyl)-4-bromobenzenesulfonamide (Example 14a) and 3-methylbenzeneboronic acid resulting in an 82% yield.

(b) N-(4-bromo-3-methyl-5-isoxazolyl)-4-(3-methylphenyl)benzenesulfonamide

N-(4-bromo-3-methyl-5-isoxazolyl)-4-(3-methylphenyl)benzenesulfonamide was prepared in the same manner as described in Example 15, using N-(3-methyl-5-isoxazolyl)-4-(3-methylphenyl)benzenesulfonamide and NBS in THF as solvent (reaction time 30 min at room temperature). The crude product was purified by HPLC resulting in a 31% yield of the final product, m.p. 186–189° C.

EXAMPLE 25

N-(4-Bromo-3-methyl-5-isoxazolyl)benzenesulfonamide (a) 5-Amino-4-bromo-3-methylisoxazole 5-Amino-3-methylisoxazole (0.98 g, 10 mmol) was dissolved in chloroform (15 ml) and cooled to 0° C. N-Bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product which was purified by column chromatography using a 9:1 mixture of hexanes/ethyl acetate as eluent to give 5-amino-4-bromo-3-methylisoxazole (1.55 g, 87 % yield).

(b) N-(4-Bromo-3-methyl-5-isoxazolyl)benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol) in dry THF (1 ml) at 0° C. After stirring at 0–5° C. for 10 min., the reaction was warmed to room temperature for 10 min. to complete the reaction. The reaction mixture was re-cooled to 0° C. and benzenesulfonyl chloride (0.283 ml, 2.2 mmol) was added slowly. Stirring was continued for 20 min. at 0–5° C. Excess sodium hydride was decomposed by the addition of methanol (0.4 ml) followed by water (0.5 ml). The solvent was removed under reduced pressure. The residue was dissolved in water (20 ml), basified to pH 8–9 by the addition of sodium hydroxide and extracted with ethyl acetate (2×10 ml) to remove the neutral impurities. The aqueous layer was acidified with concentrate HCl (pH 2–3) and extracted with ethyl acetate (3×10 ml) The combined organic layer was dried over magnesium sulfate and concentrated under reduced pressure to give N-(4-bromo-3-methyl-5-isoxazolyl)benzenesulfonamide. The pure material was obtained by recrystallization using hexanes/ethyl acetate (0.59 g, 93% yield), m.p. 142–144° C.

EXAMPLE 26

N-(4-Bromo-5-tert-butyl-3-isoxazolyl)benzenesulfonamide (a) 3-Amino-4-bromo-5-tert-butylisoxazole This compound was prepared from 3-amino-5-tert-butylisoxazole and N-bromosuccinimide as described in Example 25a in 91% yield, $R_f$ 0.27 (3:1 hexanes/ethyl acetate).

(b) N-(4-Bromo-5-tert-butyl-3-isoxazolyl)benzenesulfonamide

3-Amino-4-bromo-5-tert-butylisoxazole (219 mg, 1.0 mmol) was dissolved in dry pyridine (1 ml). Benzenesulfonyl chloride (0.14 ml, 1.1 mmol) and 4-dimethylaminopyridine (5 mg) were added and the solution was stirred at 50° C. for 6 h. The reaction mixture was diluted with dichloromethane (75 ml), washed with 1N HCl (50 ml) and dried over anhydrous magnesium sulfate. The solvent was removed under reduced pressure to yield a crude product, which was purified by column chromatography (9:1 hexanes/ethyl acetate). A crystalline solid was obtained after recrystallization from ethyl acetate/hexanes, m.p. 139–141° C.

EXAMPLE 27
N-(3-Methyl-4-phenyl-5-isoxazolyl)benzenesulfonamide (a) N-(Benzenesulfonyl)-N-(3-methyl-4-phenyl-5-isoxazolyl)benzenesulfonamide 5-Amino-3-methyl-4-phenylisoxazole (0.174 g, 1.0 mmol) was dissolved in dry pyridine (2 ml). Benzenesulfonyl chloride (0.389 g, 2.2 mmol) was added with stirring at ambient temperature. N,N-Dimethylaminopyridine (5 mg) was added and stirring was continued at 50° C. for 4 h. The reaction mixture was diluted with dichloromethane (75 ml), washed with 1N HCl (2×50 ml) and the organic phase was dried over magnesium sulfate. The solvent was removed under reduced pressure to yield a crude product that was purified by column chromatography using 5:1, hexanes/ethyl acetate to give 0.390 g (85% yield) of N-benzenesulfonyl-N-(4-bromo-3-methyl-5-isoxazolyl)benzenesulfonamide.

(b) N-(3-Methyl-4-phenyl-5-isoxazolyl)benzenesulfonamide

N-Benzenesulfonyl-N-(3-methyl-4-phenyl-5-isoxazolyl)benzenesulfonamide (300 mg, 0.66 mmol) was dissolved in methanol. Potassium hydroxide (300 mg, 5.5 mmol) was added and the solution was warmed to 45° C. to dissolve the sodium hydroxide. Stirring was continued for 20 min. Methanol was removed under reduced pressure. The residue was dissolved in water, cooled to 0° C. and acidified to pH 3–4 with concentrated HCl. The solid precipitate was extracted with ethyl acetate, dried and evaporated in vacuo to give 210 mg (100% yield) of N-(3-methyl-4-phenyl-5-isoxazolyl)benzenesulfonamide, which was further purified by recrystallization from ethyl acetate/hexanes, m.p. 124–126° C.

EXAMPLE 28
N-(4-Bromo-3-phenyl—5-isoxazolyl)benzenesulfonamide

This compound was prepared from benzenesulfonyl chloride and 5-amino-4-bromo-3-phenylisoxazole according to the method in Example 25b in 36% yield. Recrystallization from methanol gave a yellow solid, m.p. 113–115° C.

EXAMPLE 29
N-(4-Bromo-3-tert-butyl-5-isoxazolyl)benzenesulfonamide (a) 5-Amino-4-bromo-3-tert-butylisoxazole 5-Amino-4-bromo-3-tert-butylisoxazole was prepared from 5-amino-3-tert-butylisoxazole and N-bromosuccinimide in 64% yield as described in Example 25a.

(b) N-Benzenesulfonyl-N-(4-Bromo-3-tert-butyl-5-isoxazolyl)benzenesulfonamide

5-Amino-4-bromo-3-tert-butylisoxazole (440 mg, 2.0 mmol) was dissolved in dry pyridine (2 ml). Benzenesulfonyl chloride (344 mg, 2.0 mmol) and 4-dimethylaminopyridine (5 mg) was added and the reaction was stirred at 50° C. for 16 h. The reaction mixture was diluted with ethyl acetate (20 ml), washed with 1N HCl (2×10 ml) and the organic phase was dried over magnesium sulfate. The solvent was removed under reduced pressure to yield a crude product, which was recrystallized from ethyl acetate/hexanes to give 300 mg (60% yield) of N-benzenesulfonyl-N-(4-bromo-3-tert-butyl-5-isoxazolyl)benzenesulfonamide.

(c) N-(4-Bromo-3-tert-butyl-5-isoxazolyl)benzenelsulfonamide

N-Benzenesulfonyl-N-(4-bromo-3-tert-butyl-5-isoxazolyl) benzenesulfonamide (80 mg, 0.16 mmol) was dissolved in methanol (2 ml). Sodium hydroxide (0.120 g, 3.0 mmol) in methanol was added and the solution was stirred at 45° C. for 20 min. Methanol was removed under reduced pressure. The residue was dissolved in water, cooled to 0° C. and acidified to pH 3–4 with concentrated hydrochloric acid and extracted with ethyl acetate. The extract was dried over anhydrous magnesium sulfate and concentrated in vacuo to give N-(4-bromo-3-tert-butyl-5-isoxazolyl)benzenesulfonamide in 94% yield. Further purification was achieved by recrystallization from methanol/water, giving an off white solid, m.p. 108–109° C.

EXAMPLE 30
4-tert-Butyl-N-(4-bromo-3-methyl-5-isoxazolyl)benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol) in dry THF (1 ml) at 0–5° C. After stirring at 0–5° C. for 10 min, the reaction was warmed to room temperature for 10 min. to complete the reaction. The reaction mixture was re-cooled to 0° C. and 4-tert-butylbenzenesulfonyl chloride (512 mg, 2.2 mmol) was added slowly. Stirring was continued for 20 min at 0–5° C. Excess sodium hydride was decomposed by the addition of methanol (0.4 ml) followed by water (0.5 ml). The mixture was acidified with hydrochloric acid and extracted with dichloromethane. The extract was dried over anhydrous magnesium sulfate and the solvent was removed under reduced pressure to give a crude product, which was purified by recrystallization from ethyl acetate/hexanes to give a white solid in 21% yield, m.p. 170° C. (dec.).

EXAMPLE 31
4-iso-Propyl-N-(4-bromo-3-methyl-5-isoxazolyl)benzenesulfonamide 4-iso-Pro pyl-N-(4-bromo-3-methyl-5-isoxazolyl) benzenesulfonamide was prepared in the same manner as described in Example 30 from 5-amino-4-bromo-3-methylisoxazole and 4-iso-propylbenzenesulfonyl chloride in 77% yield. Purification was achieved by recrystallization from ethyl acetate/hexanes to give a crystalline solid, m.p. 130–133° C.

EXAMPLE 32
4-Bromo-N-(4-bromo-3-methyl-5-isoxazolyl)benzenesulfonamide

4-Bromo-N-(4-bromo-3-methy l-5-isoxazolyl)benzenesulfonamide was prepared in the same manner as described in Example 30 from 5-amino-4-bromo-3-methylisoxazole and 4-bromobenzenesulfonyl chloride in 74% yield. Purification was achieved by recrystallization from ethyl acetate/hexanes to give a crystalline solid, m.p. 146–149° C.

EXAMPLE 33
4-Fluoro-N-(4-bromo-3-methyl-5-isoxazolyl)benzenesulfonamide

4-Fluoro-N-(4-bromo-3-methyl-5-isoxazolyl)benzenesulfonamide was prepared in the same manner as described in Example 30 from 5-amino-4-bromo-3-methylisoxazole and 4-fluorobenzenesulfonyl chloride in 71% yield. Purification was achieved by recrystallization from ethyl acetate/hexanes to give a crystalline solid, m.p. 142–144° C.

EXAMPLE 34
3-Nitro-N-(4-bromo-3-methyl-5-isoxazolyl)benzenesulfonamide

3-Nitro-N-(4-bromo-3-methyl-5-isoxazolyl)benzenesulfonamide was prepared in the same manner as described in Example 30 from 5-amino-4-bromo-3- methylisoxazole and 3-nitrobenzenesulfonyl chloride in 55% yield. Purification was achieved by recrystallization from ethyl acetate/hexanes to give a crystalline solid, m.p. 151–153° C.

EXAMPLE 35

N-(4-Bromo-5-methyl-3-isoxazolyl)benzenesulfonamide (a) 3-Amino-4-bromo-5-methylisoxazole 3-Amino-5-methylisoxazole (1.96 g, 20 mmol) was dissolved in chloroform (10 ml) and cooled to 0° C. N-Bromosuccinimide (3.56 g, 20 mmol) was added in small portions over a period of 10 min. The stirring was continued for another 15 minutes at 0° C. The reaction mixture was diluted with chloroform (100 ml), washed with water (2×50 ml) and the organic layer was dried over magnesium sulfate. Removal of the solvent under reduced pressure gave the crude product, which was purified by column chromatography using 9:1, hexanes/ethyl acetate as eluent, to give 3-amino-4-bromo-5-methylisoxazole (1.40 g, 40% yield).

(b) N-(4-bromo-5-methyl-3-isoxazolyl) benzenesulfonamide and N-(benzenesulfonyl)N-(4-bromo-5-methyl-3-isoxazolyl)benzenesulfonamide 3-Amino-4-bromo-5-methylisoxazole (5.31 g, 30 mmol) was dissolved in dry pyridine (30 ml). Benzenesulfonyl chloride (5.24 ml, 42 mmol) was added dropwise with stirring at ambient temperature. N,N-(Dimethyl) aminopyridine (100 mg) was added and stirring was continued at 50° C. for 25 h. The reaction mixture was diluted with dichloromethane (200 ml), washed with 1N HCl (6×100 ml) and the organic phase was dried over magnesium sulfate. The solvent was removed under reduced pressure to yield a crude product which was purified by column chromatography using 9:1, hexanes/ethyl acetate as eluent to give N-(benzenesulfonyl)-N-(4-bromo-5-methyl-3-isoxazolyl)benzenesulfonamide (7 g, 51% yield, $R_f$=0.27 using 3:1, hexanes/ethyl acetate as eluent) as a solid.

Further elution with ethyl acetate gave N-(4-bromo-5-methyl-3-isoxazolyl)benzenesulfonamide (2 g, 21% yield, $R_f$=0.08 with 3:1 hexanes/ethyl acetate as eluent), m.p. 128–130° C.

(c) N-(4-bromo-5-methyl-3-isoxazolyl) benzenesulfonamide

Sodium hydroxide (1.3 g, 30.6 mmol) was added to a solution of N-(benzenesulfonyl)-N-(4-bromo-5-methyl-3-isoxazolyl)benzene-sulfonamide (7 g, 15.3 mmol, prepared as described in (a)) in methanol (100 ml). The resulting solution was stirred at 25° C. for 30 h. Excess methanol was removed under reduced pressure. The residue was dissolved in water (50 ml) and acidified (pH 3–4) by the addition of concentrated HCl with cooling. The mixture was extracted with dichloromethane (2×100 ml) and the combined organic layer was dried over anhydrous magnesium sulfate. Removal of the solvent gave N-(4-bromo-5-methyl-3-isoxazolyl)benzenesulfonamide which was purified by crystallization from ethyl acetate/hexanes (4.5 g, 92% yield). The compound is identical to the one isolated in step (b).

EXAMPLE 36

N-(4-Bromo-5-methyl-3-isoxazolyl)-1-naphthalenesulfonamide

N-(4-Bromo-5-methyl-3-isoxazolyl)-1-naphthalenesulfonamide was prepared from 3-amino-4-bromo-5-methylisoxazole and 1-naphthalenesulfonyl chloride as described in Example 26 in 51% yield. Recrystallization from ethyl acetate/hexanes gave a crystalline solid, m.p. 167–170° C.

EXAMPLE 37

N-(4-Chloro-3-methyl-5-isoxazolyl)benzenesuolfonamide (a) 5-Amino-4-chloro-3-methylisoxazole Using the method in Example 25a, 5-amino-4-chloro-3-methylisoxazole was prepared in 90% yield from 5-amino-3-methylisoxazole and N-chlorosuccinimide.

(b) N-(4-Chloro-3-methyl-5-isoxazolyl) benzenesuolfonamide

N-(4-Chloro-3-methyl-5-isoxazolyl) benzenesuolfonamide was prepared according to the method in Example 25b from 5-amino-4-chloro-3-methylisoxazole and benzenesulfonyl chloride in 84% yield. The crude product was purified by recrystallization using hexanes/ ethyl acetate, m.p. 140–143° C.

EXAMPLE 38

N-(4-Chloro-5-methyl-3-isoxazolyl)benzenesulfonamide (a) 3-Amino-4-chloro-5-methylisoxazole This compound was prepared from 3-amino-5-methylisoxazole and N-chlorosuccinimide as described in Example 25a except the reaction was changed to 35° C and the reaction time was extended to 12 h. The yield was 62%, $R_f$ 0.17 (3:1 hexanes/ethyl acetate).

(b) N-(4-Chloro-5-methyl-3-isoxazolyl) benzenesulfonamide

N-(4-chloro-5-methyl-3-isoxazolyl)benzenesulfonamide was prepared from 3-amino-4-chloro-5-methylisoxazole and benzenesulfonyl chloride as described in Example 26b in 40% yield. The crude product was purified by column chromatography with 10–100% ethyl acetate/hexanes as eluent. A crystalline solid was obtained after recrystallization from ethyl acetate/hexanes, m.p. 139–141° C. 3-Amino-4-chloro-5-methylisoxazole (25% recovery) and N-(benzenesulfonyl)-N-(4-chloro-5-methyl-3-isoxazolyl) benzenesulfonamide (7% yield) were also obtained as less polar products.

EXAMPLE 39

4-Iodo-N-(4-bromo-3-methyl-5-isoxazolyl) benzenesulfonamide

4-Iodo-N-(4-bromo-3-methyl-5-isoxazolyl) benzenesulfonamide was prepared from 5-amino-4-bromo-3-methylisoxazole and 4-iodobenzenesulfonyl chloride according to the procedures described in Example 25b. The crude product was purified by recrystallization from ethyl acetate/hexanes to give a yellow powder, m.p. 166–173° C., yield 65%.

EXAMPLE 40

4-Chloro-N-(4-bromo-3-methyl-5-isoxazolyl) benzenesulfonamide

4-Chloro-N-(4-bromo-3-methyl-5-isoxazolyl) benzene-sulfonamide was prepared from 5-amino-4-bromo-3-methylisoxazole and 4-chlorobenzenesulfonyl chloride according to the procedures described in Example 25b. The crude product was purified by recrystallization from ethyl acetate/hexanes to give a yellow powder, m.p. 145–150° C., yield 93%.

EXAMPLE 41

N-(4-Bromo-3-ethyl-5-isoxazolyl)benzenesulfonamide (a) 5-Amino-4-bromo-3-ethylisoxazole 5-Amino-4-bromo-3-ethylisoxazole was prepared from 5-amino-3-ethylisoxazole and N-bromosuccinimide as described in Example 25a.

(b) N-(4-Bromo-3-ethyl-5-isoxazolyl) benzenesulfonamide

N-(4-Bromo-3-ethyl-5-isoxazolyl) benzenesulfonamide was prepared from 5-amino-4-bromo-3-ethylisoxazole and benzenesulfonyl chloride according to the procedures described in Example 25b. The crude product was purified by recrystallization from ethyl acetate/hexanes to give off-white crystals, m.p. 90–93° C., yield 70%.

EXAMPLE 42
N-(4-Bromo-3-methyl-5-isoxazolyl)-4-toluenesulfonamide

N-(4-Bromo-3-methyl-5-isoxazolyl)-4-toluenesulfonamide was prepared from 5-amino-4-bromo-3-methylisoxazole and 4-toluenesulfonyl chloride according to the procedures described in Example 25b. The crude product was purified by recrystallization from ethyl acetate/hexanes to give off-white crystals, m.p. 169–172° C., yield 69%.

EXAMPLE 43
2,5-Dimethyl-N-(4-bromo-3-methyl-5-isoxazolyl)benzenesulfonamide 2,5-Dimethyl-N-(4-bromo-3-methyl-5-isoxazolyl)benzenesulfonamide was prepared from 5-amino-4-bromo-3-methylisoxazole and 2,5-di-methylbenzenesulfonyl chloride according to the procedures described in Example 25b. The crude product was purified by recrystallization from ethyl acetate/hexanes to give off-white crystals, m.p. 102–104° C., yield 81%.

EXAMPLE 44
N-(4-Bromo-3-methyl-5-isoxazolyl)-2-toluenesulfonamide

N-(4-Bromo-3-methyl-5-isoxazolyl)-2-toluenesulfonamide was prepared from 5-amino-4-bromo-3-methylisoxazole and 2-toluenesulfonyl chloride according to the procedures described in Example 25b. The crude product was purified by recrystallization from ethyl acetate/hexanes to give white crystalline solid, m.p. 93–96° C., yield 88%.

EXAMPLE 45
2-Fluoro-N-(4-bromo-3-methyl-5-isoxazolyl)benzenesulfonamide

2-Fluoro-N-(4-bromo-3-methyl-5-isoxazolyl)benzenesulfonamide was prepared from 5-amino-4-bromo-3-methylisoxazole and 2-fluorobenzenesulfonyl chloride according to the procedures described in Example 25b. The crude product was purified by recrystallization from ethyl acetate/hexanes to give a white solid, m.p. 87–89° C., yield 44%.

EXAMPLE 46
3-Fluoro-N-(4-bromo-3-methyl-5-isoxazolyl)benzenesulfonamide

3-Fluoro-N-(4-bromo-3-methyl-5-isoxazolyl)benzenesulfonamide was prepared from 5-amino-4-bromo-3-methylisoxazole and 3-fluorobenzenesulfonyl chloride according to the procedures described in Example 25b. The crude product was purified by recrystallization from ethyl acetate/hexanes to give a light yellow solid, m.p. 125–128° C., yield 88%.

EXAMPLE 47
2,5-Dimethyl-N-(4-chloro-3-methyl-5-isoxazolyl)benzenesulfonamide 2,5-Dimethyl-N-(4-chloro-3-methyl-5-isoxazolyl)benzenesulfonamide was prepared from 5-amino-4-chloro-3-methylisoxazole and 2,5-dimethylbenzenesulfonyl chloride according to the procedures described in Example 25b. The crude product was purified by recrystallization from ethyl acetate/hexanes to give a light yellow solid, m.p. 92–93° C., yield 82%.

EXAMPLE 48
4-Acetamido-N-(4-bromo-3-methyl-5-isoxazolyl)benzenesulfonamide

4-Acetamido-N-(4-bromo-3-methyl-5-isoxazolyl)benzenesulfonamide was prepared from 5-amino-4-bromo-3-methylisoxazole and 4-acetylsulfinilyl chloride according to the procedures described in Example 30. The crude product was purified by recrystallization from ethyl acetate/hexanes to give a crystalline solid, m.p. 208–210° C., yield 56%.

EXAMPLE 49
4-Nitro-N-(4-bromo-3-methyl-5-isoxazolyl)benzenesulfonamide

4-Nitro-N-(4-bromo-3-methyl-5-isoxazolyl)benzenesulfonamide was prepared from 5-amino-4-bromo-3-methylisoxazole and 4-nitrobenzenesulfonyl chloride according to the procedures described in Example 30. The crude product was purified by recrystallization from ethyl acetate/hexanes to give a crystalline solid, m.p. 146–149° C., yield 34%.

EXAMPLE 50
4-Butoxy-N-(4-bromo-3-methyl-5-isoxazolyl)benzenesulfonamide

4-Butoxy-N-(4-bromo-3-methyl-5-isoxazolyl) benzenesulfonamide was prepared from 5-amino-4-bromo-3-methylisoxazole and 4-butoxybenzenesulfonyl chloride according to the procedures described in Example 30. The crude product was purified by recrystallization from ethyl acetate/hexanes to give a crystalline solid, m.p. 98–100° C., yield 33%.

EXAMPLE 51
3-Chloro-2-methyl-N-(4-Bromo-3-methyl-5-isoxazolyl)benzenesulfonamide 3-Chloro-2-methyl-N-(4-Bromo-3-methyl-5-isoxazolyl)benzenesulfonamide was prepared from 5-amino-4-bromo-3-methylisoxazole and 3-chloro-2-methylbenzenesulfonyl chloride according to the procedures described in Example 30. The crude product was purified by recrystallization from ethyl acetate/hexanes to give a crystalline solid, m.p. 185–187° C., yield 34%.

EXAMPLE 52
2,4,6-Trimeth.1-N-(4-bromo-3-methyl-5-isoxazolyi)benzenesulfonamide 2,4,6-Trimethyl-N-(4-bromo-3-methyl-5-isoxazolyl)benzenesulfonamide was prepared from 5-amino-4-bromo-3-methylisoxazole and 2,4,6-trimethylbenzenesulfonyl chloride according to the procedures described in Example 25b. The crude product was purified by recrystallization from ethyl acetate/hexanes to give a pink solid, m.p. 92–95° C., yield 64%

EXAMPLE 53
N-(4-bromo-3-methyl-5-isoxazolyl)-3-toluenesulfonamide

N-(4-bromo-3-methyl-5-isoxazolyl)-3-toluenesulfonamide was prepared from 5-amino-4-bromo-3-methylisoxazole and 3-toluenesulfonyl chloride according to the procedures described in Example 30. The crude product was purified by recrystallization from ethyl acetate/hexanes to give a crystalline solid, m.p. 138–140° C., yield 63%.

EXAMPLE 54

3-Chloro-2,5-dimethyl-N-(4-bromo-3-methyl-5-isoxazolyl)benzenesulfonamide

3-Chloro-2,5-dimethyl-N-(4-bromo-3-methyl-5-isoxazolyl)benzenesulfonamide was prepared from 5-amino-4-bromo-3-methylisoxazole and 3-chloro-2,5-dimethylbenzenesulfonyl chloride according to the procedures described in Example 30. The crude product was purified by recrystallization from ethyl acetate/hexanes to give a crystalline solid, m.p. 148–150° C., yield 71%.

EXAMPLE 55

2,5-Difluoro-N-(4-bromo-3-methyl-5-isoxazolyl)benzenesulfonamide 2,5-Difluoro-N-(4-bromo-3-methyl-5-isoxazolyl)benzenesulfonamide was prepared from 5-amino-4-bromo-3-methylisoxazole and 4-chlorobenzenesulfonyl chloride according to the procedures described in Example 30. The crude product was purified by recrystallization from ethyl acetate/hexanes to give a crystalline solid, m.p. 123–125° C., yield 62%.

EXAMPLE 56

2,3,4-Trichloro-N-(4-bromo-3-methyl-5-isoxazolyl)benzenesulfonamide 2,3,4-Trichloro-N-(4-bromo-3-methyl-5-isoxazolyl) benzenesulfonamide was prepared from 5-amino-4-bromo-3-methylisoxazole and 2,3,4-trichlorobenzenesulfonyl chloride according to the procedures described in Example 30. The crude product was purified by recrystallization from ethyl acetate/hexanes to give a crystalline solid, m.p.110–113° C., yield 66%.

EXAMPLE 57

2,3-Dichloro-N-(4-bromo-3-methyl-5-isoxazolyl)benzenesulfonamide 2,3-Dichloro-N-(4-bromo-3-methyl-5-isoxazolyl)benzenesulfonamide was prepared from 5-amino-4-bromo-3-methylisoxazole and 2,3-dichlorobenzenesulfonyl chloride according to the procedures described in Example 30. The crude product was purified by recrystallization from ethyl acetate/hexanes to give a crystalline solid, m.p. 166–169° C., yield 75%.

EXAMPLE 58

2,5-Dichloro-N-(4-bromo-3-methyl-5-isoxazolyl)benzenesulfonamide 2,5-Dichloro-N-(4-bromo-3-methyl-5-isoxazolyl)benzenesulfonamide was prepared from 5-amino-4-bromo-3-methylisoxazole and 2,5-dichlorobenzenesulfonyl chloride according to the procedures described in Example 25b. The crude product was purified by recrystallization from ethyl acetate/hexanes to give a yellow powder, m.p. 148–150° C., yield 53%.

EXAMPLE 59

5-Bromo-2-methoxy-N-(4-bromo-3-methyl-5-isoxazolyl)benzenesulfonamide

5-Bromo-2-methoxy-N-(4-bromo-3-methyl-5-isoxazolyl)benzenesulfonamide was prepared from 5-amino-4-bromo-3-methylisoxazole and 5-bromo-2-methoxybenzenesulfonyl chloride according to the procedures described in Example 30. The crude product was purified by recrystallization from ethyl acetate/hexanes to give a crystalline solid, m.p. 192–195° C., yield 61%.

EXAMPLE 60

2-Bromo-N-(4-bromo-3-methyl-5-isoxazolyl)benzenesulfonamide

2-Bromo-N-(4-bromo-3-methyl-5-isoxazolyl)benzenesulfonamide was prepared from 5-amino-4-bromo-3-methylisoxazole and 2-bromobenzenesulfonyl chloride according to the procedures described in Example 30. The crude product was purified by recrystallization from ethyl acetate/hexanes to give a crystalline solid, m.p. 84–86° C., yield 31%.

EXAMPLE 61

2-Cyano-N-(4-bromo-3-methyl-5-isoxazolyl)benzenesulfonamide

2-Cyano-N-(4-bromo-3-methyl-5-isoxazolyl) benzenesulfonamide was prepared from 5-amino-4-bromo-3-methylisoxazole and 4-chlorobenzenesulfonyl chloride according to the procedures described in Example 30. The crude product was purified by recrystallization from ethyl acetate/hexanes to give a crystalline solid, m.p. 152–155° C., yield 70%.

EXAMPLE 62

2,4,5-Trichloro-N-(4-bromo-3-methyl-5-isoxazolyl)benzenesulfonamide 2,4,5-Trichloro-N-(4-bromo-3-methyl-5-isoxazolyl)benzenesulfonamide was prepared from 5-amino-4-bromo-3-methylisoxazole and 2,4,5-trichlorobenzenesulfonyl chloride according to the procedures described in Example 30. The crude product was purified by recrystallization from ethyl acetate/hexanes to give a crystalline solid, m.p. 179–182° C., yield 67%.

EXAMPLE 63

3,4-Dichloro-N-(4-bromo-3-methyl-5-isoxazolyl)benzenesulfonamide 3,4-Dichloro-N-(4-bromo-3-methyl-5-isoxazolyl)benzenesulfonamide was prepared from 5-amino-4-bromo-3-methylisoxazole and 3,4-dichlorobenzenesulfonyl chloride according to the procedures described in Example 30. The crude product was purified by recrystallization from ethyl acetate/hexanes to give a crystalline solid, m.p. 144–146° C., yield 60%.

EXAMPLE 64

3,4-Dimethoxy-N-(4-bromo-3-methyl-5-isoxazolyl)benzenesulfonamide 3,4-Dimethoxy-N-(4-bromo-3-methyl-5-isoxazolyl)benzenesulfonamide was prepared from 5-amino-4-bromo-3-methylisoxazole and 3,4-dimethoxybenzenesulfonyl chloride according to the procedures described in Example 30. The crude product was purified by recrystallization from ethyl acetate/hexanes to give a crystalline solid, m.p. 136–138° C., yield 64%.

EXAMPLE 65

2,4-Dichloro-N-(4-bromo-3-methyl-5-isoxazolyl)benzenesulfonamide 2,4-Dichloro-N-(4-bromo-3-methyl-5-isoxazolyl) benzenesulfonamide was prepared from 5-amino-4-bromo-3-methylisoxazole and 2,4-dichlorobenzenesulfonyl chloride according to the procedures described in Example 30. The crude product was purified by recrystallization from ethyl acetate/hexanes to give a crystalline solid, m.p. 138–141° C., yield 46%.

EXAMPLE 66

N-(4-Iodo-5-methyl-3-isoxazolyl)benzenesulfonamide
(a) 3-amino-4-Iodo-5-methylisoxazole 3-Amino-4-iodo-5-methylisoxazole was prepared from 3-amino-5-methylisoxazole and N-iodosuccinimide as described in Example 50a in 46% yield, m.p. 115–117° C.

(b) N-(4-Iodo-5-methyl-3-isoxazolyl) benzenesulfonamide

N-(4-Iodo-5-methyl-3-isoxazolyl) benzenesulfonamide was prepared from 3-amino-4-iodo-5-methylisoxazole and benzenesulfonyl chloride according to the procedures described in Example 25b. The crude product was purified by recrystallization from ethyl acetate/hexanes to give a brown powder m.p. 138–141° C., yield 46%.

EXAMPLE 67
4-Nitro-N-(4-bromo-5-methyl-3-isoxazolyl) benzenesulfonamide 4-Nitro-N-(4-bromo-5-methyl-3-isoxazolyl)benzenesulfonamide was prepared from 5-amino-4-bromo-3-methylisoxazole and 4-nitrobenzenesulfonyl chloride according to the procedures described in Example 25b. The crude product was purified by recrystallization from ethyl acetate/hexanes to give a light tan solid, m.p. 161–163° C., yield 55%.

EXAMPLE 68
3-Nitro-N-(4-bromo-5-methyl-3-isoxazolyl) benzenesulfonamide

3-Nitro-N-(4-bromo-5-methyl-3-isoxazolyl) benzenesulfonamide was prepared from 5-amino-4-bromo-3-methylisoxazole and 3-nitrobenzenesulfonyl chloride according to the procedures described in Example 25b. The crude product was purified by recrystallization from ethyl acetate/hexanes, resulting in an off white powder, m.p. 137–139° C., yield 72%.

EXAMPLE 69
4-Trifluoromethyl-N-(4-bromo-3-methyl-5-isoxazolyl) benzenesulfonamide 4-Trifluoromethyl-N-(4-bromo-3-methyl-5-isoxazolyl) benzenesulfonamide was prepared from 5-amino-4-bromo-3-methylisoxazole and 4-trifluoromethylbenzenesulfonyl chloride according to the procedures described in Example 30. The crude product was purified by recrystallization from ethyl acetate/hexanes to give a crystalline solid, m.p. 155–158° C., yield 72%.

EXAMPLE 70
3-Trifluoromethyl-N-(4-bromo-3-methyl-5-isoxazolyl) benzenesulfonamide 3-Trifluoromethyl-N-(4-bromo-3-methyl-5-isoxazolyl) benzenesulfonamide was prepared from 5-amino-4-bromo-3-methylisoxazole and 3-trifluoromethylbenzenesulfonyl chloride according to the procedures described in Example 30. The crude product was purified by recrystallization from ethyl acetate/hexanes to give a crystalline solid, m.p. 113–115° C., yield 83%.

EXAMPLE 71
Assays for Identifying Compounds that Exhibit Endothelin Antagonistic and/or Agonist Activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin Binding Inhibition—Binding Test #1: Inhibition of Binding to $ET_A$ Receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5mM $MgCl_2$, 0.5% Bacitracin) to a concentration of 8 µg/50 µl. $^{125}$I-endothelin-1 (3,000 cpm, 50 mL) was added to 50 µL of either: (A) endothelin-1 (for non specific binding) to give a final concentration 80 nM); (B) binding buffer (for total binding); or (C) a test compound (final concentration 1 nM to 100 µM). The membrane suspension (50 µL), containing up to 8 µg of membrane protein, was added to each of (A), (B), or (C). Mixtures were shaken, and incubated at 4° C. for 16–18 hours, and then centrifuged at 4° C. for 25 min at 2,500×g. Alternatively, the incubation was conducted at 24° C. When incubated at 24° C., the $IC_{50}$ concentrations are 2- to 10-fold higher than when the incubation is conducted at 4° C. This, must be kept in mind when comparing $IC_{50}$ concentrations among compounds provided herein.

The supernatant, containing unbound radioactivity, was decanted and the pellet counted on a Genesys multiwell gamma counter. The degree of inhibition of binding (D) was calculated according to the following equation:

$$\%D = 100 - \frac{(C)-(A)}{(B)-(A)} \times 100$$

Each test was generally performed in triplicate.

B. Endothelin Binding Inhibition—Binding Test #2: Inhibition of Binding to $ET_B$ Receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C57,800×g for 15 min, the pellet was resuspended in 5 ml of buffer A (5mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 μg/50 μl of binding buffer.

C. Test for Activity Against Endothelin-Induced Contraction of Isolated Rat Thoracic Aortic Rings The effectiveness of the test compound as an antagonist or agonist of the biological tissue response of endothelin also is assessed by measuring the effect on endothelin induced contraction of isolated rat thoracic aortic rings (see, em, Borges et al. (1989) *Eur. J. Pharmacol.* 165:223–230) or by measuring the ability to contract the tissue when added alone.

Compounds to be tested are prepared as 100 μM stocks. If necessary to effect dissolution, the compounds are first dissolved in a minimum amount of DMSO and diluted with 150 mM NaCl. Because DMSC can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'—Henseleit solution saturated with a gas mixture of 95% $O_2$ and 5% $CO_2$ (118 mM NaCl, 4,7 mM KCl, 1.2 mM $MgSO_4$, 1.2 mM $KH_2PO_4$, 25 mM $NaHCO_3$, 2.5 mM $CaCl_2$, 10 mM D-glucose).

There is a correlation between activity as an antagonist of endothelin-induced thoracic aortic ring contraction and activity as an inhibitor of binding of endothelin to endothelin receptors. The $pA_2$ is a linear function of the log of the $IC_{50}$.

D. Assay for Identifying Compounds That Have Agonist and/or Antagonistic Activity Against $ET_B$ Receptors 1. Stimulation of Prostacyclin Release Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-16-keto $PGF_{1\alpha}$ release possess antagonist activity.

2. Inhibition of Sarafotoxin 6c Induced Contraction

Sarafotoxin 6c is a specific $ET_B$ antagonist that contracts rat fundal stomach strips. The effectiveness of tests compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs'—Henseleit solution containing 10 $\mu$M cyclo(D-Asp-Pro-D-Val-Leu-D-Trp) (BQ-123; see, U.S. Pat. No. 5,114,918 to Ishikawa et al.), 5 $\mu$M indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preincubated for 15 min with a test compound prior to addition of cumulative doses of sarafotoxin 6c. The effects of the test compounds on the concentration-response curve for sarafotoxin 6c are examined.

E. Deoxycorticosterone Acetate (DOCA)-Salt Hypertensive Rat Model for Assessing in vivo Activity of Selected Compounds Selected compounds disclosed herein have been tested for activity in the deoxycorticosterone acetate (DOCA)-salt hypertensive rat model. To perform these tests, silastic MDX4-4210 elastomer implants containing 47 mg (DOCA) were prepared according to the method of Ornmsbee et al. ((1973) the *J. Pharm. Sci.* 62:255–257). Briefly, DOCA is incorporated into silicon rubber implants for sustained release. To prepare the implants the DOCA is incorporated into unpolymerized silicone rubber, catalyst is added and the mixture is cast in a hemicylindrical shape.

Sprague Dawley rats (7–8 weeks old) were unilaterally nephrectomized under ketamine anesthesia and a DOCA-implant was placed on the left lateral dorsal abdomen of the animal. The rats were allowed to recover for three weeks. During recovery they were permitted free access to normal rat chow and 0.9% NaCl drinking solution in place of drinking water. The rats develop hypertension within 3 weeks.

All animals were used in the tests between 21 and 30 days post surgery. The mean arterial blood pressure in these animals ranged from 165–200 mm Hg.

On the day of experimentation, catheters were inserted under brevital anesthesia into the right femoral artery for measurement of blood pressure, and into the right femoral vein for administration of a selected compound. The animals were placed in a restrainer and allowed to recover for a minimum of 60 min or until a steady mean arterial blood pressure was recorded. At that time, the selected compound or control vehicle was administered either intravenously, as a 60 minute infusion, or orally by oral gavage. Blood pressure was recorded continuously for a further 10 h.

F. Results

The $IC_{50}$ for each of the compounds of the preceding Examples for $ET_A$ and $ET_B$ receptors has been measured. Almost all of the compounds have an $IC_{50}$ of less than 10 $\mu$M for either or both of the $ET_A$ and $ET_B$ receptors. Many of the compounds have an $IC_{50}$ less than about 10 $\mu$M, others have an $IC_{50}$ less than about 1 $\mu$M and some of the compounds have an $IC_{50}$ less than about 0.1 $\mu$M. A number of the compounds have an $IC_{50}$ for $ET_A$ receptors that is substantially less (10 to 100-fold or more) than for $ET_B$ receptors, and, thus are selective for $ET_A$ receptors. Others of the compounds, particularly the compounds in which $Ar^2$ is 4-biphenyl are $ET_B$ selective.

Since modifications will be apparent to those of skill in this art, it is intended that this invention be limited only by the scope of the appended claims.

We claim:

1. A method of altering nitric oxide levels, comprising administering an effective amount of an endothelin antagonist, whereby nitric oxide levels are altered.

2. The method of claim 1, wherein the endothelin antagonist is a compound or pro-drugs of the compounds or pharmaceutically acceptable salts or acids of the compounds of formula:

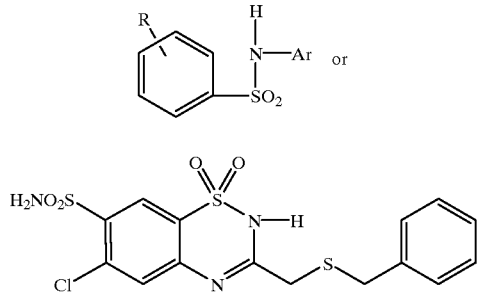

wherein:
R is $NH_2$, halogen,

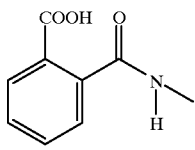

or is absent;
Ar is selected from:

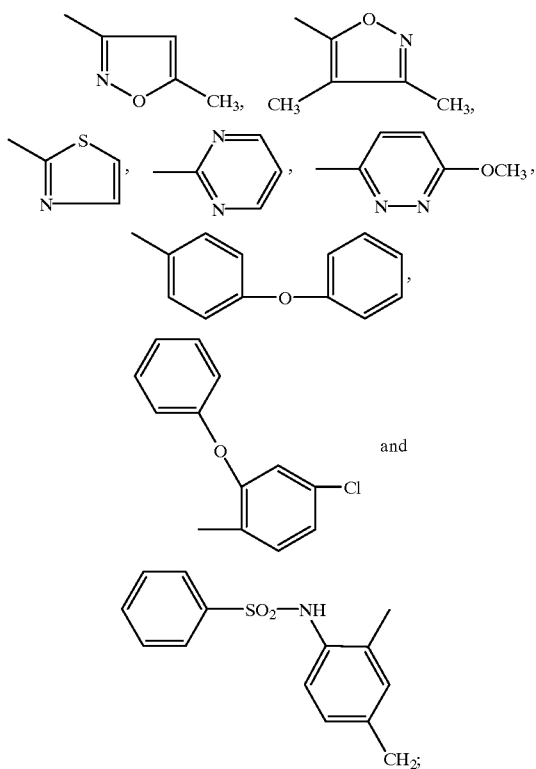

whereby nitric oxide levels are altered.

3. The method of claim 2, wherein the compound is selected from the group consisting of compounds in which R is in the para position.

4. The method of claim 1, wherein the endothelin antagonist is a compound of formula:

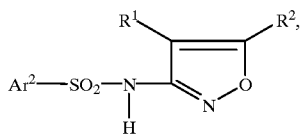

wherein:
(a) $R^1$ and $R^2$ are either (i), (ii) or (iii) as follows:
  (i) $R^1$ and $R^2$ are each independently selected from the group consisting of H, $NH_2$, $NO_2$, halide, pseudohalide, alkyl, alkenyl, alkynyl, aryl, arylalkyl, heteroaryl, alkoxy, alkylamino, alkylthio, alkylalkoxy, alkylhalide, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons; or,
  (ii) $R^1$ and $R^2$ together form $-(CH_2)_n$, where n is 3 to 6; or,
  (iii) $R^1$ and $R^2$ together form 1,3-butadienyl; and
(b) $Ar^2$ is alkyl or is a group selected from:

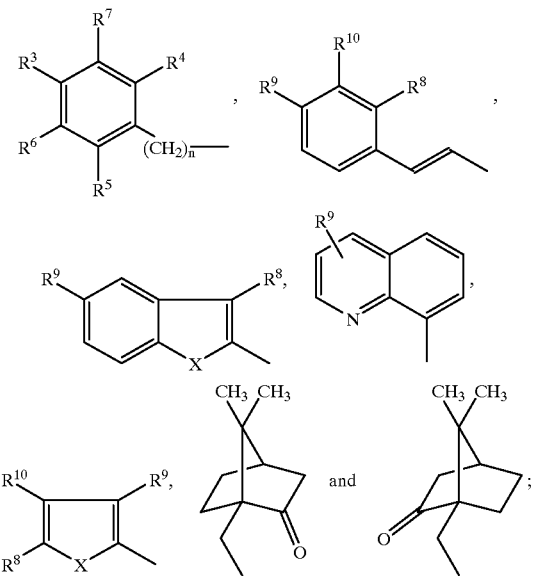

wherein:
(i) $R^3$, $R^4$, $R^5$, $R^6$, and $R^7$ are each independently selected from the group consisting of H, NHOH, $NH_2$, $NO_2$, $N_3$, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl, alkynyl portions are straight or branched chains of from about 1 up to about 10 carbons, and the aryl portions contain from 4 to 14 carbons; $R^8$, $R^9$ and $R^{10}$ are each independently selected from the group consisting of H, $NH_2$, $NO_2$ and halide; X is O, S or $NR^{11}$ in which $R^{11}$ is selected from H, alkyl, alkylcarbonyl or formyl; and n is from 0 up to about 6; or, alternatively, (ii) $R^4$ and $R^7$ together are substituted or unsubstituted 1,3-butadienyl, 1-aza-1,3-butadienyl or 2-aza-1,3-butadienyl groups; and n, X, $R^3$, $R^5$, $R^6$, $R^8$, $R^9$, $R^{10}$ and $R^{11}$ are as defined in (i) above; or alternatively, (iii) $R^7$ and $R^3$ together are substituted or unsubstituted 1,3-butadienyl, 1-aza-1,3-butadienyl or 2-aza-1,3-butadienyl groups; and n, X, $R^4$, $R^5$, $R^6$, $R^8$, $R^9$, $R^{10}$ and $R^{11}$ are as defined in (i) above; whereby nitric oxide levels are altered.

5. The method of claim 4, wherein:

(a) $R^1$ and $R^2$ are selected independently from the group consisting of lower alkyl, lower alkenyl, lower alkynyl, lower haloalkyl, halide, pseudohalide and H;

(b) X is $NR^{11}$, S or O, n is 0 or 1; $R^{11}$ is H, $CH_3$ or formyl; and $R^3$, $R^4$, $R^5$, $R^6$, $R^7$, $R^8$, $R^9$ and $R^{10}$ are either (i), (ii) or (ii) as follows:

(i) $R^4$ and $R^7$ are each independently selected from the group consisting of H, lower alkyl, $NH_2$, $NO_2$, halide, pseudohalide; $R^3$ is selected from the group consisting of H, NHOH, $NH_2$, $NO_2$, $N_3$, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from 1 up to 6 carbons and the aryl portions contain from 4 to 10 or 12 carbons; $R^5$, $R^6$, $R^{10}$ are H; $R^{11}$ is H or $CH_3$; $R^8$ and $R^9$ are each selected independently from among H, $NO_2$, $NH_2$ and halide; or (ii) $R^4$ and $R^7$ together form 1,3-butadienyl, 4-chloro-1,3-butadienyl, or 1-aza-1,3-butadienyl; $R^3$ is selected from the group consisting of H, NHOH, $NH_2$, $NO_2$, $N_3$, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 5 or 6 carbons and the aryl portions contain from 1 up to about 6 carbons; $R^5$, $R^6$, $R^{10}$ are H; $R^{11}$ is H or $CH_3$; $R^8$ and $R^9$ are each selected independently from among H, $NO_2$, $NH_2$ and halide; or (iii) $R^7$ and $R^3$ together form 1,3-butadienyl, 3-chloro-1,3-butadienyl or 1-aza-1,3-butadienyl; $R^4$ is selected from the group consisting of H, lower alkyl, $NH_2$, $NO_2$, halide, pseudohalide; $R^5$, $R^6$, $R^{10}$ are H; $R^{11}$ is H or $CH_3$; $R^8$ and $R^9$ are each selected independently from among H, $NO_2$, $NH_2$ and halide.

6. The method of claim 4, wherein:

(a) $R^1$ and $R^2$ are independently selected from the group consisting of H, $CH_3$, $C_2H_5$, $H_2C{=}CH$, $CH{\equiv}C$, Ph—O, Ph—$CH_2$, 4—$CH_3$—$C_6H_4O$ halide, $CF_3$, $C_2F_5$, n-$C_3H_7$ and iso-$C_3H_7$; and (b) $Ar^2$ is $CH_3$ or is selected from

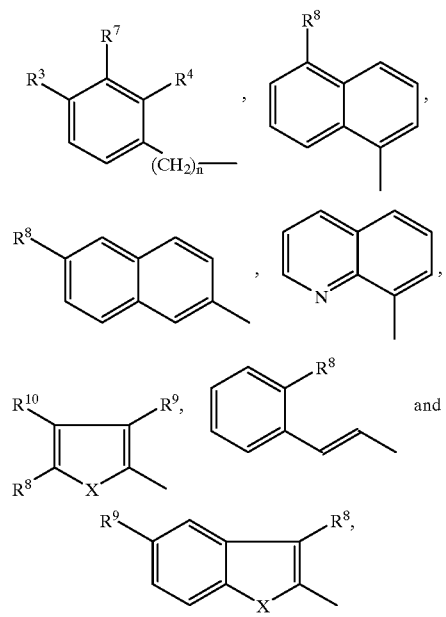

in which:

X is S or O; n is 0 or 1; $R^{11}$ is H; and $R^3$, $R^4$, $R^7$ and $R^8$ are either (i), (ii) or (iii) as follows:

(i) $R^8$ is H, $NO_2$, $NH_2$ or halide; $R^4$ and $R^7$ are each independently selected from the group consisting of H, halide, $NH_2$, $CF_3$, Ph and $CH_3$; and $R^3$ is selected from the group consisting of H, NHOH, $NH_2$, $C_2H_5NH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n-$C_4H_9O$, $CH_2{=}CH$, Ph—$CH{=}CH$, $CH{\equiv}C$, Ph—$CH{\equiv}C$, Ph, 3-(ethyoxycarbonylmethyl)ureido, and 3-cyclohexylureido; or (ii) $R^4$ and $R^7$ together form 1,3-butadienyl, 4-chloro-1,3-butadienyl, or 1-aza-1,3-butadienyl; $R^3$ is selected from the group consisting of H, NHOH, $NH_2$, $EtNH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n-$C_4H_9O$, $CH_2{=}CH$, Ph—$CH{=}CH$, $CH{\equiv}C$, Ph—$CH{\equiv}C$, Ph, 3-(ethyoxycarbonylmethyl)ureido, and 3-cyclohexylureido; and $R^8$ is H, $NO_2$, $NH_2$ or halide; or (iii) $R^7$ and $R^3$ together form 1,3-butadienyl, 3-chloro-1,3-butadienyl or 1-aza-1,3-butadienyl; $R^4$ is selected from the group consisting of H, halide, $NH_2$, $CF_3$, Ph and $CH_3$; and $R^8$ is H, $NO_2$, $NH_2$ or halide.

7. The method of claim 6, wherein:

$Ar^2$ is a substituted or unsubstituted phenyl group or unsubstituted or unsubstituted naphthyl group or a substituted or unsubstituted quinolinyl group; $R^1$ is Br, Cl, H, $CH_3$, $C_2H_5$, $CF_3$; $R^2$ is H, $CH_3$, $C_2H_5$, or $CF_3$; and $R^3$, $R^4$, $R^7$, $R^8$, $R^9$, $R^{10}$ and $R^{11}$ are either (i), (ii), (iii) or (iv) as follows:

(i) $R^7$, $R^8$, $R^9$, $R^{10}$ and $R^{11}$ are H; n is 0 and $R^3$ is H, $NH_2$, $CH_3$ $CF_3$, halide, $C_2H_5NH$ or Ph, $R^4$ is H, $CF_3$, $NH_2$; and $R^7$ is H or $CF_3$; or (ii) $R^3$, $R^8$, $R^9$, $R^{10}$ and $R^{11}$, are H; n is 0; and $R^4$ and $R^7$ together form 1, 3-butadienyl or 4-chloro-1,3-butadienyl; or (iii) $R^4$, $R^8$, $R^9$, $R^{10}$ and $R^{11}$, are H; n is 0 and $R^7$ and $R^3$ together form 1,3-butadienyl, 1-aza-1,3-butadienyl; or (iv) $R^7$, $R^8$, $R^9$, $R^{10}$ and $R^{11}$ are H; n is 1 and $R^3$ is H, $NH_2$ and halide; $R^4$ is H, $CF_3$, $NH_2$; and $R^7$ is H or $CF_3$.

8. The method of claim 1, wherein the endothelin antagonist is a compound of formula:

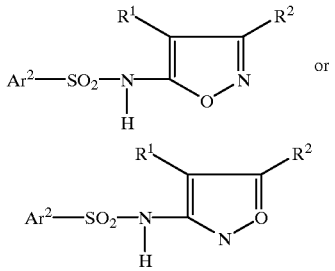

or a pharmaceutically acceptable salt thereof, wherein:
$R^1$ and $R^2$ are either (i), (ii) or (iii) as follows:
(i) $R^1$ and $R^2$ are each independently selected from the group consisting of H, $NH_2$, $NO_2$, halide, pseudohalide, alkyl, alkenyl, alkynyl, aryl, arylalkyl, heteroaryl, alkoxy, alkylamino, alkylthio, alkyloxy, aminoalkyl, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido and substituted or unsubstituted ureido, in which the alkyl, alkenyl and alkynyl portions contain from 1 up to about 14 carbon atoms and are either straight or branched chains, and the aryl portions contain from about 4 to about 16 carbons; or,
(ii) $R^1$ and $R^2$ together form —$(CH_2)_n$—, where n is 3 to 6; or,
(iii) $R^1$ and $R^2$ together form 1,3-butadienyl;

$Ar^2$ is benzene or a substituted benzene and has the formula:

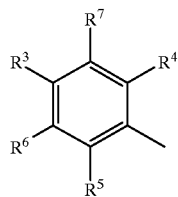

in which $R^3$, $R^4$, $R^5$, $R^6$, and $R^7$ are either (i) or (ii) as follows:
(i) $R^3$, $R^4$, $R^5$, $R^6$, and $R^7$ are each selected independently from the group consisting of H, NHOH, $NH_2$, $NO_2$, pseudohalide, halide, alkenyl, alkynyl, aryl, heteroaryl, alkoxy, alkylamino, dialkylamino, aminoalkyl, alkylthio, alkylalkoxy, alkylsulfinyl, alkylsulfonyl, aryloxy, arylalkyl, arylamino, arylthio, arylsulfinyl, arylsulfonyl, haloalkyl, haloalkoxy, haloaryl, alkoxycarbonyl, alkylcarbonyl, arylcarbonyl, carboxyl, hydroxyl, formyl, substituted or unsubstituted amido, substituted or unsubstituted ureido, where the alkyl, alkenyl, alkynyl portions are straight or branched chains, which are cyclic or acyclic, of from about 1 up to 10 carbons, and the aryl portions contain from 3 up to about 10 carbons;
(ii) $R^3$, $R^5$, and $R^7$ are H; and $R^4$ and $R^6$ are each independently selected from the group consisting of alkyl, alkoxy, halide, amino alkyl and dialkylaminoalkyl in which the alkyl and alkoxy groups contain from 1 to 10 carbons, and are straight or branched chains, whereby nitric oxide levels are altered.

9. The method of claim 8, wherein:
$R^1$ and $R^2$ are selected independently from the group consisting of alkyl, lower alkenyl, lower alkynyl, lower haloalkyl, halide, pseudohalide and H; and $R^3$, $R^4$, $R^5$, $R^6$, and $R^7$ are either (i) or (ii) as follows:
(i) $R^4$, $R^5$, $R^6$ and $R^7$ are each independently selected from the group consisting of H, lower alkyl, $NH_2$, $NO_2$, lower alkylamino, lower dialkylamino, halide, lower haloalkyl, lower alkoxy, lower haloalkoxy, amino (lower)alkyl, and pseudohalide; $R^3$ is selected from H, NHOH, $NH_2$, $NO_2$, $N_3$, lower alkylamino, lower dialkyl amino, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido and substituted or unsubstituted ureido, and the alkyl, alkenyl, alkynyl portions are straight or branched chains of from 1 to 6 carbons and the aryl portions contain from 3 to 14 carbons; or
(ii) $R^3$, $R^5$, and $R^7$ are H; and $R^4$ and $R^6$ are each independently selected from the group consisting of alkyl, amino alkyl and dialkylaminoalkyl in which the alkyl groups contain from 1 to 6 carbons, and are straight or branched chains.

10. The method of claim 8, wherein:
$R^1$ and $R^2$ are independently selected from the group consisting of H, $CH_3$, $C_2H_5$, $H_2C=CH$, $CH\equiv C$, Ph—O, Ph—$CH_2$, 4—$CH_3$—$C_6H_4O$, halide, $CF_3$, $C_2F_5$, n-$C_3H_7$, iso-$C_3H_7$, cyclo-$C_3H_7$, n$C_4H_9$, iso-$C_4H_9$, tert-$C_4H_9$, n$C_6H_{13}$, n$C_{13}H_{27}$ and n$C_9H_{19}$;
and $R^3$, $R^4$, $R^5$, $R^6$, and $R^7$ are either (i) or (ii) as follows:
(i) $R^4$, $R^5$, $R^6$ and $R^7$ are each independently selected from the group consisting of H, halide, $NH_2$, $CF_3$, Ph,$CH_3$ $CH_3O$, $NO_2$; and $R^3$ is selected from the group consisting of H, NHOH, $NH_2$, $C_2H_5NH_2$, $(CH_3)_2NH$, Ph—$CH_2NH$, $NO_2$, F, Cl, Br, I, CN, $CH_3$, $(CH_3)_2CH$, $(CH_3)_3C$, $C_5H_{11}$, $CH_3O$, n-$C_4H_9O$, $CH_2=CH$, Ph—CH=CH, CH$\equiv$C, Ph—CH$\equiv$C, Ph, 3-(ethyoxycarbonylmethyl)ureido, and 3-cyclohexylureido; or
(ii) $R^3$, $R^5$, and $R^7$ are H; and $R^4$ and $R^6$ are alkyl groups alkyl groups that contain from 1 to 3 carbons, and are straight or branched chains.

11. The method of claim 8, wherein:
$R^1$ is Br, Cl, H, $CH_3$, $C_2H_5$ or $CF_3$;
$R^2$ is H, $CH_3$, $C_2H_5$ or $CF_3$;
and $R^3$, $R^4$, $R^5$, $R^6$, and $R^7$ are either (i) or (ii) as follows:
(i) $R^3$ is H. $NH_2$, $CH_3$ $CF_3$, halide, $CH_3$, $(CH_3)_3C$, $(CH_3)_2CH$ or $C_2H_5NH$;$R^4$, $R^5$ and $R^6$ are independently selected from H, $CH_3$, $C_2H_5$, $(CH_3)_2CH$, $CF_3$, $CH_3O$, F, Br, Cl and $NH_2$; and $R^7$ is H, $CH_3$, $CH_2CH_5$, $(CH_3)CH$, $CH_3O$, F, Br, Cl, or $CF_3$; or
(ii) $R^3$, $R^5$, and $R^7$ are H; and $R^4$ and $R^6$ are ethyl.

12. The method of claim 1, wherein the endothelin antagonist is a compound of formula:

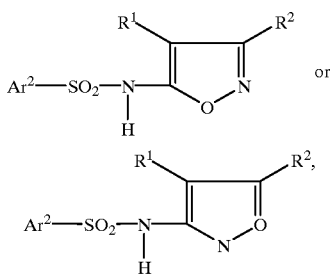

or a pharmaceutically acceptable salt thereof,
wherein:
R$^1$ is halide;
R$^2$ is selected from the group consisting of H, NH$_2$, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons; and
Ar$^2$ is substituted or unsubstituted alkyl or alkenyl in which the substituents are selected from the group consisting of H, NH$_2$, halide, lower alkyl, aryl, alkoxy (lower)alkyl in which the alkyl portions contain from 1 up to 14 carbon atoms and are either straight or branched chains, the lower alkyl portions contain from 1 to 6 carbons, and the aryl portions contain from about 3 to about 16 carbons, or Ar$^2$ is a group selected from the group consisting of:

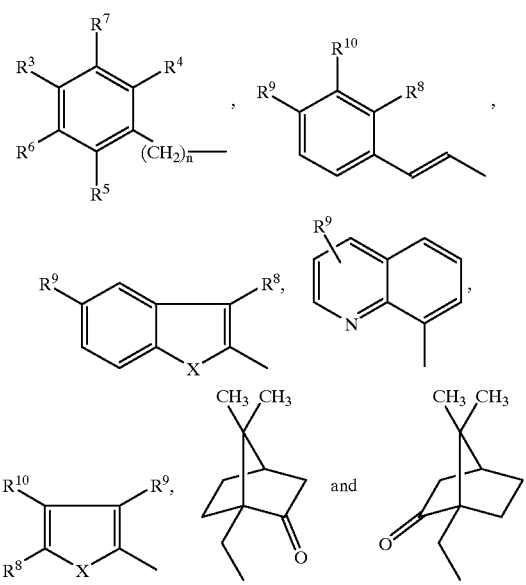

in which R$^3$, R$^4$, R$^5$, R$^6$, R$^7$, R$^8$, R$^9$, R$^{10}$ and R$^{11}$ are either (i), (ii), (iii) or (iv):
(i) R$^3$, R$^4$, R$^5$, R$^6$, and R$^7$ are each selected independently from the group consisting of H, NHOH, NH$_2$, NO$_2$, N$_3$, aminoalkyl, alkylamino, dialkylamino, dialkylaminoalkyl, carboxyl, carbonyl, hydroxyl, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which the alkyl, alkenyl, alkynyl portions are straight or branched chains of from 1 up to 10 carbons and the aryl portions contain from 3 to 10 carbons; R$^8$, R$^9$ and R$^{10}$ are each independently selected from H, NH$_2$, NO$_2$ and halide; X is O, S or NR$^{11}$ in which R$^{11}$ is H, alkyl, alkylcarbonyl or formyl; and n is from 0 up to about 6; or, alternatively,
(ii) R$^4$ and R$^7$ together are substituted or unsubstituted 1, 3-butadienyl, 4-dimethylamino-1,3 butadiene, 1-chloro-1,3-butadiene, 4-dimethylamino-1,3-butadienyl, 1-aza-1,3-butadienyl or 2-aza-1,3-butadienyl groups; and n, X, R$^3$, R$^5$, R$^6$, R$^8$, R$^9$, R$^{10}$ and R$^{11}$ are as defined in (i) above; or alternatively,
(iii) R$^7$ and R$^3$ together are substituted or unsubstituted 1,3-butadienyl, 4-dimethylamino-1,3butadiene, 1-chloro-1,3-butadiene, 4-dimethylamino-1,3-butadienyl, 1-aza-1,3-butadienyl or 2-aza-1,3-butadienyl groups; and n, X, R$^4$, R$^5$, R$^6$, R$^8$, R$^9$, R$^{10}$ and R$^{11}$ are as defined in (i); or alternatively
(iv) R$^3$, R$^5$, and R$^7$ are H; and R$^4$ and R$^6$ are each independently selected from the group consisting of alkyl, alkoxy, halide, amino alkyl and dialkylaminoalkyl in which the alkyl and alkoxy groups contain from 1 to 10 carbons, and are straight or branched chains; and R$^8$, R$^9$, R$^{10}$ and R$^{11}$ are as defined in (i), whereby nitric oxide levels are altered.

13. The method of claim 12, wherein R$^1$ is Br or Cl; R$^2$ is selected from the group consisting of alkyl, lower alkenyl, lower alkynyl, lower haloalkyl, halide, pseudohalide and H; n is 0 or 1; and R$^3$, R$^4$, R$^5$, R$^6$, R$^7$, R$^8$, R$^9$, R$^{10}$ and R$^{11}$ are either (i), (ii), (iii), or (iv):
(i) R$^4$ and R$^7$ are each independently selected from the group consisting of H, lower alkyl, NH$_2$, NO$_2$, halide, pseudohalide; and R$^3$ is selected from the group consisting of H, NHOH, NH$_2$, NO$_2$, N$_3$, halide, pseudohalide, alkyl, alkenyl, alkynyl, aryl, heteroaryl, alkoxy, alkylamino, dialkylamino, dialkylaminoalkyl, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted and unsubstituted amido, substituted or unsubstituted ureido, in which the alkyl, alkenyl, alkynyl portions are straight or branched chains of from 1 up to 6 carbons and the aryl portions contain from 3 to 6 carbons; R$^5$, R$^6$, R$^{10}$ are H; R$^{11}$ is H or CH$_3$; R$^8$ and R$^9$ are each selected independently from the group consisting of H, NO$_2$, NH$_2$ and halide; or
(ii) R$^4$ and R$^7$ together form 1, 3-butadienyl, 4-chloro-1, 3-butadienyl, 4-dimethylamino-1,3-butadienyl, or 1-aza-1,3-butadienyl; and R$^3$, R$^5$, R$^6$, R$^8$, R$^9$, R$^{10}$ and R$^{11}$ are defined as in (i) of this embodiment; or
(iii) R$^7$ and R$^3$ together form 1,3-butadienyl, 3-chloro-1, 3-butadienyl, 4-dimethylamino-1,3-butadienyl, or 1-aza-1,3-butadienyl; and R$^4$, R$^5$, R$^6$, R$^8$, R$^9$, R$^{10}$ and R$^{11}$ are as defined in (i);
(iv) R$^3$, R$^5$, and R$^7$ are H; and R$^4$ and R$^6$ are each independently selected alkyl, amino alkyl and dialkylaminoalkyl in which the alkyl and alkoxy groups contain from 1 to 6 carbons, and are straight or branched chains; and $R^8, R^9, R^{10}$ and $R^{11}$ are as defined in (i).

14. The method of claim 12, wherein $R^2$ is selected from the group consisting of H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n-$C_3H_7$, iso-$C_3H_7$, n$C_{13}H_{27}$ and n$C_9H_{19}$; $R^1$ is Cl or Br; X is NH, O or S; n is 0 or 1; and $R^3, R^4, R^5, R^6, R^7, R^8, R^9, R^{10}$ and $R^{11}$ are either (i), (ii), (iii) or (iv):
  (i) $R^8$ and $R^9$ are H, $NO_2$, $NH_2$ or halide; $R^5, R^6$ and $R^{11}$ are H; $R^4$ and $R^7$ are each independently selected from the group consisting of H, halide, $NH_2$, $CF_3$, Ph, $CH_3$; and $R^3$ is selected from the group consisting of H, NHOH, $NH_2$, $EtNH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n-$C_4H_9O$, $CH_2=CH$, Ph—$CH=CH$, $CH\equiv C$, dimethylaminomethyl, Ph—$CH\equiv C$, Ph, 3-(ethyoxycarbonylmethyl)ureido, and 3-cyclohexylureido; or
  (ii) $R^4$ and $R^7$ together form 1,3-butadienyl, 4-chloro-1,3-butadienyl, 4-diamino-1,3-butadienyl or 1-aza-1,3-butadienyl; and $R^3, R^5, R^6, R^8, R^9, R^{10}$ and $R^{11}$ are defined as in (i); or
  (iii) $R^7$ and $R^3$ together form 1,3-butadienyl, 3-chloro-1,3-butadienyl, 4-diamino-1,3-butadienyl or 1-aza-1,3-butadienyl; and $R^4, R^5, R^6, R^8, R^9, R^{10}$ and $R^{11}$ are as defined in (i); or
  (iv) $R^3, R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8, R^9, R^{10}$ and $R^{11}$ are as defined in (i).

15. The method of claim 12, wherein $R^1$ is Br or Cl; $R^2$ is H, $CH_3$, $C_2H_5$, $H_2C=CH$, $CH\equiv C$, Ph—O, Ph—$CH_2$, 4-$CH_3$-$C_6H_4O$, halide, $CF_3$, $C_2F_5$, n-$C_3H_7$, iso-$C_3H_7$, n$Cl_3H_{27}$ and n$C_9H_{19}$; and $Ar^2$ is a substituted or unsubstituted phenyl group; and $R^3, R^4, R^5, R^6$ and $R^7$ are either (i), (ii) or (iii):
  (i) $R^5, R^6$ and $R^7$ are H; n is 0; $R^3$ is H, $NH_2$, $CH_3$ $CF_3$, halide, $C_2H_5NH$ or Ph; $R^4$ is H, $CF_3$, $NH_2$; $R^7$ is H or $CF_3$; and $R^5$ and $R^6$ are H; or
  (ii) n is 1; $R^3$ is H, $NH_2$ or halide; $R^4$ is H, $CH_3$, Br, Cl, F, $CF_3$, $NH_2$, $R^7$ is H, $CH_3$, Br, Cl, F, $NH_2$ or $CF_3$; and $R^5$ and $R^6$ are H; or
  (iii) $R^3, R^5$, and $R^7$ are H; and $R^4$ and $R^6$ are each independently selected from the group consisting of alkyl groups that contain from 1 to 3 carbons.

16. The method of claim 12, wherein $R^1$ is Br or Cl; $R^2$ is H, $CH_3$, $C_2H_5$, $C_2F_5$ or $CF_3$; and $Ar^2$ is a substituted or unsubstituted naphthyl group or thianaphthyl group in which and $R^3, R^4, R^5, R^6$ and $R^7$ are either (i) or (ii):
  (i) $R^3, R^5$ and $R^6$ are H; n is 0 and $R^4$ and $R^7$ together form 1,3-butadienyl, 4-dimethylamino-1,3 butadiene, 1-chloro-1,3-butadiene, or 4-chloro-1,3-butadienyl; or
  (ii) $R^4, R^5, R^6, R^8, R^9, R^{10}$ and $R^{11}$ are H; n is 0; and $R^7$ and $R^3$ together form 1,3-butadienyl, 4-dimethylamino-1,3 butadiene, 1-chloro-1, 3-butadiene, 1-aza-1,3-butadienyl.

17. The method of claim 12, wherein $R^1$ is Br or Cl; $R^2$ is selected from the group consisting of H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n-$C_3H_7$, iso-$C_3H_7$ and $C_4H_9$; and $Ar^2$ is selected from the group consisting of substituted or unsubstituted thiophenes, furans, a pyrroles, indoles, benzofurans, quinolines, isoquinolines, styrenes and thianaphthalenes in which $R^1$ is Cl or Br; X is NH, O or S; n is 0 or 1; in (i) $R^8$ and $R^9$ are H, $NO_2$, $NH_2$ or halide; $R^5, R^6$ and $R^{11}$ are independently selected from the group consisting of H, $CF_3$, halide, Cl and $NH_2$; $R^4$ and $R^7$ are each independently selected from the group consisting of H, halide, $NH_2$, $CF_3$, Ph, $CH_3$; and $R^3$ is selected from the group consisting of H, NHOH, $NH_2$, $EtNH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n-$C_4H_9O$, $CH_2=CH$, Ph—$CH=CH$, $CH\equiv C$, Ph—$CH\equiv C$, Ph, 3-(ethyoxycarbonylmethyl)ureido, and 3-cyclohexylureido; and in (iv) $R^3, R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8, R^9, R^{10}$ and $R^{11}$ are as defined in (i).

18. The method of claim 17, wherein $R^2$ is H, $CH_3$, $C_2H_5$, or $CF_3$; in (i) $R^3$ is H, $NH_2$, $CH_3$ $CF_3$, halide or $C_2H_5NH$; $R^4, R^5$ and $R^6$ are H; $R^7$ is selected from the group consisting of H, $CH_3$, $CH_2CH_5$, $(CH_3)CH$, F or $CF_3$, and $R^8, R^9$ and $R^{10}$ are independently selected from the group consisting of H, $NO_2$, $NH_2$ or halide; and $R^{11}$ is H; and in (iv) $R^3, R^5$, and $R^7$ are H; and $R^4$ and $R^6$ are each independently selected from the group consisting of alkyl groups that contain from 1 to 3 carbons, and are straight or branched chains; and $R^8, R^9, R^{10}$ and $R^{11}$ are as defined in (i).

19. The method of claim 1, wherein the endothelin antagonist is a compound of the formula:

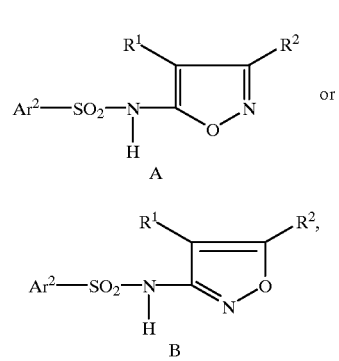

or a pharmaceutically acceptable salt thereof, wherein:

$R^1$ is halide;

$R^2$ is selected from the group consisting of H, $NH_2$, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons; and $Ar^2$ is alkenyl, biphenyl, quinolyl, styryl, isoquinolyl, indolyl or thianaphthyl, whereby nitric oxide levels are altered.

20. The method of claim 19, wherein $Ar^2$ is biphenyl.

21. The method of claim 1, wherein the endothelin antagonist is a compound of formula:

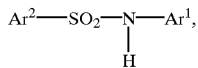

wherein:

Ar$^1$ is a substituted or unsubstituted group, containing from 1 to 30 carbon atoms, selected from the group consisting of alkyl, alkenyl and alkynyl groups, which may be straight or branched chains or include cyclic portions, aryl groups, heterocyclic rings and fused bicyclic or tricyclic rings; and Ar$^2$ is a substituted or unsubstituted group selected from thiophenyl, furyl and pyrrolyl, whereby nitric oxide levels are altered.

22. The method of claim 21, wherein Ar$^1$ is alkyl or is selected from the group consisting of the following groups:

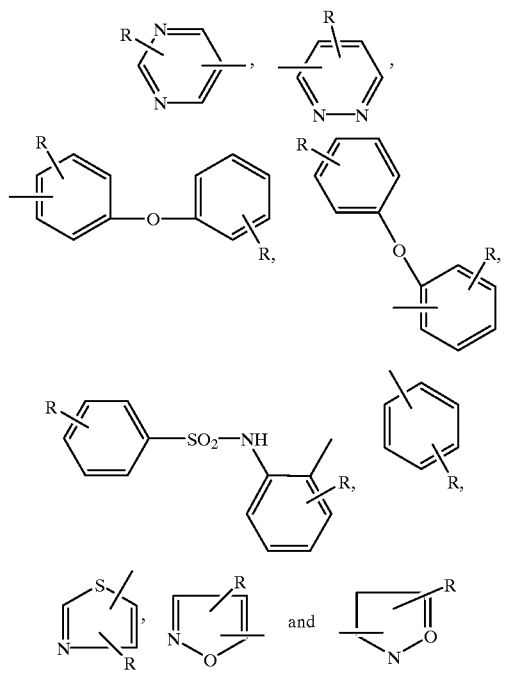

that are unsubstituted or substituted with one or more substituents R, which are each independently selected from the group consisting of H, NH$_2$, halide, pseudohalide, alkyl alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted, the alkyl portions are straight or branched chains of from about 1 up to about 10–12 carbons, and the aryl portions are substituted or unsubstituted and contain from 3 to about 14 carbon atoms.

23. The method of claim 21, wherein Ar$^1$ is an isoxazolyl group.

24. The method of claim 23, wherein the compound has the formula:

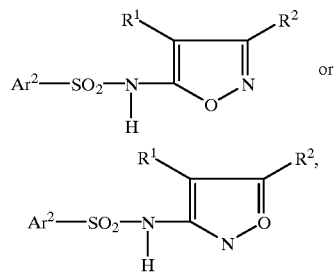

wherein R$^1$ and R$^2$ are selected from (i), (ii) or (iii):

(i) R$^1$ and R$^2$ are each independently selected from the group consisting of H, NH$_2$, NO$_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or, (ii) R$^1$ and R$^2$ together form —(CH$_2$)$_n$, where n is 3 to 6; or, (iii) R$^1$ and R$^2$ together form 1,3-butadienyl.

25. The method of claim 24, wherein Ar$^2$ is thiophenyl.
26. The method of claim 24, wherein Ar$^2$ is furyl.
27. The method of claim 24, wherein Ar$^2$ is pyrrolyl.
28. The method of claim 24, wherein the compound has the formulae:

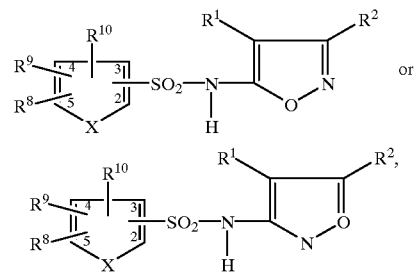

wherein:

X is O, S, NH or NR$^{11}$ in which R$^{11}$, which is hydrogen or contains up to about 30 carbon atoms, is selected from the group consisting of hydrogen, alkyl, alkenyl, alkynyl, aryl, alkylaryl, heterocycle, aralkyl, aralkoxy, cycloalkyl, cycloalkenyl, cycloalkynyl, C(O)R$^{15}$ and S(O)$_n$R$^{15}$ in which n is 0–2; and R$^{15}$, which is selected independently from R$^{11}$ is selected from the group consisting of hydrogen, alkyl, alkenyl, alkynyl, aryl, alkylaryl, heterocycle, aralkyl, aralkoxy, cycloalkyl, cycloalkenyl, cycloalkynyl;

and R$^8$, R$^9$ and R$^{10}$ are selected from (i) or (ii):

(i) R$^8$, R$^9$ and R$^{10}$, which each contain hydrogen or up to about 50 carbon atoms, are each independently selected from the group consisting of hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, C(O)R$^{18}$, CO$_2$R$^{18}$, SH, S(O)$_n$R$^{18}$ in which n is 0–2, HNOH, $NR^{18}R^{19}$, $NO_2$, $N_3$, $OR^{18}$, $R^{19}NCOR^{18}$ and $CONR^{19}R^{18}$, in which $R^{19}$ is selected from the group consisting of hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$ and $S(O)_nR^{20}$ in which n is 0–2; and $R^{18}$ and $R^{20}$ are each independently selected from the group consisting of hydrogen, alkyl, alkenyl, alkynyl, aryl, alkylaryl, heterocycle, alkoxy, aryloxy, alkoxy, aralkyl, aralkoxy, cycloalkyl, cycloalkenyl or cycloalkynyl; or (ii) any two of $R^8$, $R^9$ and $R^{10}$ form an aromatic or heteroaromatic ring or an alicyclic or heterocyclic ring, which is saturated or unsaturated, containing from about 3 to about 16 members, and the other of $R^8$, $R^9$ and $R^{10}$ is selected as in (i); where $R^8$, $R^9$, and $R^{10}$ may be further substituted with one or more substituents selected from Z, which is selected from the group consisting of hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$;

$R^{16}$ is selected from the group consisting of hydrogen, alkyl, alkenyl, alkynyl, aryl, alkylaryl, heterocycle, aralkyl, aralkoxy, cycloalkyl, cycloalkenyl and cycloalkynyl;

$R^{12}$ is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is selected from the group consisting of hydrogen, alkyl, alkenyl, alkynyl, aryl, alkylaryl, heterocycle, aralkyl, aralkoxy, cycloalkyl, cycloalkenyl or cycloalkynyl.

29. The method of claim 28, wherein X is S.
30. The method of claim 28, wherein X is O.
31. The method of claim 28, wherein X is N.
32. The method of claim 28, wherein at least two of $R^8$, $R^9$ and $R^{10}$ hydrogen, halogen or lower alkyl, and the other is $C(O)R^{18}$, $CO_2R^{18}$, $NR^{18}R^{19}$, $R^{19}NCOR^{18}$, or $CONR^{19}R^{18}$; where $R^{18}$ is phenyl and $R^{19}$ is H or lower alkyl.

33. The method of claim 32, wherein $R^1$ is Br or Cl or lower alkyl and $R^2$ is lower alkyl, lower haloalkyl, or hydrogen.

34. The method of claim 21, wherein the compound is selected from the group consisting of N-(4-bromo-3-methyl-5-isoxazolyl)-2-(N-phenylcarboxamide)thiophene-3-sulfonamide; N-(3,4-dimethyl-5-isoxazolyl)-2-(N-phenylcarboxamide)thiophene-3-sulfonamide, N-(4-bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide, N-(4-bromo-3-methyl-5-isoxazolyl)thiophene-2-sulfonamide, N-(4-bromo-3-methyl-5-isoxazolyl)-2-[N-(4-biphenyl)carboxamide]thiophene-3-sulfonamide, N-(4-bromo-3-methyl-5-isoxazolyl)-2-[N-(4-ethylphenyl)carboxamide]thiophene-3-sulfonamide, N-(4-bromo-3-methyl-5-isoxazolyl)-2-[N-(benzylcarboxamide]thiophene-3-sulfonamide, N-(4-bromo-3-methyl-5-isoxazolyl)-2-[N-(2-methoxyphenyl)carboxamide]thiophene-3-sulfonamide, N-(4-bromo-3-methyl-5-isoxazolyl)-2-LN-(3-methoxyphenyl)carboxamidelthiophene-3-sulfonamide; N-(4-bromo-3-methyl-5-isoxazolyl)-2-[N-(4-methoxyphenyl)carboxamide]thiophene-3-sulfonamide; N-(4-bromo-3-methyl-5-isoxazolyl)-5-benzenesulfonylthiophene-2-sulfonamide, N-(4-bromo-3-methyl-5-isoxazolyl)-1-(4'-isopropylphenyl)pyrrole-2-sulfonamide, N-(4-bromo-3-methyl-5-isoxazolyl)-1-(4'-isopropylphenyl)pyrrole-3-sulfonamide, N-(4-bromo-3-methyl-5-isoxazolyl)-2-{3-[1-methyl-5-(trifluoromethyl)pyrazolyl]}thiophene-5-sulfonamide, N-(4-bromo-3-methyl-5-isoxazolyl)-2-[N-(4-biphenyl)carboxamide]thiophene-3-sulfonamide, N-(4-bromo-3-methyl-5-isoxazolyl)-2-[N-(4-ethylphenyl)carboxamide]thiophene-3-sulfonamide, N-(4-bromo-3-methyl-5-isoxazolyl)-5-thienylthiophene-2-sulfonamide, N-(4-bromo-3-methyl-5-isoxazolyl)-5-(4-ethylphenyl)thiophene-2-sulfonamide, N-(4-bromo-5-methyl-3-isoxazolyl)thiophene-2-sulfonamide, N-(4-bromo-3-methyl-5-isoxazolyl)-5-chloro-3-methylbenzo[b]thiophene-2-sulfonamide, N-(3,4-dimethyl-5-isoxazolyl)benzo[b]thiophene-2-sulfonamide, N-(3,4-dimethyl-5-isoxazolyl)benzo[b]furan-2-sulfonamide, N-(3,4-dimethyl-5-isoxazolyl)benzo[b]thiophene-2-sulfonamide, N-(3,4-dimethyl-5-isoxazolyl)furan-2-sulfonamide, N-(3,4-dimethyl-5-isoxazolyl)-3-methoxy-2-thiophene sulfonamide, N-(4-bromo-3-methyl-5-isoxazolyl)-3-phenyl-2-1-5 thiophene sulfonamide, and N-(4-bromo-3-methyl-5-isoxazolyl)4-phenyl-2-thiophene sulfonamide.

35. The method of claim 1, wherein the endothelin antagonist is a compound of formula:

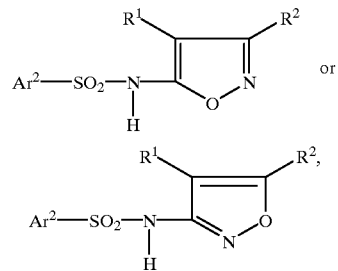

wherein, which $R^1$ and $R^2$ are either (i), (ii) or (iii) as follows:

(i) $R^1$ and $R^2$ are independently selected from H, $NH_2$, $NO_2$, halide, pseudohalide, alkyl, alkenyl, alkynyl, aryl, arylalkyl, heteroaryl, alkoxy, alkylamino, hydroxyalkyl, alkoxyalkyl, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, with the proviso that $R^2$ is not halide or pseudohalide; or, (ii) $R^1$ and $R^2$ together form $-(CH_2)_n$, where n is 3 to 6; or, (iii) $R^1$ and $R^2$ together form 1,3-butadienyl; and $Ar^2$ is thienyl, furyl, pyrrolyl, benzofuryl, thianaphthyl or indolyl, whereby nitric oxide levels are altered.

36. The method of claim 35, wherein the compound has the formulae:

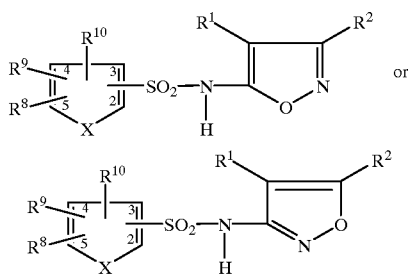

in which $R^1$, $R^2$, are either (i), (ii) or (iii) as follows:
(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, haloalkoxy, haloalkyl, alkylsufinyl, alkylsulfonyl, aryloxy, arylamino, arylthio, arylsufinyl, arylsulfonyl, aminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons, except the $R^2$ is not halide, pseudohalide or higher alkyl; or,
(ii) $R^1$ and $R^2$ together form —$(CH_2)_n$, where n is 3 to 6; or,
(iii) $R^1$ and $R^2$ together form 1,3-butadienyl; and
X is O, S, N or $NR^{11}$, where $R^{11}$, which is hydrogen or contains up to about 30 carbon atoms, and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z; and
$R^8$, $R^9$, $R^{10}$ are each independently selected as follows from (i) or (ii):
(i) $R^8$, $R^9$ and $R^{10}$, which each contain hydrogen or up to about 50 carbon atoms, generally up to about 30, more generally 20 or fewer, are each independently selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0–2, HNOH, $NR^{18}R^{19}$, $NO_2$, $N_3$, $OR^{18}$ $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl, cycloalkynyl or ureido; and any of the groups set forth for $R^8$, $R^9$ and $^{10}$ are unsubstituted or substituted with any substituents set forth for Z, which is halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl; or
(ii) any two of $R^8$, $R^9$ and $R^{10}$ form an aryl, aromatic ring, heteroaromatic ring, alicyclic or heterocyclic ring, which is saturated or unsaturated, containing from about 3 to about 16 members, more preferably 5 to 7 members that is unsubstituted or substituted with one or more substituents in each substituent is independently selected from Z; and the other of $R^8$, $R^9$ and $R^{10}$ is selected as in (i).

37. The method of claim 36, wherein $Ar^2$ is thienyl.
38. The method of claim 36, wherein $Ar^2$ is furyl.
39. The method of claim 36, wherein Ar2 is pyrrolyl.
40. The method of claim 36, wherein $R^1$ is H, lower alkyl, halide or pseudohalide; and $R^2$ is lower alkyl, lower alkenyl, lower alkynyl, lower haloalkyl, halide, pseudohalide or hydrogen.
41. The method of claim 36, wherein at least two of $R^8$, $R^9$ and $R^{10}$ hydrogen, halogen or lower alkyl, and the other is $C(O)R^{18}$, $CO_2R^{18}$, $NR^{18}R^{19}$, $R^{19}NCOR^{18}$ or $CONR^{19}R^{18}$; where $R^{18}$ is phenyl and $R^{19}$ is H or lower alkyl.
42. The method of claim 41, wherein $R^1$ is Br or Cl or alkyl and $R^2$ is lower alkyl, lower haloalkyl, or hydrogen.
43. The method of claim 36, wherein the compound is selected from the group consisting of N-(4-bromo-3-methyl-5-isoxazolyl)-[N-(4-methylphenyl)aminocarbonyl]thiophene-3-sulfonamide; N-(4-bromo-3-methyl-5-isoxazolyl)-5-(phentio)furan-2-sulfonamide; N-(4-bromo-3-methyl-5-isoxazolyl)-2-[N-(4-methoxyphenyl)aminocarbonyl]thiophene-3-sulfonamide; N-(4-bromo-3-methyl-5-isoxazolyl)-2-(N-phenylaminocarbonyl)thiophene-3-sulfonamide; N-(4-bromo-5-methyl-3-isoxazolyl)-2-(N-phenylaminocarbonyl)thiophene-3-sulfonamide; N-(3,4-dimethyl-5-isoxazolyl)-2-(N-phenylaminocarbonyl)thiophene-3-sulfonamide; N-(4-bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide; N-(4-chloro-3-methyl-5-isoxazolyl)-2-(carbomethoxy)thiophene-3-sulfonamide; N-(4-bromo-3-methyl-5-isoxazolyl)thiophene-2-sulfonamide; N-(4-bromo-3-methyl-5-isoxazolyl)-2-[N -(4-biphenyl)aminocarbonyl]thiophene-3-sulfonamide; N-(4-bromo-3-methyl-5-isoxazolyl)-2-[N-(2-methoxyphenyl)aminocarbonyl]thiophene-3-sulfonamide; N-(4-bromo-3-methyl-5-isoxazolyl)-2-(N-benzylaminocarbonyl)thiophene-3-sulfonamide; N-(4- bromo-3-methyl-5-isoxazolyl)-2-[N-(4-ethylphenyl)aminocarbonyl]-thiophene-3-sulfonamide; N-(4-bromo-3-methyl-5-isoxazolyl)-2-[N-(3-methoxyphenyl)aminocarbonyl]thiophene-3-sulfonamide; N-(4-bromo-3-methyl-5-isoxazolyl)-2-[N-(4-methoxyphenyl)aminocarbonyl]thiophene-3-sulfonamide; N-(4-bromo-3-methyl-5-isoxazolyl)-3-phenylthiophene-2-sulfonamide; N-(4-bromo-3-methyl-5-isoxazolyl)-4-phenylthiophene-2-sulfonamide; N-(4-bromo-3-methyl-5-isoxazolyl)-3-phenoxythiophene-2-sulfonamide; N-(4-bromo-3-methyl-5-isoxazolyl)-2-(4-tolulylaminocarbonylthiophene-3-sulfonamide; N-(4-bromo-3-methyl-5-isoxazolyl)-2-[N-(4-isopropylphenyl)aminocarbonyl]thiophene-3-sulfonamide; N-(4-bromo-3-methyl-5-isoxazolyl)-2-[N-(4-t-butylphenyl)aminocarbonyl]thiophene-3-sulfonamide; N-(4-bromo-3-methyl-5-isoxazolyl)-2-(4-butylphenyl)aminocarbonylthiophene-3-sulfonamide; N-(4-bromo-3-methyl-5-isoxazolyl)-2-[N-(4-sec-butylphenyl)aminocarbonyl]thiophene-3-sulfonamide; 3-phenethyl-N-(4-bromo-3-methyl-5-isoxazolyl)thiophene-2-sulfonamide; 4-phenethyl-N-(4-bromo-3-methyl-5-isoxazolyl)thiophene-2-sulfonamide; N-(4-Bromo-3-methyl-5-isoxazolyl)-5-(3-methoxyphenyl)thiophene-2-sulfonamide; N-(4-Bromo-3-methyl-5-isoxazolyl)-5-(3-methoxyphenyl)thiophene-2-sulfonamide; N-(4-Bromo-3-methyl-5-isoxazolyl)-5-(4-methoxyphenyl)thiophene-2-sulfonamide; N-(4-Bromo-3-methyl-5-isoxazolyl)-5-(3-thienyl)thiophene-2-sulfonamide; N-(4-bromo-3-methyl-5-isoxazolyl)-5-(benzenesulfonyl)thiophene-2-sulfonamide, N-(4-bromo-3-methyl-5-isoxazolyl)-1-(4'-isopropylphenyl)pyrrole-2-sulfonamide; N-(4-bromo-3-methyl-5-isoxazolyl)-1-(4'-isopropylphenyl)pyrrole-3-sulfonamide; N-(4-bromo-3-methyl-5-isoxazolyl)-2-{3-[1-methyl-5-(trifluoromethyl)pyrazolyl]}thiophene-5-sulfonamide; N-(4-bromo-3-methyl-5-isoxazolyl)-2-[N-(4-biphenyl)aminocarbonyl]thiophene-3-sulfonamide; N-(4-bromo-3-methyl-5-isoxazolyl)-2-[N-(4-ethylphenyl)aminocarbonyl]thiophene-3-sulfonamide; N-(4-bromo-3-methyl-5-isoxazolyl)-5-thienylthiophene-2-sulfonamide; N-(4-bromo-3-methyl-5-isoxazolyl)-5-(4-ethylphenyl)thiophene-2-sulfonamide; N-(4-chloro-3-methyl-5-isoxazolyl)-2-(phenylaminocarbonyl)thiophene-3-sulfonamide; N-(4-chloro-3-methyl-5-isoxazolyl)-5-benzylthiophene-2-sulfonamide; N-(4-chloro-3-methyl-5-isoxazolyl)-3-benzylthiophene-2-sulfonamide; N-(4-chloro-3-methyl-5-isoxazolyl)-3-phenethylthiophene-2-sulfonamide; N-(4-bromo-3-methyl-5-isoxazolyl)-3-styrylthiophene-2-sulfonamide; N-(4-bromo-3-methyl-5-isoxazolyl)-2-styrylthiophene-3-sulfonamide; N-(4-bromo-3-methyl-5-isoxazolyl)-2-phenoxythiophene-3-sulfonamide; N-(4-bromo-3-methyl-5-isoxazolyl)-2-(benzenesulfonyl)thiophene-3-sulfonamide; N-(4-bromo-3-methyl-5-isoxazolyl)-2-phenylthiophene-3-sulfonamide; N-(4-bromo-3-methyl-5-isoxazolyl)-2-aminothiophene-3-sulfonamide; N-(4-bromo-3-methyl-5-isoxazolyl)-2-(benzoylamino)thiophene-3-sulfonamide; N-(4-bromo-3-methyl-5-isoxazolyl)-3-benzylthiophene-2-sulfonamide; N-(4-bromo-3-methyl-5-isoxazolyl)-3-phenethylthiophene-2-sulfonamide; N-(4-bromo-3-methyl-5-isoxazolyl)-5-benzylthiophene-2-sulfonamide; N-(4-bromo-3-methyl-5-isoxazolyl)-2-[(N-phenyl)methylaminocarbonyl]thiophene-3-sulfonamide; N-(4-bromo-3-methyl-5-isoxazolyl)-5-benzylfuran-2-sulfonamide; N-(4-bromo-3-methyl-5-isoxazolyl)-5-(phenylthio)furan-2-sulfonamide; N-(4-bromo-3-methyl-5-isoxazolyl)-5-(hydroxymethyl)furan-2-sulfonamide; N-(4-bromo-3-methyl-5-isoxazolyl)-5-(carbomethoxy)furan-2-sulfonamide; N-(4-bromo-3-methyl-5-isoxazolyl)-2,5-dimethylfuran-3-sulfonamide; N-(4-bromo-3-methyl-5-isoxazolyl)-5-(4-isopropylphenyl)thiophene-2-sulfonamide; N-(4-bromo-3-methyl-5-isoxazolyl)-5-(4-propylphenyl)thiophene-2-sulfonamide; N-(4-bromo-3-methyl-5-isoxazolyl)-3-(phenylaminocarbonyl)thiophene-2-sulfonamide; N-(4-bromo-3-methyl-5-isoxazolyl)-2-benzylthiophene-3-sulfonamide; N-(4-bromo-3-methyl-5-isoxazolyl)-2-phenylthiophene-3-sulfonamide; N-(4-bromo-3-methyl-5-isoxazolyl)-2-(dimethylaminocarbonyl)thiophene-3-sulfonamide; N-(4-bromo-3-methyl-5-isoxazolyl)-2-(di-isopropylaminocarbonyl)thiophene-3-sulfonamide; N-(4-bromo-3-methyl-5-isoxazolyl)-2-(diethylaminocarbonyl)thiophene-3-sulfonamide; N-(4-bromo-3-methyl-5-isoxazolyl)-5-(4-iso-butylphenyl)furan-2-sulfonamide; N-(4-bromo-3-methyl-5-isoxazolyl)-5-styrylfuran-2-sulfonamide; N-(4-bromo-3-methyl-5-isoxazolyl)-5-styrylthiophene-2-sulfonamide; N-(4-bromo-3-methyl-5-isoxazolyl)2-thiophenesulfonamide; N-(4-Bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide; N-(4-bromo-3-methyl-5-isoxazolyl)-2-(N-phenylaminocarbonyl)thiophene-3-sulfonamide; N-(4-bromo-5-methyl-3-isoxazolyl)-2-(N-phenylaminocarbonyl)thiophene-3-sulfonamide; N-(4-chloro-3-methyl-5-isoxazolyl)-2-(N-phenylaminocarbonyl)thiophene-3-sulfonamide; N-(3,4-dimethyl-5-isoxazolyl)-2-(N-phenylaminocarbonyl)thiophene-3-sulfonamide; N-(4-Bromo-3-methyl-5-isoxazolyl)-2-[N-(4-methoxyphenyl)aminocarbonyl]thiophene-3-sulfonamide; N-(4-Bromo-3-methyl-5-isoxazolyl)-2-[N-(3-methoxyphenyl)aminocarbonyl]thiophene-3-sulfonamide; N-(4-Bromo-3-methyl-5-isoxazolyl)-2-[N-(2-methoxyphenyl)aminocarbonyl]thiophene-3-sulfonamide; N-(4-Bromo-3-methyl-5-isoxazolyl)-2-(N-benzylaminocarbonyl)thiophene-3-sulfonamide; N-(4-Bromo-3-methyl-5-isoxazolyl)-2-[N-(4-ethylphenyl)aminocarbonyl]thiophene-3-sulfonamide; N-(4-Bromo-3-methyl-5-isoxazolyl)-2-[N-(4-biphenyl)aminocarbonyl]-thiophene-3-sulfonamide; N-(4-bromo-3-methyl-5-isoxazolyl)-3-phenylthiophene-2-sulfonamide; N-(4-bromo-3-methyl-5-isoxazolyl)-2-[N-(4-methylphenyl)arninocarbonyl]thiophene-3-sulfonamide; N-(4-bromo-3-sulfonamide; N-(4-bromo-3-methyl-5-isoxazolyi)-2-[N(4-t-butylphenyl)aminocarbonyl]thiophene-3-sulfonamide; N-(4-bromo-3-methyl-5-isoxazolyl)-2-[N-(4-n-butylphenyl)aminocarbonyl]thiophene-3-sulfonamide; and N-(4-bromo-3-methyl-5-isoxazolyl)-2-[N-(4-sec-butylphenyl)aminocarbonyl]thiophene-3-sulfonamide; N-(4-bromo-3-methyl-5-isoxazolyl)-2-[N-(4-se-butylphenyl)aminocarbonyl]thiophene-3-sulfonamide; N-(4-bromo-3-methyl-5-isoxazolyl)-5-(4-ethylphenyl)thiophene-2-sulfonamide; N-(4-bromo-3-methyl-5-isoxazolyl)-2-[N-(4-ethylphenyl)aminocarbonyl]thiophene-3-sulfonamide; N-(4-bromo-3-methyl-5-isoxazolyl)-2-[N-(4-setyphenyl)aminocarbonyl]thiophene-3-sulfonamide; N-(4-bromo-3-methyl-5-isoxazolyl)-2-[N-(3-methoxyphenyl)aminocarbonyl]thiophene-3-sulfonamide; N-(4-Bromo-3-methyl-5-isoxazolyl)-2-[N-(4-methoxyphenyl)aminocarbonyl]thiophene-3-sulfonamide; N-(3,4-dimethyl-5-isoxazolyl)-2-(N-phenylaminocarbonyl)-thiophene-3-sulfonamide; N-(4-bromo-3-methyl-5-isoxazolyl)-2-(N-phenylaminocarbonyl)thiophene-3-sulfonamide; N-(4-bromo-3-methyl-5-isoxazolyl)2-thiophenesulfonamide; N-(4-bromo-3-methyl-5-isoxazolyl)-2,5-dimethylthiophene-3-sulfonamide; N-(4-bromo-3-methyl-5-isoxazolyl)-[N-(4-methylphenyl)aminocarbonyl]thiophene-3-sulfonamide; N-(4-chloro-3-methyl-5-isoxazolyl)-2-(N-phenylaminocarbonyl)thiophene-3-sulfonamide; and N-(4-chloro-3-methyl-5-isoxazolyl)-2-[N-(4-methoxyphenyl)aminocarbonyl]thiophene-3-sulfonamide.

* * * * *

UNITED STATES PATENT AND TRADEMARK OFFICE
CERTIFICATE OF CORRECTION

PATENT NO.    : 6,541,498 B2
DATED         : April 1, 2003
INVENTOR(S)   : Chan et al.

It is certified that error appears in the above-identified patent and that said Letters Patent is hereby corrected as shown below:

Column 4,
Line 60, please replace "(1002)" with -- (1992) --;

Column 42,
Line 1, please replace "– CH = CH$_2$–" with -- —CH = CH— --;

Please replace claims 5, 6, 7, 8, 10, 11, 12, 14, 15, 16, 17, 18, 19, 24, 34, 35, 36 and 43, with the following claims:

5. The method of claim 4, wherein:

(a) $R^1$ and $R^2$ are selected independently from the group consisting of lower alkyl, lower alkenyl, lower alkynyl, lower haloalkyl, halide, pseudohalide and H;

(b) X is $NR^{11}$, S or O, n is 0 or 1; $R^{11}$ is H, $CH_3$ or formyl; and $R^3$, $R^4$, $R^5$, $R^6$, $R^7$, $R^8$, $R^9$ and $R^{10}$ are either (i), (ii) or (iii) as follows:

(i) $R^4$ and $R^7$ are each independently selected from the group consisting of H, lower alkyl, $NH_2$, $NO_2$, halide, pseudohalide; $R^3$ is selected from the group consisting of H, NHOH, $NH_2$, $NO_2$, $N_3$, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from 1 up to 6 carbons and the aryl portions contain from 4 to 10 or 12 carbons; $R^5$, $R^6$, $R^{10}$ are H; $R^8$ and $R^9$ are each selected independently from among H, $NO_2$, $NH_2$ and halide; or (ii) $R^4$ and $R^7$ together form 1,3-butadienyl, 4-chloro-1,3-butadienyl, or 1-aza-1,3-butadienyl; $R^3$ is selected from the group consisting of H, NHOH, $NH_2$, $NO_2$, $N_3$, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 5 or 6 carbons and the aryl portions contain from 1 up to about 6 carbons; $R^5$, $R^6$, $R^{10}$ are H; $R^8$ and $R^9$ are each selected independently from among H, $NO_2$, $NH_2$ and halide; or (iii) $R^7$ and $R^3$ together together form 1,3-butadienyl, 3-chloro-1,3-butadienyl or 1-aza-1,3-butadienyl; $R^4$ is selected from the group consisting of H, lower alkyl, $NH_2$, $NO_2$, halide, pseudohalide; $R^5$, $R^6$, $R^{10}$ are H; $R^8$ and $R^9$ are each selected independently from among H, $NO_2$, $NH_2$ and halide.

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

6. The method of claim 4, wherein:
   (a) $R^1$ and $R^2$ are independently selected from the group consisting of H, $CH_3$, $C_2H_5$, $H_2C=CH$, $CH\equiv C$, Ph-O, Ph-$CH_2$, 4-$CH_3$-$C_6H_4$O halide, $CF_3$, $C_2F_5$, n-$C_3H_7$ and iso-$C_3H_7$; and
   (b) $Ar^2$ is $CH_3$ or is selected from

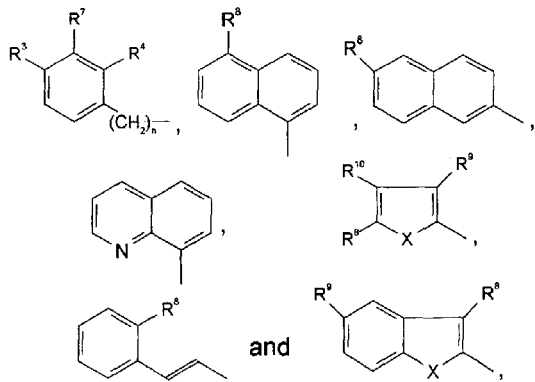

in which:
X is S or O; n is 0 or 1; $R^{11}$ is H; and $R^3$, $R^4$, $R^7$ and $R^8$ are either (i), (ii) or (iii) as follows:

(i) $R^8$ is H, $NO_2$, $NH_2$ or halide; $R^4$ and $R^7$ are each independently selected from the group consisting of H, halide, $NH_2$, $CF_3$, Ph and $CH_3$; and $R^3$ is selected from the group consisting of H, NHOH, $NH_2$, $C_2H_5$NH, $(CH_3)_2$N, Ph-$CH_2$NH, $NO_2$, F, Cl, Br, I, CN, $CH_3$, $(CH_3)_3$C, $C_5H_{11}$, $CH_3$O, n-$C_4H_9$O, $CH_2=CH$, Ph-CH=CH, $CH\equiv C$, Ph-$C\equiv C$, Ph, 3-(ethyoxycarbonylmethyl)ureido, and 3-cyclohexylureido; or (ii) $R^4$ and $R^7$ together form 1,3-butadienyl, 4-chloro-1,3-butadienyl, or 1-aza-1,3-butadienyl; $R^3$ is selected from the group consisting of H, NHOH, $NH_2$, EtNH, $(CH_3)_2$N, Ph-$CH_2$NH, $NO_2$, F, Cl, Br, I, CN, $CH_3$, $(CH_3)_3$C, $C_5H_{11}$, $CH_3$O, n-$C_4H_9$O, $CH_2=CH$, Ph-CH=CH, $CH\equiv C$, Ph-$C\equiv C$, Ph, 3-(ethyoxycarbonylmethyl)ureido, and 3-cyclohexylureido; and $R^8$ is H, $NO_2$, $NH_2$ or halide; or (iii) $R^7$ and $R^3$ together form 1,3-butadienyl, 3-chloro-1,3-butadienyl or 1-aza-1,3-butadienyl; $R^4$ is selected from the group consisting of H, halide, $NH_2$, $CF_3$, Ph and $CH_3$; and $R^8$ is H, $NO_2$, $NH_2$ or halide.

UNITED STATES PATENT AND TRADEMARK OFFICE
CERTIFICATE OF CORRECTION

PATENT NO.    : 6,541,498 B2
DATED         : April 1, 2003
INVENTOR(S)   : Chan et al.

It is certified that error appears in the above-identified patent and that said Letters Patent is hereby corrected as shown below:

7. The method of claim 6, wherein:
   $Ar^2$ is a substituted or unsubstituted phenyl group or substituted or unsubstituted naphthyl group or a substituted or unsubstituted quinolinyl group; $R^1$ is Br, Cl, H, $CH_3$, $C_2H_5$, $CF_3$; $R^2$ is H, $CH_3$, $C_2H_5$, or $CF_3$; and $R^3$, $R^4$, $R^7$, $R^8$, $R^9$, $R^{10}$ and $R^{11}$ are either (i), (ii), (iii) or (iv) as follows:

(i) $R^7$, $R^8$, $R^9$, $R^{10}$ and $R^{11}$ are H; n is 0 and $R^3$ is H, $NH_2$, $CH_3$, $CF_3$, halide, $C_2H_5NH$ or Ph, $R^4$ is H, $CF_3$, $NH_2$; or (ii) $R^3$, $R^8$, $R^9$, $R^{10}$ and $R^{11}$, are H; n is 0; and $R^4$ and $R^7$ together form 1, 3-butadienyl or 4-chloro-1,3-butadienyl; or (iii) $R^4$, $R^8$, $R^9$, $R^{10}$ and $R^{11}$, are H; n is 0 and $R^7$ and $R^3$ together form 1,3-butadienyl, 1-aza-1,3-butadienyl; or (iv) $R^7$, $R^8$, $R^9$, $R^{10}$ and $R^{11}$ are H; n is 1 and $R^3$ is H, $NH_2$ and halide; $R^4$ is H, $CF_3$, $NH_2$.

8. The method of claim 1, wherein the endothelin antagonist is a compound of formula:

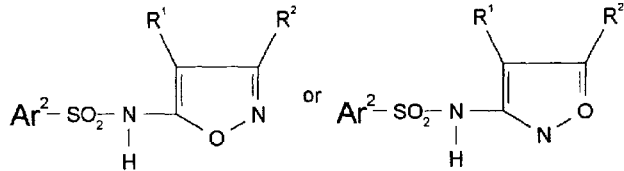

or a pharmaceutically acceptable salt thereof, wherein:
   $R^1$ and $R^2$ are either (i), (ii) or (iii) as follows:

(i) $R^1$ and $R^2$ are each independently selected from the group consisting of H, $NH_2$, $NO_2$, halide, pseudohalide, alkyl, alkenyl, alkynyl, aryl, arylalkyl, heteroaryl, alkoxy, alkylamino, alkylthio, alkyloxy, aminoalkyl, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido and substituted or unsubstituted ureido, in which the alkyl, alkenyl and alkynyl portions contain from 1 up to about 14 carbon atoms and are either straight or branched chains, and the aryl portions contain from about 4 to about 16 carbons; or,

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

(ii) $R^1$ and $R^2$ together form $-(CH_2)_n$, where n is 3 to 6; or, (iii) $R^1$ and $R^2$ together form 1,3-butadienyl;

$Ar^2$ is phenyl or a substituted phenyl and has the formula:

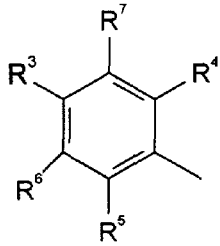

in which $R^3$, $R^4$, $R^5$, $R^6$, and $R^7$ are either (i) or (ii) as follows:

(i) $R^3$, $R^4$, $R^5$, $R^6$, and $R^7$ are each selected independently from the group consisting of H, NHOH, $NH_2$, $NO_2$, pseudohalide, halide, alkenyl, alkynyl, aryl, heteroaryl, alkoxy, alkylamino, dialkylamino, aminoalkyl, alkylthio, alkylalkoxy, alkylsulfinyl, alkylsulfonyl, aryloxy, arylalkyl, arylamino, arylthio, arylsulfinyl, arylsulfonyl, haloalkyl, haloalkoxy, haloaryl, alkoxycarbonyl, alkylcarbonyl, arylcarbonyl, carboxyl, hydroxyl, formyl, substituted or unsubstituted amido, substituted or unsubstituted ureido, where the alkyl, alkenyl, alkynyl portions are straight or branched chains, which are cyclic or acyclic, of from about 1 up to 10 carbons, and the aryl portions contain from 3 up to about 10 carbons;

(ii) $R^3$, $R^5$, and $R^7$ are H; and $R^4$ and $R^6$ are each independently selected from the group consisting of alkyl, alkoxy, halide, amino alkyl and dialkylaminoalkyl in which the alkyl and alkoxy groups contain from 1 to 10 carbons, and are straight or branched chains, whereby nitric oxide levels are altered.

10. The method of claim 8, wherein:

$R^1$ and $R^2$ are independently selected from the group consisting of H, $CH_3$, $C_2H_5$, $H_2C=CH$, $CH\equiv C$, Ph-O, Ph-$CH_2$, 4-$CH_3$-$C_6H_4O$, halide, $CF_3$, $C_2F_5$, n-$C_3H_7$, iso-$C_3H_7$, cyclo-$C_3H_7$, $nC_4H_9$, iso-$C_4H_9$, tert-$C_4H_9$, $nC_6H_{13}$, $nC_{13}H_{27}$ and $nC_9H_{19}$;

and $R^3$, $R^4$, $R^5$, $R^6$, and $R^7$ are either (i) or (ii) as follows:

(i) $R^4$, $R^5$, $R^6$ and $R^7$ are each independently selected from the group consisting of H, halide, $NH_2$, $CF_3$, Ph,$CH_3$, $CH_3O$, $NO_2$; and $R^3$ is selected from the group consisting of H, NHOH, $NH_2$, $C_2H_5NH$, $(CH_3)_2N$, Ph-$CH_2NH$, $NO_2$, F, Cl, Br, I, CN, $CH_3$, $(CH_3)_2CH$, $(CH_3)_3C$, $C_5H_{11}$, $CH_3O$, n-$C_4H_9O$, $CH_2=CH$, Ph-CH=CH, $CH\equiv C$, Ph-$C\equiv C$, Ph, 3-(ethyoxycarbonylmethyl)ureido, and 3-cyclohexylureido; or (ii) $R^3$, $R^5$, and $R^7$ are H; and $R^4$ and $R^6$ are alkyl groups that contain from 1 to 3 carbons, and are straight or branched chains.

UNITED STATES PATENT AND TRADEMARK OFFICE
CERTIFICATE OF CORRECTION

PATENT NO.  : 6,541,498 B2
DATED       : April 1, 2003
INVENTOR(S) : Chan et al.

It is certified that error appears in the above-identified patent and that said Letters Patent is hereby corrected as shown below:

11. The method of claim 8, wherein:
    $R^1$ is Br, Cl, H, $CH_3$, $C_2H_5$ or $CF_3$;
    $R^2$ is H, $CH_3$, $C_2H_5$ or $CF_3$;
    and $R^3$, $R^4$, $R^5$, $R^6$, and $R^7$ are either (i) or (ii) as follows:
    (i) $R^3$ is H, $NH_2$, $CH_3$, $CF_3$, halide, $CH_3$, $(CH_3)_3C$, $(CH_3)_2CH$ or $C_2H_5NH$; $R^4$, $R^5$ and $R^6$ are independently selected from H, $CH_3$, $C_2H_5$, $(CH_3)_2CH$, $CF_3$, $CH_3O$, F, Br, Cl and $NH_2$; and $R^7$ is H, $CH_3$, $C_2H_5$, $(CH_3)_2CH$, $CH_3O$, F, Br, Cl, or $CF_3$; or
    (ii) $R^3$, $R^5$, and $R^7$ are H; and $R^4$ and $R^6$ are ethyl.

12. The method of claim 1, wherein the endothelin antagonist is a compound of formula:

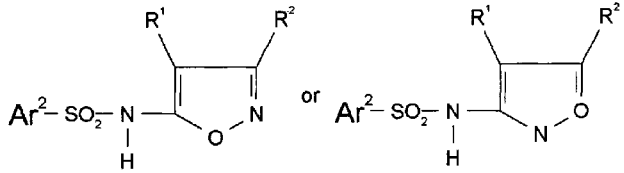

or a pharmaceutically acceptable salt thereof,
wherein:
$R^1$ is halide;
$R^2$ is selected from the group consisting of H, $NH_2$, alkyl, alkenyl, alkynyl, aryl, arylalkyl, heteroaryl, alkoxy, alkylamino, alkylthio, alkyloxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons; and
$Ar^2$ is substituted or unsubstituted alkyl or alkenyl in which the substitutents are selected from the group consisting of H, $NH_2$, halide, lower alkyl, aryl, alkoxy(lower)alkyl in which the alkyl portions contain from 1 up to 14 carbon atoms and are either straight or branched chains, the lower alkyl portions contain from 1 to 6 carbons, and the aryl portions contain from about 3 to about 16 carbons, or $Ar^2$ is a group selected from the group consisting of:

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

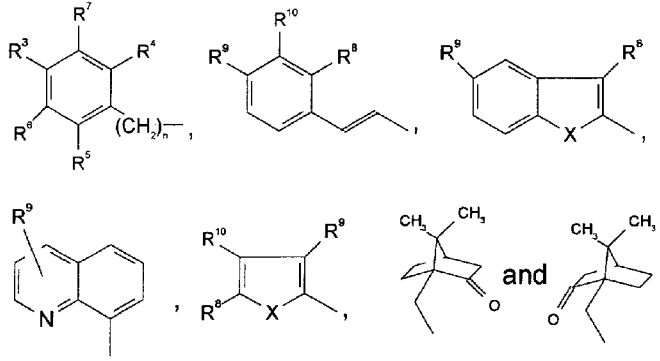

in which $R^3$, $R^4$, $R^5$, $R^6$, $R^7$, $R^8$, $R^9$, $R^{10}$ and $R^{11}$ are either (i), (ii), (iii) or (iv):

(i) $R^3$, $R^4$, $R^5$, $R^6$, and $R^7$ are each selected independently from the group consisting of H, NHOH, $NH_2$, $NO_2$, $N_3$, aminoalkyl, alkylamino, dialkylamino, dialkylaminoalkyl, carboxyl, carbonyl, hydroxyl, halide, pseudohalide, alkyl, alkenyl, alkynyl, aryl, heteroaryl, alkoxy, alkylamino, alkylthio, alkylalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido,substituted or unsubstituted ureido in which the alkyl, alkenyl, alkynyl portions are straight or branched chains of from 1 up to 10 carbons and the aryl portions contain from 3 to 10 carbons; $R^8$, $R^9$ and $R^{10}$ are each independently selected from H, $NH_2$, $NO_2$ and halide; X is O, S or $NR^{11}$ in which $R^{11}$ is H, alkyl, alkylcarbonyl or formyl; and n is from 0 up to about 6; or, alternatively, (ii) $R^4$ and $R^7$ together are substituted or unsubstituted 1, 3-butadienyl, 4-dimethylamino-1,3 butadienyl, 1-chloro-1,3-butadienyl, 4-dimethylamino-1,3-butadienyl, 1-aza-1,3-butadienyl or 2-aza-1,3-butadienyl groups; and n, X, $R^3$, $R^5$, $R^6$, $R^8$, $R^9$, $R^{10}$ and $R^{11}$ are as defined in (i) above; or alternatively, (iii) $R^7$ and $R^3$ together are substituted or unsubstituted 1, 3-butadienyl, 4-dimethylamino-1,3 butadienyl, 1-chloro-1,3-butadienyl, 4-dimethylamino-1,3-butadienyl, 1-aza-1,3-butadienyl or 2-aza-1,3-butadienyl groups; and n, X, $R^4$, $R^5$, $R^6$, $R^8$, $R^9$, $R^{10}$ and $R^{11}$ are as defined in (i); or alternatively

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

(iv) $R^3$, $R^5$, and $R^7$ are H; and $R^4$ and $R^6$ are each independently selected from the group consisting of alkyl, alkoxy, halide, amino alkyl and dialkylaminoalkyl in which the alkyl and alkoxy groups contain from 1 to 10 carbons, and are straight or branched chains; and $R^8$, $R^9$, $R^{10}$ and $R^{11}$ are as defined in (i), whereby nitric oxide levels are altered.

14. The method of claim 12, wherein $R^2$ is selected from the group consisting of H, $CH_3$, $C_2H_5$, $H_2C=CH$, $CH\equiv C$, Ph-O, Ph-$CH_2$, 4-$CH_3$-$C_6H_4$O, halide, $CF_3$, $C_2F_5$, n-$C_3H_7$, iso-$C_3H_7$, n$C_{13}H_{27}$ and n$C_9H_{19}$; $R^1$ is Cl or Br; X is NH, O or S; n is 0 or 1; and $R^3$, $R^4$, $R^5$, $R^6$, $R^7$, $R^8$, $R^9$, $R^{10}$ and $R^{11}$ are either (i), (ii), (iii) or (iv):

(i) $R^8$ and $R^9$ are H, $NO_2$, $NH_2$ or halide; $R^5$, $R^6$ and $R^{11}$ are H; $R^4$ and $R^7$ are each independently selected from the group consisting of H, halide, $NH_2$, $CF_3$, Ph, $CH_3$; and $R^3$ is selected from the group consisting of H, NHOH, $NH_2$, EtNH, $(CH_3)_2N$, Ph-$CH_2$NH, $NO_2$, F, Cl, Br, I, CN, $CH_3$, $(CH_3)_3C$, $C_5H_{11}$, $CH_3O$, n-$C_4H_9O$, $CH_2=CH$, Ph-CH=CH, CH$\equiv$C, dimethylaminomethyl, Ph-C$\equiv$C, Ph, 3-(ethoxycarbonylmethyl)ureido, and 3-cyclohexylureido; or (ii) $R^4$ and $R^7$ together form 1, 3-butadienyl, 4-chloro-1,3-butadienyl, 4-diamino-1,3-butadienyl or 1-aza-1,3-butadienyl; and $R^3$, $R^5$, $R^6$, $R^8$, $R^9$, $R^{10}$ and $R^{11}$ are defined as in (i); or (iii) $R^7$ and $R^3$ together form 1,3-butadienyl, 3-chloro-1,3-butadienyl, 4-diamino-1,3-butadienyl or 1-aza-1,3-butadienyl; and $R^4$, $R^5$, $R^6$, $R^8$, $R^9$, $R^{10}$ and $R^{11}$ are as defined in (i).; or (iv) $R^3$, $R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8$, $R^9$, $R^{10}$ and $R^{11}$ are as defined in (i).

15. The method of claim 12, wherein $R^1$ is Br or Cl; $R^2$ is selected from H, $CH_3$, $C_2H_5$, $H_2C=CH$, $CH\equiv C$, Ph-O, Ph-$CH_2$, 4-$CH_3$-$C_6H_4$O, halide, $CF_3$, $C_2F_5$, n-$C_3H_7$, iso-$C_3H_7$, n$C_{13}H_{27}$ and n$C_9H_{19}$; and $Ar^2$ is a substituted or unsubstituted phenyl group; and $R^3$, $R^4$, $R^5$, $R^6$ and $R^7$ are either (i), (ii) or (iii):

(i) $R^5$, $R^6$ and $R^7$ are H; n is 0; $R^3$ is H, $NH_2$, $CH_3$ $CF_3$, halide, $C_2H_5$NH or Ph; $R^4$ is H, $CF_3$, $NH_2$; or (ii) n is 1; $R^3$ is H, $NH_2$ or halide; $R^4$ is H, $CH_3$, Br, Cl, F, $CF_3$, $NH_2$, $R^7$ is H, $CH_3$, Br, Cl, F, $NH_2$ or $CF_3$; and $R^5$ and $R^6$ are H; or (iii) $R^3$, $R^5$, and $R^7$ are H; and $R^4$ and $R^6$ are each independently selected from the group consisting of alkyl groups that contain from 1 to 3 carbons.

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

16. The method of claim 12, wherein $R^1$ is Br or Cl; $R^2$ is H, $CH_3$, $C_2H_5$, $C_2F_5$ or $CF_3$; and $Ar^2$ is a substituted or unsubstituted naphthyl group or thianaphthyl group in which and $R^3$, $R^4$, $R^5$, $R^6$ and $R^7$ are either (i) or (ii):
 (i) $R^3$, $R^5$ and $R^6$ are H; n is 0 and $R^4$ and $R^7$ together form 1,3-butadienyl, 4-dimethylamino-1,3 butadienyl, 1-chloro-1,3-butadienyl, or 4-chloro-1,3-butadienyl; or
 (ii) $R^4$, $R^5$, $R^6$, $R^8$, $R^9$, $R^{10}$ and $R^{11}$ are H; n is 0; and $R^7$ and $R^3$ together form 1,3-butadienyl, 4-dimethylamino-1,3-butadienyl, 1-chloro-1,3-butadienyl, 1-aza-1,3-butadienyl.

17. The method of claim 12, wherein $R^1$ is Br or Cl; $R^2$ is selected from the group consisting of H, $CH_3$, $C_2H_5$, $H_2C=CH$, $CH\equiv C$, Ph-O, Ph-$CH_2$, 4-$CH_3$-$C_6H_4$O, halide, $CF_3$, $C_2F_5$, n-$C_3H_7$, iso-$C_3H_7$ and $C_4H_9$; and $Ar^2$ is selected from the group consisting of substituted or unsubstituted thiophenes, furans, a pyrroles, indoles, benzofurans, quinolines, isoquinolines, styrenes and thianaphthalenes in which $R^1$ is Cl or Br; X is NH, O or S; n is 0 or 1; in (i) $R^8$ and $R^9$ are H, $NO_2$, $NH_2$ or halide; $R^5$, $R^6$ and $R^{11}$ are independently selected from the group consisting of H, $CF_3$, halide, Cl and $NH_2$; $R^4$ and $R^7$ are each independently selected from the group consisting of H, halide, $NH_2$, $CF_3$, Ph, $CH_3$; and $R^3$ is selected from the group consisting of H, NHOH, $NH_2$, EtNH, $(CH_3)_2N$, Ph-$CH_2$NH, $NO_2$, F, Cl, Br, I, CN, $CH_3$, $(CH_3)_3C$, $C_5H_{11}$, $CH_3O$, n-$C_4H_9O$, $CH_2=CH$, Ph-CH=CH, CH$\equiv$C, Ph-C$\equiv$C, Ph, 3-(ethyoxycarbonylmethyl)ureido, and 3-cyclohexylureido; and in (iv) $R^3$, $R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8$, $R^9$, $R^{10}$ and $R^{11}$ are as defined in (i).

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

18. The method of claim 17, wherein $R^2$ is H, $CH_3$, $C_2H_5$, or $CF_3$; in (i) $R^3$ is H, $NH_2$, $CH_3$, $CF_3$, halide or $C_2H_5NH$; $R^4$, $R^5$ and $R^6$ are H; $R^7$ is selected from the group consisting of H, $CH_3$, $C_2H_5$, $(CH_3)_2CH$, F or $CF_3$, and $R^8$, $R^9$ and $R^{10}$ are independently selected from the group consisting of H, $NO_2$, $NH_2$ or halide; and $R^{11}$ is H; and in (iv) $R^3$, $R^5$, and $R^7$ are H; and $R^4$ and $R^6$ are each independently selected from the group consisting of alkyl groups that contain from 1 to 3 carbons, and are straight or branched chains; and $R^8$, $R^9$, $R^{10}$ and $R^{11}$ are as defined in (i).

19. The method of claim 1, wherein the endothelin antagonist is a compound of the formula:

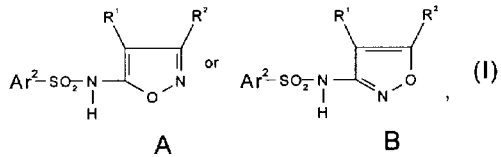

or a pharmaceutically acceptable salt thereof, wherein:

$R^1$ is halide;
$R^2$ is selected from the group consisting of H, $NH_2$, alkyl, alkenyl, alkynyl, aryl, arylalkyl, heteroaryl, alkoxy, alkylamino, alkylthio, alkyloxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons;
and $Ar^2$ is alkenyl, biphenyl, quinolyl, styryl, isoquinolyl, indolyl or thianaphthyl, whereby nitric oxide levels are altered.

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

24. The method of claim 23, wherein the compound has the formula:

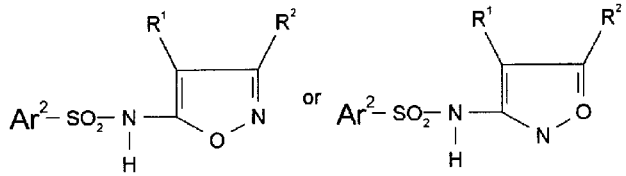

wherein $R^1$ and $R^2$ are selected from (i), (ii) or (iii):
  (i) $R^1$ and $R^2$ are each independently selected from the group consisting of H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or,
  (ii) $R^1$ and $R^2$ together form $-(CH_2)_n-$, where n is 3 to 6; or,
  (iii) $R^1$ and $R^2$ together form 1,3-butadienyl.

34. The method of claim 21, wherein the compound is selected from the group consisting of N-(4-bromo-3-methyl-5-isoxazolyl)-2-(N-phenylcarboxamide)thiophene-3-sulfonamide; N-(3,4-dimethyl-5-isoxazolyl)-2-(N-phenylcarboxamide)thiophene-3-sulfonamide, N-(4-bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide, N-(4-bromo-3-methyl-5-isoxazolyl)thiophene-2-sulfonamide, N-(4-bromo-3-methyl-5-isoxazolyl)-2-[N-(4-biphenyl)carboxamide]thiophene-3-sulfonamide, N-(4-bromo-3-methyl-5-isoxazolyl)-2-[N-(4-ethylphenyl)carboxamide]thiophene-3-sulfonamide, N-(4-bromo-3-methyl-5-isoxazolyl)-2-[N-(benzylcarboxamide]thiophene-3-sulfonamide, N-(4-bromo-3-methyl-5-isoxazolyl)-2-[N-(2-methoxyphenyl)carboxamide]thiophene-3-sulfonamide, N-(4-bromo-3-methyl-5-isoxazolyl)-2-[N-(3-methoxyphenyl)carboxamide]thiophene-3-sulfonamide; N-(4-bromo-3-methyl-5-isoxazolyl)-2-[N-(4-methoxyphenyl)carboxamide]thiophene-3-sulfonamide; N-(4-bromo-3-methyl-5-isoxazolyl)-5-benzenesulfonylthiophene-2-sulfonamide, N-(4-bromo-3-methyl-5-isoxazolyl)-1-(4'-isopropylphenyl)-pyrrole-2-sulfonamide, N-(4-bromo-3-methyl-5-isoxazolyl)-1-(4'-isopropylphenyl)pyrrole-3-sulfonamide, N-(4-bromo-3-methyl-5-isoxazolyl)-2-{3-[1-methyl-5-(trifluoromethyl)pyrazolyl]}thiophene-5-sulfonamide, N-(4-bromo-3-methyl-5-isoxazolyl)-2-[N-(4-biphenyl)carboxamide]thiophene-3-sulfonamide, N-(4-bromo-3-methyl-5-isoxazolyl)-2-[N-(4-ethylphenyl)carboxamide]thiophene-3-sulfonamide, N-(4-bromo-3-methyl-5-isoxazolyl)-5-thienylthiophene-2-sulfonamide, N-(4-bromo-3-methyl-5-isoxazolyl)-5-(4-ethylphenyl),

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

thiophene-2-sulfonamide, N-(4-bromo-5-methyl-3-isoxazolyl)thiophene-2-sulfonamide, N-(4-bromo-3-methyl-5-isoxazolyl)-5-chloro-3-methylbenzo[b]thiophene-2-sulfonamide, N-(3,4-dimethyl-5-isoxazolyl)benzo[b]thiophene-2-sulfonamide, N-(3,4-dimethyl-5-isoxazolyl)benzo[b]furan-2-sulfonamide, N-(3,4-dimethyl-5-isoxazolyl)benzo[b]thiophene-2-sulfonamide, N-(3,4-dimethyl-5-isoxazolyl)furan-2-sulfonamide, N-(3,4-dimethyl-5-isoxazolyl)-3-methoxy-2-thiophene sulfonamide, N-(4-bromo-3-methyl-5-isoxazolyl)-3-phenyl-2-thiophene sulfonamide, and N-(4-bromo-3-methyl-5-isoxazolyl)4-phenyl-2-thiophene sulfonamide.

35. The method of claim 1, wherein the endothelin antagonist is a compound of formula:

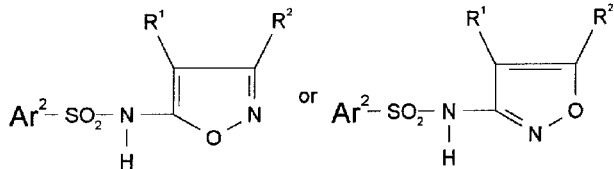

wherein, which $R^1$ and $R^2$ are either (i), (ii) or (iii) as follows:

(i) $R^1$ and $R^2$ are independently selected from H, $NH_2$, $NO_2$, halide, pseudohalide, alkyl, alkenyl, alkynyl, aryl, arylalkyl, heterolaryl, alkoxy, alkylamino, hydroxyalkyl, alkoxyalkyl, alkylthio, haloalkoxy, haloalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, with the proviso that $R^2$ is not halide or pseudohalide; or, (ii) $R^1$ and $R^2$ together form $-(CH_2)_n$, where n is 3 to 6; or, (iii) $R^1$ and $R^2$ together form 1,3-butadienyl; and $Ar^2$ is thienyl, furyl, pyrrolyl, benzofuryl, thianaphthyl or indolyl, whereby nitric oxide levels are altered.

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

36. The method of claim 35, wherein the compound has the formulae:

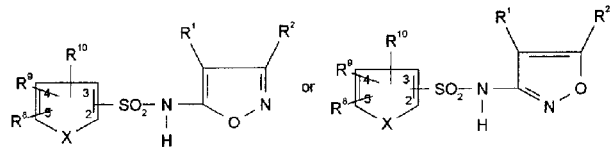

in which $R^1$, $R^2$, are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, haloalkoxy, haloalkyl, alkylsulfinyl, alkylsulfonyl, aryloxy, arylamino, arylthio, arylsulfinyl, arylsulfonyl, aminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons, except the $R^2$ is not halide, pseudohalide or higher alkyl; or, (ii) $R^1$ and $R^2$ together form $-(CH_2)_n$, where n is 3 to 6; or, (iii) $R^1$ and $R^2$ together form 1,3-butadienyl; and X is O, S, N or $NR^{11}$, where $R^{11}$, which is hydrogen or contains up to about 30 carbon atoms, and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0-2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0-2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl,

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

$C(O)R^{17}$ and $S(O)_nR^{17}$ in which n is 0-2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with any of the groups set forth for Z; and $R^8$, $R^9$, $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0-2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl, cycloalkynyl or ureido; and any of the groups set forth for $R^8$, $R^9$ and $R^{10}$ are unsubstituted or substituted with any substituents set forth for Z, which is halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0-2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0-2; and $R^{21}$ and $R^{23}$ areindependently selected from hydrogen, alkyl, alkenyl, alkynyl, aryl, alkylaryl, heterocycle, aralkyl, aralkoxy, cycloalkyl, cycloalkenyl or cycloalkynyl; or (ii) any two of $R^8$, $R^9$ and $R^{10}$ form an aryl, aromatic ring, heteroaromatic ring, alicyclic or heterocyclic ring, which is saturated or unsaturated, containing from about 3 to about 16 members, more preferably 5 to 7 members that is unsubstituted or substituted with one or more substituents in each substituent is independently selected from Z; and the other of $R^8$, $R^9$ and $R^{10}$ is selected as in (i).

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

43. The method of claim 36, wherein the compound is selected from the group consisting of N-(4-bromo-3-methyl-5-isoxazolyl)-[N-(4-methylphenyl)aminocarbonyl]thiophene-3-sulfonamide; N-(4-bromo-3-methyl-5-isoxazolyl)-5-(phenylthio)furan-2-sulfonamide; N-(4-bromo-3-methyl-5-isoxazolyl)-2-[N-(4-methoxyphenyl)aminocarbonyl]thiophene-3-sulfonamide; N-(4-bromo-3-methyl-5-isoxazolyl)-2-(N-phenylaminocarbonyl)thiophene-3-sulfonamide; N-(4-bromo-5-methyl-3-isoxazolyl)-2-(N-phenylaminocarbonyl)thiophene-3-sulfonamide; N-(3,4-dimethyl-5-isoxazolyl)-2-(N-phenylaminocarbonyl)thiophene-3-sulfonamide; N-(4-bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide; N-(4-chloro-3-methyl-5-isoxazolyl)-2-(carbomethoxy)thiophene-3-sulfonamide; N-(4-bromo-3-methyl-5-isoxazolyl)thiophene-2-sulfonamide; N-(4-bromo-3-methyl-5-isoxazolyl)-2-[N-(4-biphenyl)aminocarbonyl]thiophene-3-sulfonamide; N-(4-bromo-3-methyl-5-isoxazolyl)-2-[N-(2-methoxyphenyl)aminocarbonyl]thiophene-3-sulfonamide; N-(4-bromo-3-methyl-5-isoxazolyl)-2-(N-benzylaminocarbonyl)thiophene-3-sulfonamide; N-(4-bromo-3-methyl-5-isoxazolyl)-2-[N-(4-ethylphenyl)aminocarbonyl]-thiophene-3-sulfonamide; N-(4-bromo-3-methyl-5-isoxazolyl)-2-[N-(3-methoxyphenyl)aminocarbonyl]thiophene-3-sulfonamide; N-(4-bromo-3-methyl-5-isoxazolyl)-2-[N-(4-methoxyphenyl)aminocarbonyl]thiophene-3-sulfonamide; N-(4-bromo-3-methyl-5--isoxazolyl)-3-phenylthiophene-2-sulfonamide; N-(4-bromo-3-methyl-5-isoxazolyl)-4-phenylthiophene-2-sulfonamide; N-(4-bromo-3-methyl-5-isoxazolyl)-3-phenoxythiophene-2-sulfonamide; N-(4-bromo-3-methyl-5-isoxazolyl)-2-(4-toluyl-aminocarbonyl)thiophene-3-sulfonamide; N-(4-bromo-3-methyl-5-isoxazolyl)-2-[N-(4-isopropylphenyl)aminocarbonyl]

thiophene-3-sulfonamide; N-(4-bromo-3-methyl-5-isoxazolyl)-2-[N-(4-t-butylphenyl)-aminocarbonyl]thiophene-3-sulfonamide; N-(4-bromo-3-methyl-5-isoxazolyl)-2-(4-butylphenyl)aminocarbonylthiophene-3-sulfonamide; N-(4-bromo-3-methyl-5-isoxazolyl)-2-[N-(4-sec-butylphenyl)aminocarbonyl]thiophene-3-sulfonamide; 3-phenethyl-N-(4-bromo-3-methyl-5-isoxazolyl)thiophene-2-sulfonamide; 4-phenethyl-N-(4-bromo-3-methyl-5-isoxazolyl)thiophene-2-sulfonamide; N-(4-Bromo-3-methyl-5-isoxazolyl)-5-(3-methoxyphenyl)thiophene-2-sulfonamide; N-(4-Bromo-3-methyl-5-isoxazolyl)-5-(3-methoxyphenyl)thiophene-2-sulfonamide; N-(4-Bromo-3-methyl-5-isoxazolyl)-5-(4-methoxyphenyl)thiophene-2-sulfonamide; N-(4-Bromo-3-methyl-5-isoxazolyl)-5-(3-thienyl)thiophene-2-sulfonamide; N-(4-bromo-3-methyl-5-isoxazolyl)-5-(benzenesulfonyl)thiophene-2-sulfonamide, N-(4-bromo-3-methyl-5-isoxazolyl)-1-(4'-

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

isopropylphenyl)pyrrole-2-sulfonamide; N-(4-bromo-3-methyl-5-isoxazolyl)-1-(4'-isopropylphenyl)pyrrole-3-sulfonamide; N-(4-bromo-3-methyl-5-isoxazolyl)-2-{3-[1-methyl-5-(trifluoromethyl)pyrazolyl]}thiophene-5-sulfonamide; N-(4-bromo-3-methyl-5-isoxazolyl)-2-[N-(4-biphenyl)aminocarbonyl]thiophene-3-sulfonamide; N-(4-bromo-3-methyl-5-isoxazolyl)-2-[N-(4-ethylphenyl)aminocarbonyl]thiophene-3-sulfonamide; N-(4-bromo-3-methyl-5-isoxazolyl)-5-thienylthiophene-2-sulfonamide; N-(4-bromo-3-methyl-5-isoxazolyl)-5-(4-ethylphenyl)thiophene-2-sulfonamide; N-(4-chloro-3-methyl-5-isoxazolyl)-2-(phenylaminocarbonyl)thiophene-3-sulfonamide; N-(4-chloro-3-methyl-5-isoxazolyl)-5-benzylthiophene-2-sulfonamide; N-(4-chloro-3-methyl-5-isoxazolyl)-3-benzylthiophene-2-sulfonamide; N-(4-chloro-3-methyl-5-isoxazolyl)-3-phenethylthiophene-2-sulfonamide; N-(4-bromo-3-methyl-5-isoxazolyl)-3-styrylthiophene-2-sulfonamide; N-(4-bromo-3-methyl-5-isoxazolyl)-2-styrylthiophene-3-sulfonamide; N-(4-bromo-3-methyl-5-isoxazolyl)-2-phenoxythiophene-3-sulfonamide; N-(4-bromo-3-methyl-5-isoxazolyl)-2-(benzenesulfonyl)thiophene-3-sulfonamide; N-(4-bromo-3-methyl-5-isoxazolyl)-2-phenylthiophene-3-sulfonamide; N-(4-bromo-3-methyl-5-isoxazolyl)-2-aminothiophene-3-sulfonamide; N-(4-bromo-3-methyl-5-isoxazolyl)-2-(benzoylamino)thiophene-3-sulfonamide; N-(4-bromo-3-methyl-5-isoxazolyl)-3-benzylthiophene-2-sulfonamide; N-(4-bromo-3-methyl-5-isoxazolyl)-3-phenethylthiophene-2-sulfonamide; N-(4-bromo-3-methyl-5-isoxazolyl)-5-benzylthiophene-2-sulfonamide; N-(4-bromo-3-methyl-5-isoxazolyl)-2-[(N-phenyl)methylaminocarbonyl]thiophene-3-sulfonamide; N-(4-bromo-3-methyl-5-isoxazolyl)-5-benzylfuran-2-sulfonamide; N-(4-bromo-3-methyl-5-isoxazolyl)-5-(phenylthio)furan-2-sulfonamide; N-(4-bromo-3-methyl-5-isoxazolyl)-5-(hydroxymethyl)furan-2-sulfonamide; N-(4-bromo-3-methyl-5-isoxazolyl)-5-(carbomethoxy)furan-2-sulfonamide; N-(4-bromo-3-methyl-5-isoxazolyl)-2,5-dimethylfuran-3-sulfonamide; N-(4-bromo-3-methyl-5-isoxazolyl)-5-(4-isopropyl-phenyl)thiophene-2-sulfonamide; N-(4-bromo-3-methyl-5-isoxazolyl)-5-(4-propylphenyl)thiophene-2-sulfonamide; N-(4-bromo-3-methyl-5-isoxazolyl)-3-(phenylaminocarbonyl)thiophene-2-sulfonamide; N-(4-bromo-3-methyl-5-isoxazolyl)-2-benzylthiophene-3-sulfonamide; N-(4-bromo-3-methyl-5-isoxazolyl)-2-phenylthiophene-3-sulfonamide; N-(4-bromo-3-methyl-5-isoxazolyl)-2-(dimethylaminocarbonyl)thiophene-3-sulfonamide; N-(4-bromo-3-methyl-5-isoxazolyl)-2-(di-iso-propylaminocarbonyl)thiophene-3-sulfonamide; N-(4-bromo-3-methyl-5-isoxazolyl)-2-(diethylaminocarbonyl)thiophene-3-sulfonamide; N-(4-

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

bromo-3-methyl-5-isoxazolyl)-5-(4-iso-butylphenyl)furan-2-sulfonamide; N-(4-bromo-3-methyl-5-isoxazolyl)-5-styrylfuran-2-sulfonamide; N-(4-bromo-3-methyl-5-isoxazolyl)-5-styrylthiophene-2-sulfonamide; N-(4-bromo-3-methyl-5-isoxazolyl)2-thiophenesulfonamide; N-(4-Bromo-3-methyl-5-isoxazolyl)-2,5-dimethylthiophene-3-sulfonamide; N-(4-bromo-3-methyl- 5-isoxazolyl)-2-(carbomethoxy)thiophene-3-sulfonamide; N-(4-bromo-3-methyl-5-isoxazolyl)-2-(N-phenylaminocarbonyl)thiophene-3-sulfonamide; N-(4-bromo-5-methyl-3-isoxazolyl)-2-(N-phenylaminocarbonyl)thiophene-3-sulfonamide; N-(4-chloro-3-methyl-5-isoxazolyl)-2-(N-phenylaminocarbonyl)thiophene-3-sulfonamide; N-(3,4-dimethyl-5-isoxazolyl)-2-(N-phenylaminocarbonyl)thiophene-3-sulfonamide; N-(4-Bromo-3-methyl-5-isoxazolyl)-2-[N-(4-methoxyphenyl)aminocarbonyl]thiophene-3-sulfonamide; N-(4-Bromo-3-methyl-5-isoxazolyl)-2-[N-(3-methoxyphenyl)aminocarbonyl]thiophene-3-sulfonamide; N-(4-Bromo-3-methyl-5-isoxazolyl)-2-[N-(2-methoxyphenyl)aminocarbonyl]thiophene-3-sulfonamide; N-(4-Bromo-3-methyl-5-isoxazolyl)-2-(N-benzylaminocarbonyl)thiophene-3-sulfonamide; N-(4-Bromo-3-methyl-5-isoxazolyl)-2-[N-(4-ethylphenyl)aminocarbonyl]thiophene-3-sulfonamide;
N-(4-Bromo-3-methyl-5-isoxazolyl)-2-[N-(4-biphenyl)aminocarbonyl]thiophene-3-sulfonamide; N-(4-bromo-3-methyl-5-isoxazolyl)-3-phenylthiophene-2-sulfonamide; N-(4-bromo-3-methyl-5-isoxazolyl)-2-[N-(4-methylphenyl)aminocarbonyl]thiophene-3-sulfonamide; N-(4-bromo-3-methyl-5-isoxazolyl)-2-[N-(4-isopropylphenyl)-aminocarbonyl]thiophene-3-sulfonamide; N-(4-bromo-3-methyl-5-isoxazolyl)-2-[N-(4-t-butylphenyl)aminocarbonyl]thiophene-3-sulfonamide; N-(4-bromo-3-methyl-5-isoxazolyl)-2-[N-(4-n-butylphenyl)aminocarbonyl]thiophene-3-sulfonamide; and N-(4-bromo-3-methyl-5-isoxazolyl)-2-[N-(4-sec-butylphenyl)aminocarbonyl]

UNITED STATES PATENT AND TRADEMARK OFFICE
CERTIFICATE OF CORRECTION

PATENT NO. : 6,541,498 B2
DATED : April 1, 2003
INVENTOR(S) : Chan et al.

It is certified that error appears in the above-identified patent and that said Letters Patent is hereby corrected as shown below:

thiophene-3-sulfonamide; N-(4-bromo-3-methyl-5-isoxazolyl)-2-[N-(4-sec-butylphenyl)aminocarbonyl]thiophene-3-sulfonamide; N-(4-bromo-3-methyl-5-isoxazolyl)-5-(4-ethylphenyl)thiophene-2-sulfonamide; N-(4-bromo-3-methyl-5-isoxazolyl)-2-[N-(4-ethylphenyl)aminocarbonyl]thiophene-3-sulfonamide;[[N-(4-setyphenyl)aminocarbonyl]thiophene-3-sulfonamide;] N-(4-bromo-3-methyl-5-isoxazolyl)-2-[N-(3-methoxyphenyl)aminocarbonyl]thiophene-3-sulfonamide; N-(4-bromo-3-methyl-5-isoxazolyl)-2-[N-(3-methoxyphenyl)aminocarbonyl]thiophene-3-sulfonamide; N-(4-Bromo-3-methyl-5-isoxazolyl)-2-[N-(4-methoxyphenyl)aminocarbonyl]thiophene-3-sulfonamide; N-(3,4-dimethyl-5-isoxazolyl)-2-(N-phenylaminocarbonyl)thiophene-3-sulfonamide; N-(4-bromo-3-methyl-5-isoxazolyl)-2-(N-phenylaminocarbonyl)thiophene-3-sulfonamide; N-(4-bromo-3-methyl-5-isoxazolyl)2-thiophenesulfonamide; N-(4-bromo-3-methyl-5-isoxazolyl)-2,5-dimethylthiophene-3-sulfonamide; N-(4-bromo-3-methyl-5-isoxazolyl)-[N-(4-methylphenyl)aminocarbonyl]thiophene-3-sulfonamide; N-(4-chloro-3-methyl-5-isoxazolyl)-2-(N-phenylaminocarbonyl)thiophene-3-sulfonamide; and N-(4-chloro-3-methyl-5-isoxazolyl)-2-[N-(4-methoxyphenyl)aminocarbonyl]thiophene-3-sulfonamide.

Signed and Sealed this

Nineteenth Day of August, 2003

JAMES E. ROGAN
*Director of the United States Patent and Trademark Office*